US012790631B2

(12) United States Patent
Lewis et al.

(10) Patent No.: US 12,790,631 B2
(45) Date of Patent: Nov. 10, 2026

(54) MANUFACTURING PROCESS FOR PROTEIN

(71) Applicant: Bristol-Myers Squibb Company, Princeton, NJ (US)

(72) Inventors: Amanda Morgan Lewis, Devens, MA (US); Daniel Robert Maskas, Devens, MA (US); Eric Richard Garr, Devens, MA (US); Diane Kay Worrell, Devens, MA (US); Richard Thomas Ludwig, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 606 days.

(21) Appl. No.: 18/041,669

(22) PCT Filed: Aug. 13, 2021

(86) PCT No.: PCT/US2021/046029

§ 371 (c)(1),
(2) Date: Feb. 14, 2023

(87) PCT Pub. No.: WO2022/036275

PCT Pub. Date: Feb. 17, 2022

(65) Prior Publication Data

US 2023/0313259 A1 Oct. 5, 2023

Related U.S. Application Data

(60) Provisional application No. 63/066,122, filed on Aug. 14, 2020.

(51) Int. Cl.
*C12P 21/02* (2006.01)
*C12N 5/00* (2006.01)

(52) U.S. Cl.
CPC ............ *C12P 21/02* (2013.01); *C12N 5/0018* (2013.01); *C12N 2523/00* (2013.01)

(58) Field of Classification Search
CPC ............................ C12P 21/02; C12N 2523/00
See application file for complete search history.

(56) References Cited

U.S. PATENT DOCUMENTS

| | | | |
|---|---|---|---|
| 8,765,413 B2 | 7/2014 | Joosten et al. |
| 9,428,727 B2 | 8/2016 | Leist et al. |
| 2016/0039924 A1 | 2/2016 | Zeng |
| 2018/0230445 A1 | 8/2018 | Jaluria et al. |
| 2019/0085370 A1 | 3/2019 | Leiske et al. |

FOREIGN PATENT DOCUMENTS

| | | | |
|---|---|---|---|
| JP | 2018521676 A | 8/2018 |
| WO | WO-2004058800 A2 | 7/2004 |
| WO | WO-2004058944 A1 | 7/2004 |
| WO | WO-2005035748 A1 | 4/2005 |
| WO | WO-2007076032 A2 | 7/2007 |
| WO | WO-2009112250 A1 | 9/2009 |
| WO | WO-2013006479 A2 | 1/2013 |
| WO | WO-2013114164 A1 | 8/2013 |
| WO | WO-2018170099 A1 | 9/2018 |

OTHER PUBLICATIONS

Bluestone et al., "CTLA4Ig: Bridging the Basic Commentary Immunology with Clinical Application", Immunity, vol. 24, pp. 233-238. (Year: 2006).*
Anumula, K.R., "Single tag for total carbohydrate analysis," Anal Biochem 457:31-37, Elsevier, Netherlands (Jul. 2014).
Barnes, D., and Sato, G., "Methods for growth of cultured cells in serum-free medium," Anal Biochem 102(2):255-270, Elsevier, Netherlands (Mar. 1980).
Boyle, M. D. P., et al., "Applications of Bacterial Immunoglobulin-Binding Proteins to the Purification of Immunoglobulins" Mol Int Bioseparations, pp. 91-112, Boston, MA: Springer, United States (Dec. 1993).
De Oliveira, K., et al., "Site-specific monitoring of N-Glycosylation profiles of a CTLA4-Fc-fusion protein from the secretory pathway to the extracellular environment," Biotechnol Bioeng 114(7):1550-1560, Wiley, United States (Jul. 2017).
Dhume, S.T., et al., "Monitoring glycosylation of therapeutic glycoproteins for consistency by HPLC using highly fluorescent anthranilic acid (AA) tag," Methods Mol Biol 446:317-331, Humana Press, United States (2008).
Ham, R.G., and McKeehan, W.L., "Media and growth requirements, " Methods Enzymol 58:44-93, Academic Press, United States (Jan. 1979).
Hennicke, J., et al., "Impact of temperature and pH on recombinant human IgM quality attributes and productivity," N Biotechnol 50:20-26, Elsevier, Netherlands (May 2019).
Hou, K.C., et al., "Protein A immobilized affinity cartridge for immunoglobulin purification," Biotechnol Appl Biochem 13(2):257-68 (Apr. 1991).
International Search Report and Written Opinion for International Application No. PCT/US2021/046029, European Patent Office, Netherlands, mailed Apr. 7, 2022, 35 pages.
Kerem, I., "Carbon Dioxide Control in Bioreactors and the Application of Principal Component Analysis to Cell Culture Process Data," Thesis, Newcastle University, published May 1, 2017.
Trummer, E., et al., "Process parameter shifting: Part II. Biphasic cultivation—A tool for enhancing the volumetric productivity of batch processes using Epo-Fc expressing CHO cells," Biotechnol Bioeng 94(6): 1045-1052, Wiley, United States (May 2006).
Zhang, L., et al., "Glycan analysis of therapeutic glycoproteins," MAbs 8(2):205-215, Taylor & Francis, United Kingdom (Feb. 2016).

* cited by examiner

*Primary Examiner* — Melenie L Gordon
*Assistant Examiner* — Grant C Currens
(74) *Attorney, Agent, or Firm* — STERNE, KESSLER, GOLDSTEIN & FOX P.L.L.C.

(57) ABSTRACT

This disclosure provides a novel method of controlling the glycosylation profile of a protein during production. The disclosure also provides a novel method of improving protein yield while controlling the glycosylation profile of a protein.

11 Claims, 30 Drawing Sheets

Specification includes a Sequence Listing.

FIG. 1D

N-Glycopeptide Sequences

| Peptide | Glycosylation Site | Protease | Amino Acid Sequence |
|---|---|---|---|
| T5 | Asn76 | Trypsin and GluC | LTFLDDSICTGTSSGNQV<u>N</u>LTIQGLR (SEQ ID NO: 9) |
| T7 | Asn108 | Trypsin and GluC | VELMYPPPYYLGIG<u>N</u>GTQIYVIDPEPCPDSDQEPK (SEQ ID NO: 10) |
| T14 | Asn207 | Trypsin and GluC | EEQY<u>N</u>STYR (SEQ ID NO: 11) |

Underline: N-glycosylation site.

Mean production bioreactor VCD profiles by treatment group

FIG. 2B

| Treatment | Mean Peak VCD ($10^6$ cells/mL) | Peak VCD Dunnett's Test p-Value | Mean Day 0 - 5 Doubling Time (hrs) | Doubling Time Dunnett's Test p-Value | Mean Day 0 - 14 IVCD ($10^9$ cells-day/mL) | IVCD Dunnett's Test p-Value | VCD Profile Value |
|---|---|---|---|---|---|---|---|
| Control | 13.8 | N/A | 34.8 | N/A | 0.11 | N/A | N/A |
| High CO2 | 13.4 | 1.00 | 33.6 | 0.97 | 0.11 | 1.00 | 0.43 |
| Late First Feed | 14.0 | 1.00 | 33.3 | 0.85 | 0.12 | 1.00 | 0.58 |
| Low Initial pH | 9.2 | < 0.01 | 41.1 | 0.01 | 0.07 | < 0.01 | 0.02 |
| Low Initial VCD | 7.0 | < 0.01 | 34.8 | 0.95 | 0.05 | < 0.01 | < 0.01 |
| High Initial VCD | 14.5 | 0.98 | 37.7 | 0.80 | 0.12 | 1.00 | 0.52 |
| Low Overall Temp | 11.2 | 0.12 | 35.1 | 1.00 | 0.10 | 0.30 | 0.08 |
| Early pH Shift | 11.7 | 0.27 | 37.2 | 0.83 | 0.10 | 0.22 | 0.04 |
| Low Temp Shift 1 | 12.9 | 0.93 | 33.0 | 1.00 | 0.11 | 0.98 | 0.41 |
| Low Temp Shift 2 | 13.3 | 1.00 | 36.3 | 0.98 | 0.11 | 0.90 | 0.62 |

FIG. 4A

Statistical comparison of Day 14 sialic acid and N-link domain results

| Treatment | Mean Day 14 NANA (MR) | NANA Dunnett's Test P-Value | Mean Day 14 NGNA (MR) | NGNA Dunnett's Test P-Value | Mean Day 14 Domain I (MR) | Domain I Dunnett's Test P-Value | Mean Day 14 Domain II (MR) | Domain II Dunnett's Test P-Value | Mean Day 14 Domain III (MR) | Domain III Dunnett's Test P-Value | Mean Day 14 Domain IV+V (MR) | Domain IV+V Dunnett's Test P-Value |
|---|---|---|---|---|---|---|---|---|---|---|---|---|
| Control | 8.50 | N/A | 0.85 | N/A | 33.45 | N/A | 29.65 | N/A | 25.5 | N/A | 11.40 | N/A |
| High $CO_2$ | 8.70 | 0.86 | 0.75 | 0.87 | 34.30 | 0.97 | 30.60 | 0.70 | 24.9 | 1.00 | 10.25 | 0.17 |
| Late First Feed | 8.70 | 0.86 | 0.70 | 0.55 | 33.05 | 1.00 | 29.60 | 1.00 | 26.45 | 0.97 | 10.90 | 0.86 |
| Low Initial pH | 8.60 | 1.00 | 0.90 | 1.00 | 31.55 | 0.49 | 30.35 | 0.90 | 27.80 | 0.39 | 10.35 | 0.23 |
| Low Initial VCD | 8.70 | 0.86 | 1.15 | 0.06 | 30.45 | 0.13 | 29.75 | 1.00 | 28.45 | 0.19 | 11.40 | 1.00 |
| High Initial VCD | 8.40 | 1.00 | 0.85 | 1.00 | 34.75 | 0.81 | 30.65 | 0.65 | 24.20 | 0.87 | 10.35 | 0.23 |
| Low Overall Temperature | 8.30 | 0.86 | 0.80 | 1.00 | 33.55 | 1.00 | 30.05 | 1.00 | 26.85 | 0.85 | 9.55 | 0.02 |
| Early pH Shift Timing | 8.75 | 0.70 | 0.90 | 1.00 | 31.70 | 0.57 | 30.20 | 0.97 | 27.10 | 0.73 | 11.00 | 0.95 |
| Low Temp Shift 1 | 8.60 | 1.00 | 0.75 | 0.87 | 33.35 | 1.00 | 31.05 | 0.33 | 25.95 | 1.00 | 9.60 | 0.02 |
| Low Temp Shift 2 | 8.35 | 0.96 | 0.75 | 0.87 | 34.00 | 1.00 | 30.80 | 0.52 | 24.85 | 1.00 | 10.35 | 0.23 |

FIG. 4B

Statistical comparison of day 14 titer and specific productivity between treatments groups and the control group

| Treatment | Mean Day 14 Titer (g/L) | Day 14 Titer Dunnett's Test p-Value | Qp (pg/cell-day) | Qp Dunnett's Test p-value |
|---|---|---|---|---|
| Control | 3.43 | N/A | 34.2 | N/A |
| High $CO_2$ | 3.44 | 1.00 | 36.7 | 0.98 |
| Late First Feed | 3.33 | 0.98 | 32.1 | 0.99 |
| Low Initial pH | 2.59 | <0.01 | 46.8 | 0.03 |

Statistical comparison of day 14 titer and specific productivity between treatments groups and the control group

| Treatment | Mean Day 14 Titer (g/L) | Day 14 Titer Dunnett's Test p-Value | Qp (pg/cell-day) | Qp Dunnett's Test p-value |
|---|---|---|---|---|
| Low Initial VCD | 1.57 | <0.01 | 39.4 | 0.59 |
| High Initial VCD | 3.30 | 0.93 | 29.0 | 0.57 |
| Low Overall Temperature | 2.87 | 0.02 | 38.5 | 0.76 |
| Early pH Shift Timing | 3.38 | 1.00 | 45.8 | 0.04 |
| Low Temp Shift 1 | 3.48 | 1.00 | 42.0 | 0.22 |
| Low Temp Shift 2 | 3.03 | 0.10 | 31.6 | 0.97 |

FIG. 4C

G0F (P2100) Glycoform relative abundance in day 14 pre-harvest samples

| Treatment Group | T5 | | | T7 | | |
|---|---|---|---|---|---|---|
| | G0F Mean Relative Abundance (%) | Percent Difference From Control (%) | Control Dunnett's p-value | G0F Mean Relative Abundance (%) | Percent Difference From Control (%) | Control Dunnett's p-value |
| Control | 6.1 | N/A | N/A | 5.2 | N/A | N/A |
| High pCO2 Shift | 6.3 | 3.3 | 1.00 | 5.2 | 0.0 | 1.00 |
| Late First Feed | 6.6 | 8.2 | 0.81 | 5.7 | 9.7 | 0.80 |
| Low Initial pH | 5.0 | -18.9 | 0.12 | 4.1 | -20.4 | 0.16 |
| Low Initial VCD | 4.7 | -23.0 | 0.05 | 4.1 | -21.4 | 0.14 |
| High Initial VCD | 7.1 | 16.4 | 0.21 | 6.2 | 20.4 | 0.16 |
| Low Overall Temp | 6.0 | -2.5 | 1.00 | 5.1 | -1.0 | 1.00 |
| Early pH Shift | 5.4 | -11.5 | 0.53 | 4.4 | -15.5 | 0.38 |
| Low Temp Shift 1 | 5.9 | -3.3 | 1.00 | 4.9 | -5.8 | 0.98 |
| Low Temp Shift 2 | 5.8 | -4.9 | 0.98 | 4.9 | -4.9 | 0.99 |

FIG. 4D

G2F (P2120) Glycoform relative abundance in day 14 harvest samples

| Treatment Group | T5 | | | T7 | | |
|---|---|---|---|---|---|---|
| | G2F Mean Relative Abundance (%) | Percent Difference From Control (%) | Control Dunnett's p-value | G2F Mean Relative Abundance (%) | Percent Difference From Control (%) | Control Dunnett's p-value |
| Control | 11.2 | N/A | N/A | 17.6 | N/A | N/A |
| High pCO2 Shift | 9.7 | -13.3 | 0.72 | 14.9 | -15.3 | 0.82 |
| Late First Feed | 9.3 | -18.1 | 0.51 | 14.3 | -19.0 | 0.65 |
| Low Initial pH | 7.0 | -38.5 | 0.03 | 10.2 | -42.3 | 0.06 |
| Low Initial VCD | 5.1 | -54.9 | <0.01 | 8.1 | -54.0 | 0.01 |
| High Initial VCD | 11.6 | 1.8 | 1.00 | 19.1 | 8.2 | 0.99 |
| Low Overall Temp | 7.2 | -36.7 | 0.04 | 10.5 | -40.6 | 0.07 |
| Early pH Shift | 8.1 | -28.8 | 0.12 | 11.8 | -33.0 | 0.17 |
| Low Temp Shift 1 | 8.7 | -23.5 | 0.26 | 13.1 | -25.9 | 0.36 |
| Low Temp Shift 2 | 10.2 | -8.4 | 0.94 | 15.9 | -9.7 | 0.98 |

FIG. 4E

S1G2F (P2121) glycoform relative abundance in day 14 harvest material

| Treatment Group | T5 S1G2F Mean Relative Abundance (%) | T5 Percent Difference From Control (%) | T5 Control Dunnett's p-value | T7 S1G2F Mean Relative Abundance (%) | T7 Percent Difference From Control (%) | T7 Control Dunnett's p-value |
|---|---|---|---|---|---|---|
| Control | 33.2 | N/A | N/A | 36.5 | N/A | N/A |
| High pCO2 Shift | 33.2 | 0 | 1.00 | 36.1 | -1.1 | 1.00 |
| Late First Feed | 33.7 | 1.4 | 1.00 | 36.5 | 0 | 1.00 |
| Low Initial pH | 37.7 | 13.4 | <0.01 | 36.1 | -1.2 | 0.99 |
| Low Initial VCD | 39.9 | 20.0 | <0.01 | 34.2 | -6.4 | 0.06 |
| High Initial VCD | 31.9 | -4.1 | 0.57 | 35.5 | -2.9 | 0.67 |
| Low Overall Temp | 37.0 | 11.3 | <0.01 | 35.7 | -2.2 | 0.86 |
| Early pH Shift | 36.0 | 8.13 | 0.54 | 37.2 | 1.9 | 0.92 |
| Low Temp Shift 1 | 34.5 | 3.9 | 0.60 | 36.7 | 0.4 | 1.00 |
| Low Temp Shift 2 | 34.4 | 3.6 | 0.71 | 36.2 | -0.8 | 1.00 |

FIG. 4F

S2G2F (P2122) glycoform relative abundance in day 14 harvest samples

| Treatment Group | T5 | | | T7 | | |
|---|---|---|---|---|---|---|
| | S2G2F Mean Relative Abundance (%) | Percent Difference From Control (%) | Control Dunnett's p-value | S2G2F Mean Relative Abundance (%) | Percent Difference From Control (%) | Control Dunnett's p-value |
| Control | 14.7 | N/A | N/A | 20.1 | N/A | N/A |
| High pCO2 Shift | 15.1 | 3.1 | 1.00 | 23.1 | 15.2 | 0.79 |
| Late First Feed | 15.3 | 4.1 | 1.00 | 22.8 | 13.5 | 0.86 |
| Low Initial pH | 17.7 | 20.5 | 0.11 | 29.0 | 44.6 | 0.03 |
| Low Initial VCD | 18.9 | 29.0 | 0.02 | 32.8 | 63.3 | <0.01 |
| High Initial VCD | 13.2 | -9.9 | 0.71 | 17.7 | -11.7 | 0.92 |
| Low Overall Temp | 16.3 | 10.9 | 0.62 | 28.3 | 40.9 | 0.05 |
| Early pH Shift | 16.4 | 11.9 | 0.54 | 26.8 | 33.4 | 0.13 |
| Low Temp Shift 1 | 16.0 | 9.2 | 0.77 | 25.0 | 24.7 | 0.35 |
| Low Temp Shift 2 | 15.5 | 5.8 | 0.97 | 21.9 | 9.2 | 0.98 |

FIG. 4G

S1G3F (P3131) Glycoform relative abundance in day 14 harvest samples

| | T5 | | | T7 | | |
|---|---|---|---|---|---|---|
| Treatment Group | S1G3F Mean Relative Abundance (%) | Percent Difference From Control (%) | Control Dunnett's p-value | S1G3F Mean Relative Abundance (%) | Percent Difference From Control (%) | Control Dunnett's p-value |
| Control | 5.2 | N/A | N/A | 2.4 | N/A | N/A |
| High pCO2 Shift | 4.5 | -12.6 | 0.71 | 2.0 | -14.9 | 0.84 |
| Late First Feed | 4.5 | -12.6 | 0.71 | 2.0 | -14.9 | 0.84 |
| Low Initial pH | 3.6 | -31.1 | 0.05 | 1.4 | -40.4 | 0.07 |
| Low Initial VCD | 3.4 | -35.0 | 0.025 | 1.2 | -51.1 | 0.02 |
| High Initial VCD | 5.3 | 2.9 | 1.00 | 2.7 | 12.8 | 0.91 |
| Low Overall Temp | 3.4 | -34.0 | 0.03 | 1.4 | -42.6 | 0.06 |
| Early pH Shift | 4.0 | -23.3 | 0.17 | 1.6 | -31.9 | 0.19 |
| Low Temp Shift 1 | 4.1 | -20.4 | 0.27 | 1.9 | -21.3 | 0.54 |
| Low Temp Shift 2 | 4.8 | -7.8 | 0.96 | 2.1 | -12.8 | 0.91 |

FIG. 4H

T5 S2G4F (P4142) glycoform relative abundance in day 14 harvest samples

| Treatment | T5 S2G4F Mean Relative Abundance (%) | Percent Difference From Control (%) | Control Dunnett's p-value |
|---|---|---|---|
| Control | 1.7 | N/A | N/A |
| High pCO2 Shift | 1.6 | -5.9 | 0.98 |
| Late First Feed | 1.6 | -5.9 | 0.98 |

T5 S2G4F (P4142) glycoform relative abundance in day 14 harvest samples

| Treatment | T5 S2G4F Mean Relative Abundance (%) | Percent Difference From Control (%) | Control Dunnett's p-value |
|---|---|---|---|
| Low Initial pH | 1.2 | -29.4 | 0.04 |
| Low Initial VCD | 1.1 | -35.3 | 0.01 |
| High Initial VCD | 1.7 | 0.0 | 1.00 |
| Low Overall Temp | 1.2 | -32.4 | 0.02 |
| Early pH Shift | 1.4 | -17.6 | 0.30 |
| Low Temp Shift 1 | 1.6 | -8.8 | 0.88 |
| Low Temp Shift 2 | 1.6 | -5.9 | 0.98 |

FIG. 5

Day 16 pre-harvest N-link, HMW, HCP, and rDNA

| Condition | N-link | | | | HMW (%) | HCP (x10$^5$ ng/mL) | rDNA (x10$^6$ pg/mL) |
|---|---|---|---|---|---|---|---|
| | Domain I (%) | Domain II (%) | Domain III (%) | Domain IV+V (%) | | | |
| 25 generations | 30.1±0.4 | 30.4±0.4 | 28.1[a] | 11.4±0.1 | 30.0±0.4 | 5.0±0.4 | 8.1±0.5 |
| 33 generations | 35.6±0.5 | 29.5±0.1 | 23.7±0.5 | 11.4±0.1 | 27.7±0.3 | 4.0±0.1 | 3.4±0.4 |
| 57 generations | 39±1 | 29.9±0.6 | 21±1 | 10±0.1 | 26.7±0.2 | 3.5±0.1 | 6±1 |
| 77 generations | 38.0±0.6 | 29.6±0.2 | 21.4±0.4 | 11.2±0.1 | 25±2 | 3.4±0.1 | 5±5[b] |
| 99 generations | 39±1 | 29.5±0.1 | 20.6±0.1 | 11.0±0.8 | 25.6±0.4 | 3.3[a] | 11.5±0.7 |

[a] Duplicate samples returned identical values

[b] Values are 8.4 x 10$^6$ and 1.0 x 10$^6$ pg/mL

Dunnett's test p-value results for Day 16 pre-harvest N-link, HMW, HCP and rDNA

| Condition | p-value | | | | | | |
|---|---|---|---|---|---|---|---|
| | N-link | | | | HMW | HCP | rDNA |
| | Domain I | Domain II | Domain III | Domain IV+V | | | |
| 33 generations | **0.0049** | 0.1301 | **0.0014** | 1.0000 | 0.9913 | **0.0069** | 0.2844 |
| 57 generations | **0.0005** | 0.4791 | **0.0001** | 0.0501 | 0.3805 | **0.0011** | 0.8851 |
| 77 generations | **0.0009** | 0.1811 | **0.0002** | 0.9544 | 0.0834 | **0.0009** | 0.5110 |
| 99 generations | **0.0005** | 0.1534 | **0.0001** | 0.7824 | **0.0398** | **0.0007** | 0.4898 |

FIG. 6A

Process parameters and characterization ranges for experimental design

| Parameter | Midpoint | Study Range |
|---|---|---|
| Inoculation VCD ($10^6$ cells/mL) | 0.3 | 0.20-0.50 |
| pH Shift Set Point[a] | 6.9 | 6.8-7.1 |
| $pCO_2$ Shift Set Point | 16.8 | 11.2-22.4 |
| First Temperature Set Point (°C | 36 | 35-37 |
| Second Temperature Set Point (°C) | 33 | 32-34 |
| Third Temperature Set Point (°C) | 31 | 30-32 |

[a] pH is controlled within ±0.02 units of the set point

FIG. 6B

Measured attribute values of the production bioreactor

| Attribute | Bioreactor ID | | | | | | | | | | | | | |
|---|---|---|---|---|---|---|---|---|---|---|---|---|---|---|
| | 180608 -01 | 180608 -02 | 180609 -03 | 180608 -04 | 180608 -05 | 180608 -11 | 180609 -12 | 180608 -14 | 180608 -15 | 180608 -16 | 180608 -21 | 180608 -22 | 180608 -24 | 180608 -31 |
| IVCD ($10^9$ cells-day/mL) | 0.03 | 0.15 | 0.14 | 0.04 | 0.05 | 0.02 | 0.08 | 0.09 | 0.04 | 0.06 | 0.04 | 0.10 | 0.14 | 0.11 |
| Final Viability (%) | 81.9 | 73.8 | 81.0 | 82.1 | 88.9 | 83.8 | 69.0 | 82.0 | 85.3 | 88.5 | 79.2 | 90.1 | 83.2 | 86.8 |
| Day 16 Titer (g/L) | 0.6 | 4.5 | 4.2 | 1.8 | 1.7 | 1.0 | 2.6 | 3.8 | 1.0 | 1.7 | 1.1 | 3.7 | 4.7 | 4.1 |
| Qp (pg/cell-day) | 22.4 | 28.8 | 31.3 | 33.8 | 33.0 | 26.1 | 30.8 | 42.7 | 24.1 | 30.0 | 28.2 | 35.8 | 33.6 | 38.6 |
| Day 10 NANA (MR) | 7.4 | 8.8 | 9.8 | 7.3 | 7.8 | 7.5 | 8.5 | 8 | 7.4 | 7.7 | 7.3 | 8.8 | 9.1 | 8.4 |
| Day 11 NANA (MR) | 7.5 | 9.5 | 9 | 7.5 | 8 | 7.6 | 8.4 | 8.2 | 8.1 | 8.3 | 7.7 | 8.9 | 8.8 | 8.3 |
| Day 12 NANA (MR) | 7.5 | 9.1 | 8.7 | 7.2 | 7.8 | 7.7 | 8.1 | 8.2 | 8 | 7.8 | 7.7 | 8.9 | 8.8 | 8.1 |
| Day 13 NANA (MR) | 7.1 | 8.4 | 8.3 | 7.1 | 7.9 | 7.7 | 7.7 | 7.9 | 7.8 | 7.7 | 7.5 | 8.7 | 8.5 | 7.6 |
| Day 14 NANA (MR) | 6.6 | 7.8 | 7.8 | 6.8 | 7.6 | 7.3 | 7.3 | 7.5 | 7.6 | 7.5 | 7.2 | 8.2 | 7.7 | 7.4 |
| Day 15 NANA (MR) | 6.3 | 7.3 | 7.7 | 6.7 | 7.3 | 6.9 | 6.7 | 7 | 6.9 | 6.9 | 6.7 | 7.9 | 7.3 | 6.9 |
| Day 16 NANA (MR) | 6.5 | 7.1 | 7.8 | 6.8 | 7.2 | 6.9 | 6.5 | 7.1 | 7.1 | 7.2 | 6.8 | 7.6 | 6.5 | 6.9 |
| Day 16 NGNA (MR) | 0.6 | 0.8 | 1.2 | 1.3 | 1.4 | 0.6 | 0.7 | 1.5 | 0.7 | 0.9 | 0.6 | 1.2 | 1 | 1 |
| N-link Domain I (%) | 39.4 | 41.3 | 34.6 | 37.5 | 34.6 | 38 | 39.9 | 36.1 | 37.2 | 38 | 38.8 | 35.5 | 40.2 | 38.7 |
| N-link Domain II (%) | 27.6 | 29.4 | 29.2 | 28.1 | 27.6 | 28.3 | 30.2 | 27.1 | 28.8 | 29.4 | 29.5 | 28.3 | 29.4 | 29.7 |
| N-link Domain III (%) | 22.8 | 19.5 | 22.7 | 23 | 24.2 | 23.8 | 21 | 23.4 | 23.5 | 22.7 | 2.7 | 23.3 | 20.2 | 21.7 |
| N-link Domain IV+V (%) | 8.5 | 7.6 | 10.4 | 9 | 10.3 | 7.6 | 7.2 | 10.4 | 8.5 | 7.6 | 7.2 | 10 | 8.1 | 7.8 |
| HMW (%) | 26.7 | 23.9 | 20.9 | 27.8 | 24.1 | 25.7 | 26.2 | 28.4 | 25.5 | 26 | 26.4 | 28 | 26.8 | 27.6 |
| HCP ($10^4$ ppm)[a] | 8.5 | 4 | 5 | 2.4 | 2.1 | 1.2 | 2.2 | 4 | 1.1 | 2.4 | 1.1 | 3.9 | 3.5 | 3.5 |
| DNA ($10^6$ ppb)[a] | 3.31 | 3.82 | 4.49 | 1.17 | 1.48 | 2.72 | 2.97 | 1.40 | 1.68 | 1.30 | 2.00 | 1.02 | 1.50 | 0.86 |

[a] Absolute concentration of impurity divided by titer

FIG. 6C

Measured attribute values of the production bioreactor (cont.)

| Attribute | Bioreactor ID | | | | | | | | |
|---|---|---|---|---|---|---|---|---|---|
| | 180608-32 | 180608-33 | 180609-34 | 180608-36 | 180609-404 | 180608-405 | 180609-406 | 180609-407 | 180609-408 |
| IVCD ($10^9$ cells-day/mL) | 0.05 | 0.06 | 0.09 | 0.13 | 0.12 | 0.11 | 0.12 | 0.12 | 0.14 |
| Final Viability (%) | 66.2 | 85.7 | 80.2 | 85.9 | 68.8 | 88.6 | 79.3 | 86.7 | N/A |
| Day 16 Titer (g/L) | 0.9 | 1.6 | 3.8 | 4.6 | 4.8 | 5.0 | 4.7 | 4.2 | 4.8 |
| Qp (pg/cell-day) | 17.5 | 28.0 | 43.7 | 35.4 | 38.7 | 43.1 | 38.0 | 35.3 | N/A[c] |
| Day 10 NANA (MR) | 6.8 | 7.8 | 8.1 | 8.8 | 9 | 8.3 | 8.6 | 8.9 | 9.6 |
| Day 11 NANA (MR) | 7.3 | 8.2 | 8.3 | 9.2 | 8.8 | 8.1 | 8.8 | 8.5 | 9.2 |
| Day 12 NANA (MR) | 7.1 | 7.9 | 8.3 | 8.8 | 8.6 | 8 | 8.8 | 8.5 | 9 |
| Day 13 NANA (MR) | 6.6 | 7.6 | 8 | 8.3 | 8.3 | 8 | 8.4 | 8.2 | 8.5 |
| Day 14 NANA (MR) | 6.1 | 7.4 | 7.8 | 8.1 | N/A | 7.7 | 7.9 | 7.8 | 7.8 |
| Day 15 NANA (MR) | 5.5 | 6.9 | 7.4 | 7.8 | 7.4 | 7.1 | 7.3 | 7.5 | 7.3 |
| Day 16 NANA (MR) | 5.7 | 7.1 | 7.1 | 7 | 7.1 | 6.9 | 7 | 7.3 | 6.9 |
| Day 16 NGNA (MR) | 0.4 | 0.8 | 1.5 | 1 | 0.8 | 1.3 | 1.1 | 1 | 1 |
| N-link Domain I (%) | 47.2 | N/A | 35.2 | 38.1 | 38.3 | 36.7 | 37.6 | 36.5 | 39 |
| N-link Domain II (%) | 27.4 | N/A | 27.3 | 30.3 | 30.6 | 28.9 | 29 | 29.5 | 29.4 |
| N-link Domain III (%) | 18.7 | N/A | 23.8 | 21.7 | 21.4 | 22.6 | 21.7 | 23.2 | 21.3 |
| N-link Domain IV+V (%) | 5.5 | N/A | 10.3 | 7.9 | 7.9 | 9.3 | 8.9 | 8.7 | 7.9 |
| HMW (%) | 26.7 | 27 | 27.7 | 26.5 | 24.9 | 28 | 27 | 27.4 | 25 |
| DNA ($10^6$ ppb)[a] | 8.6 | 1.9 | 4.4 | 3.4 | 4.3 | 4.5 | 4.2 | 3.5 | 3.7 |
| DNA ($10^6$ ppb)[a] | 7.15 | 2.13 | 1.20 | 1.22 | 2.06 | 1.02 | 1.75 | 1.00 | 1.76 |

[a] Absolute concentration of impurity divided by titer

FIG. 7

Summary of significant main effects

| Process Parameter | Response | |
|---|---|---|
| | Process Attribute | Quality Attribute |
| Inoculation VCD ($10^6$ cells/mL) | pVCD, day 16 titer, DNA | Day 8-14 NANA, Day 16 HCP, Day 16 DNA, T5_P2120, T5_P3131, T7_P2120, T7_P3131 |
| pH Shift Set Point | D5 Growth Rate, PVCD, day 16 titer, Qp | Day 13-16 NANA, day 16 NGNA, DNA, T5_P3131, T7_P2122, T7_P3131, N-link Domains V & IV+V |
| $pCO_2$ Shift Set Point | HMW, DNA | N/A |
| First Temperature Set Point (°C) | Day 16 titer, Qp, HMW, DNA | Day 11-12 &16 NANA, Day 16 NGNA |
| Second Temperature Set Point (°C) | DNA, Day 13-16 NANA, Day 16 NGNA, | N-link Domain V |
| Third Temperature Set Point (°C) | Day 16 titer, HMW | Day 8 NANA, day 12 NANA, day 8-12 NGNA |

FIG. 8A

Relative Abundance of Biantenary Glycans on T5 Glycopeptide

| Process | Sample | T5_P2100 | T5_P2110 | T5_P2120 | T5_P2111 | T5_P2121 | T5_P2122 | T5_P3131 | T5_P3132 | T5_P4142 | T5_NG |
|---|---|---|---|---|---|---|---|---|---|---|---|
| F | 551125 | 6.6 | 4.6 | 7.8 | 14.0 | 32.3 | 17.9 | 4.5 | 6.5 | 1.6 | 4.2 |
| F | 554526 | 6.4 | 4.1 | 6.3 | 15.1 | 31.3 | 20.0 | 4.0 | 6.9 | 1.6 | 4.1 |
| F | 554529 | 6.6 | 4.0 | 6.7 | 13.6 | 31.8 | 20.0 | 4.2 | 7.0 | 1.7 | 4.4 |
| F | AAV2291 | 5.9 | 5.3 | 10.5 | 12.6 | 33.0 | 15.5 | 4.9 | 6.2 | 1.7 | 4.5 |
| F | AAV2516 | 4.9 | 5.1 | 10.6 | 11.9 | 34.5 | 15.5 | 5.2 | 6.2 | 1.7 | 4.5 |
| F | AAV2805 | 5.1 | 5.1 | 10.6 | 12.6 | 33.1 | 15.4 | 5.4 | 6.0 | 1.8 | 4.8 |
| J | AAX7512 | 4.4 | 4.4 | 9.5 | 10.8 | 33.1 | 18.1 | 5.6 | 7.7 | 2.3 | 4.2 |
| J | AAZ4611 | 3.2 | 3.7 | 7.2 | 10.4 | 35.1 | 21.8 | 4.4 | 7.0 | 1.9 | 5.2 |
| J | AAZ7138 | 4.6 | 5.1 | 9.8 | 11.8 | 31.6 | 18.1 | 5.4 | 7.5 | 2.3 | 3.8 |
| J | AAZ9651 | 4.0 | 4.9 | 9.7 | 10.8 | 33.3 | 18.5 | 5.5 | 7.1 | 2.4 | 3.7 |
| J | ABA0706 | 3.2 | 4.3 | 7.2 | 11.8 | 32.7 | 22.9 | 4.4 | 7.7 | 2.1 | 3.7 |
| J | ABA2568 | 4.4 | 4.4 | 7.8 | 11.1 | 32.6 | 21.2 | 4.6 | 7.5 | 2.3 | 4.1 |
| F | RM1 | 3.7 | 4.1 | 10.4 | 11.4 | 36.5 | 16.3 | 5.3 | 6.1 | 1.4 | 4.9 |
| F | RM2 | 3.2 | 4.0 | 9.7 | 11.1 | 34.8 | 18.3 | 5.5 | 6.9 | 2.1 | 4.4 |
| F | Range | 3.2 - 6.6 | 4.0 - 5.3 | 6.3 - 10.6 | 11.1 - 15.1 | 31.3 - 36.5 | 15.4 - 20.0 | 4.0 - 5.5 | 6.0 - 7.0 | 1.4 - 2.1 | 4.1 - 4.9 |
| J | Range | 3.2 - 4.6 | 3.7 - 5.1 | 7.2 - 9.8 | 10.4 - 11.8 | 31.6 - 35.1 | 18.1 - 22.9 | 4.4 - 5.6 | 7.0 - 7.7 | 1.9 - 2.4 | 3.7 - 5.2 |

FIG. 9A

Relative Abundance of Biantenary Glycans on T7 Glycopeptide

| Process | Sample | T7_P2100 | T7_P2110 | T7_P2120 | T7_P2111 | T7_P2121 | T7_P2122 | T7_P3131 | T7_P3132 | T7_P3133 | T7_P2121_Gal | T7_P2120_Gal | T7_Man5 |
|---|---|---|---|---|---|---|---|---|---|---|---|---|---|
| F | 551125 | 3.5 | 3.5 | 10.0 | 10.3 | 37.3 | 29.0 | 1.2 | 2.1 | 1.1 | 1.5 | 0.5 | 0.0 |
| F | 554526 | 3.4 | 3.3 | 9.0 | 11.3 | 35.3 | 31.0 | 1.2 | 2.3 | 1.4 | 1.5 | 0.4 | 0.0 |
| F | 554529 | 3.5 | 2.9 | 8.0 | 10.5 | 35.2 | 32.6 | 1.1 | 2.3 | 1.5 | 1.8 | 0.5 | 0.0 |
| F | AAV2291 | 3.4 | 4.0 | 15.1 | 7.1 | 39.1 | 24.3 | 1.5 | 2.2 | 0.9 | 1.5 | 0.8 | 0.0 |
| F | AAV2516 | 2.7 | 3.9 | 18.0 | 6.2 | 40.3 | 21.5 | 1.9 | 2.2 | 0.8 | 1.5 | 0.9 | 0.0 |
| F | AAV2805 | 2.8 | 4.2 | 18.6 | 6.4 | 39.9 | 20.8 | 1.9 | 2.3 | 0.7 | 1.4 | 0.9 | 0.0 |
| J | AAX7512 | 3.5 | 3.6 | 11.2 | 6.0 | 37.7 | 27.2 | 2.0 | 3.4 | 1.6 | 2.6 | 1.0 | 0.1 |
| J | AAZ4611 | 2.1 | 2.7 | 8.2 | 5.3 | 35.9 | 33.8 | 1.4 | 2.7 | 1.8 | 4.7 | 1.1 | 0.2 |
| J | AAZ7138 | 4.0 | 4.9 | 13.9 | 6.6 | 36.5 | 23.5 | 2.2 | 3.3 | 1.6 | 2.3 | 1.2 | 0.1 |
| J | AAZ9651 | 3.4 | 4.9 | 14.1 | 6.6 | 37.0 | 23.2 | 2.2 | 3.1 | 1.5 | 2.7 | 1.3 | 0.1 |
| J | ABA0706 | 2.5 | 3.8 | 10.1 | 6.3 | 36.4 | 30.2 | 1.7 | 3.1 | 2.0 | 2.8 | 1.0 | 0.1 |
| J | ABA2568 | 4.0 | 5.0 | 12.4 | 7.1 | 34.2 | 25.9 | 1.9 | 3.1 | 1.8 | 3.1 | 1.4 | 0.1 |
| F | RM1 | 1.8 | 2.9 | 17.8 | 4.9 | 42.3 | 23.4 | 1.8 | 2.2 | 0.6 | 1.5 | 0.8 | 0.0 |
| F | RM2 | 1.9 | 3.0 | 18.0 | 4.9 | 40.4 | 23.8 | 1.9 | 2.6 | 1.0 | 1.6 | 0.9 | 0.0 |
| F | Range | 1.8 - 3.5 | 2.9 - 4.2 | 8.0 - 18.6 | 4.9 - 11.3 | 35.2 - 42.3 | 20.8 - 32.6 | 1.1 - 1.9 | 2.1 - 2.6 | 0.6 - 1.5 | 1.4 - 1.8 | 0.4 - 0.9 | 0.0 - 0.0 |
| J | Range | 2.1 - 4.0 | 2.7 - 5.0 | 8.2 - 14.1 | 5.3 - 7.1 | 34.2 - 37.7 | 23.2 - 33.8 | 1.4 - 2.2 | 2.7 - 3.4 | 1.5 - 2.0 | 2.3 - 4.7 | 1.0 - 1.4 | 0.1 - 0.2 |

Statistical Comparison of N-Linked Domain I Test Results from Process F and Process J Lots

N-Linked Domain I (Area %)

Process J lots were within the tolerance limits defined by Process F Lots

Mean and Standard Deviations

| Process | Number | Mean | STD | Min | Max |
|---|---|---|---|---|---|
| F | 517 | 32 | 1.68 | 28 | 37 |
| J | 5 | 31 | 1.22 | 29 | 32 |

Tolerance Limits (TL)

| Process | Lower TL | Upper TL |
|---|---|---|
| F | 28 | 37 |

Statistical Comparison of N-Linked Domain II Test Results from Process F and Process J Lots

N-Linked Domain II (Area %)

Process J lots were within the tolerance limits defined by Process F Lots

Mean and Standard Deviations

| Process | Number | Mean | STD | Min | Max |
|---|---|---|---|---|---|
| F | 517 | 30 | 1.21 | 27 | 33 |
| J | 5 | 27 | 0.71 | 26 | 28 |

Tolerance Limits (TL)

| Process | Lower TL | Upper TL |
|---|---|---|
| F | 27 | 33 |

Statistical Comparison of N-Linked Domain III Test Results from Process F and Process J Lots

N-Linked Domain III (Area %)

Process J lots were within the tolerance limits defined by Process F Lots

Mean and Standard Deviations

| Process | Number | Mean | STD | Min | Max |
|---|---|---|---|---|---|
| F | 517 | 26 | 1.34 | 22 | 31 |
| J | 5 | 27.4 | 0.548 | 27 | 28 |

Tolerance Limits (TL)

| Process | Lower TL | Upper TL |
|---|---|---|
| F | 22 | 31 |

Statistical Comparison of N-Linked Domain IV + V Test Results from Process F and Process J Lots

N-Linked Domain IV + V (Area %)

Process J lots were within the tolerance limits defined by Process F Lots

Mean and Standard Deviations

| Process | Number | Mean | STD | Mi n | Ma x |
|---|---|---|---|---|---|
| F | 517 | 12 | 1.36 | 8 | 16 |
| J | 5 | 14.6 | 1.342 | 13 | 16 |

Tolerance Limits (TL)

| Process | Lower TL | Upper TL |
|---|---|---|
| F | N/A | ≤ 16 |

Statistical Comparison of NANA Test Results from Process F and Process J Lots

NANA (Mole/mole protein)

Process J lots were within the tolerance limits defined by Process F Lots

Mean and Standard Deviations

| Process | Number | Mean | STD | Min | Max |
|---|---|---|---|---|---|
| F | 519 | 9.3 | 0.418 | 8.3 | 11 |
| J | 5 | 10.0 | 0.23 | 9.5 | 10.1 |

Tolerance Limits (TL)

| Process | Lower TL | Upper TL |
|---|---|---|
| F | 8.3 | 11 |

Statistical Comparison of NGNA Test Results from Process F and Process J Lots

NGNA (Mole/mole protein)

Process J lots were within the tolerance limits defined by Process F Lots

Mean and Standard Deviations

| Process | Number | Mean | STD | Min | Max |
|---|---|---|---|---|---|
| F | 519 | 0.8 | 0.154 | 0.3 | 1.2 |
| J | 5 | 1.0 | 0.13 | 0.9 | 1.2 |

Tolerance Limits (TL)

| Process | Lower TL | Upper TL |
|---|---|---|
| F | N/A | ≤ 1.2 |

SEQUENCE LISTING

```
<160> NUMBER OF SEQ ID NOS: 11

<210> SEQ ID NO 1
<211> LENGTH: 124
<212> TYPE: PRT
<213> ORGANISM: Artificial Sequence
<220> FEATURE:
<223> OTHER INFORMATION: CTLA4 Extracellular Domain

<400> SEQUENCE: 1

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 2
<211> LENGTH: 383
<212> TYPE: PRT
<213> ORGANISM: Artificial Sequence
<220> FEATURE:
<223> OTHER INFORMATION: CTLA4-Ig amino acid sequence

<400> SEQUENCE: 2

Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45
```

```
Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380


<210> SEQ ID NO 3
<211> LENGTH: 359
<212> TYPE: PRT
<213> ORGANISM: Artificial Sequence
<220> FEATURE:
<223> OTHER INFORMATION: amino acids 25-383 of SEQ ID NO:2

<400> SEQUENCE: 3

Met Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30
```

```
Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Gln Glu
        115                 120                 125

Pro Lys Ser Ser Asp Lys Thr His Thr Ser Pro Pro Ser Pro Ala Pro
    130                 135                 140

Glu Leu Leu Gly Gly Ser Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355
```

```
<210> SEQ ID NO 4
<211> LENGTH: 358
<212> TYPE: PRT
<213> ORGANISM: Artificial Sequence
<220> FEATURE:
<223> OTHER INFORMATION: Amino Acids 26-383 of SEQ ID NO:2

<400> SEQUENCE: 4

Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30
```

-continued

Val Arg Val Thr Val Leu Arg Gln Ala Asp Ser Gln Val Thr Glu Val
35 40 45

Cys Ala Ala Thr Tyr Met Met Gly Asn Glu Leu Thr Phe Leu Asp Asp
50 55 60

Ser Ile Cys Thr Gly Thr Ser Ser Gly Asn Gln Val Asn Leu Thr Ile
65 70 75 80

Gln Gly Leu Arg Ala Met Asp Thr Gly Leu Tyr Ile Cys Lys Val Glu
85 90 95

Leu Met Tyr Pro Pro Pro Tyr Tyr Leu Gly Ile Gly Asn Gly Thr Gln
100 105 110

Ile Tyr Val Ile Asp Pro Glu Pro Cys Pro Asp Ser Asp Gln Glu Pro
115 120 125

Lys Ser Ser Asp Lys Thr His Thr Ser Pro Pro Ser Pro Ala Pro Glu
130 135 140

Leu Leu Gly Gly Ser Ser Val Phe Leu Phe Pro Pro Lys Pro Lys Asp
145 150 155 160

Thr Leu Met Ile Ser Arg Thr Pro Glu Val Thr Cys Val Val Val Asp
165 170 175

Val Ser His Glu Asp Pro Glu Val Lys Phe Asn Trp Tyr Val Asp Gly
180 185 190

Val Glu Val His Asn Ala Lys Thr Lys Pro Arg Glu Glu Gln Tyr Asn
195 200 205

Ser Thr Tyr Arg Val Val Ser Val Leu Thr Val Leu His Gln Asp Trp
210 215 220

Leu Asn Gly Lys Glu Tyr Lys Cys Lys Val Ser Asn Lys Ala Leu Pro
225 230 235 240

Ala Pro Ile Glu Lys Thr Ile Ser Lys Ala Lys Gly Gln Pro Arg Glu
245 250 255

Pro Gln Val Tyr Thr Leu Pro Pro Ser Arg Asp Glu Leu Thr Lys Asn
260 265 270

Gln Val Ser Leu Thr Cys Leu Val Lys Gly Phe Tyr Pro Ser Asp Ile
275 280 285

Ala Val Glu Trp Glu Ser Asn Gly Gln Pro Glu Asn Asn Tyr Lys Thr
290 295 300

Thr Pro Pro Val Leu Asp Ser Asp Gly Ser Phe Phe Leu Tyr Ser Lys
305 310 315 320

Leu Thr Val Asp Lys Ser Arg Trp Gln Gln Gly Asn Val Phe Ser Cys
325 330 335

Ser Val Met His Glu Ala Leu His Asn His Tyr Thr Gln Lys Ser Leu
340 345 350

Ser Leu Ser Pro Gly Lys
355

<210> SEQ ID NO 5
<211> LENGTH: 357
<212> TYPE: PRT
<213> ORGANISM: Artificial Sequence
<220> FEATURE:
<223> OTHER INFORMATION: Amino Acids 27-383 of SEQ ID NO:2

<400> SEQUENCE: 5

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

```
Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355


<210> SEQ ID NO 6
<211> LENGTH: 358
<212> TYPE: PRT
<213> ORGANISM: Artificial Sequence
<220> FEATURE:
<223> OTHER INFORMATION: Amino Acids 25-382 of SEQ ID NO:2

<400> SEQUENCE: 6

Met Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30
```

```
Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Cys Pro Asp Ser Asp Gln Glu
        115                 120                 125

Pro Lys Ser Ser Asp Lys Thr His Thr Ser Pro Pro Ser Pro Ala Pro
    130                 135                 140

Glu Leu Leu Gly Gly Ser Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Asp Glu Leu Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly
        355
```

<210> SEQ ID NO 7
<211> LENGTH: 357
<212> TYPE: PRT
<213> ORGANISM: Artificial Sequence
<220> FEATURE:
<223> OTHER INFORMATION: Amino Acids 26-382 of SEQ ID NO:2

<400> SEQUENCE: 7

```
Ala Met His Val Ala Gln Pro Ala Val Val Leu Ala Ser Ser Arg Gly
1               5                   10                  15

Ile Ala Ser Phe Val Cys Glu Tyr Ala Ser Pro Gly Lys Ala Thr Glu
            20                  25                  30
```

```
Val Arg Val Thr Val Leu Arg Gln Ala Asp Ser Gln Val Thr Glu Val
        35                  40                  45

Cys Ala Ala Thr Tyr Met Met Gly Asn Glu Leu Thr Phe Leu Asp Asp
    50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp Gln Glu Pro
        115                 120                 125

Lys Ser Ser Asp Lys Thr His Thr Ser Pro Pro Ser Pro Ala Pro Glu
    130                 135                 140

Leu Leu Gly Gly Ser Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270

Gln Val Ser Leu Thr Cys Leu Val Lys Gly Phe Tyr Pro Ser Asp Ile
        275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly
        355
```

<210> SEQ ID NO 8
<211> LENGTH: 356
<212> TYPE: PRT
<213> ORGANISM: Artificial Sequence
<220> FEATURE:
<223> OTHER INFORMATION: Amino acids 27-382 of SEQ ID NO:2

<400> SEQUENCE: 8

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30
```

-continued

```
Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly
        355


<210> SEQ ID NO 9
<211> LENGTH: 26
<212> TYPE: PRT
<213> ORGANISM: Artificial Sequence
<220> FEATURE:
<223> OTHER INFORMATION: T5

<400> SEQUENCE: 9

Leu Thr Phe Leu Asp Asp Ser Ile Cys Thr Gly Thr Ser Ser Gly Asn
1               5                   10                  15

Gln Val Asn Leu Thr Ile Gln Gly Leu Arg
            20                  25
```

-continued

```
<210> SEQ ID NO 10
<211> LENGTH: 35
<212> TYPE: PRT
<213> ORGANISM: Artificial Sequence
<220> FEATURE:
<223> OTHER INFORMATION: T7

<400> SEQUENCE: 10

Val Glu Leu Met Tyr Pro Pro Pro Tyr Tyr Glu Gly Ile Gly Asn Gly
1               5                   10                  15

Thr Gln Ile Tyr Val Ile Asp Pro Glu Pro Cys Pro Asp Ser Asp Gln
            20                  25                  30

Glu Pro Lys
        35


<210> SEQ ID NO 11
<211> LENGTH: 9
<212> TYPE: PRT
<213> ORGANISM: Artificial Sequence
<220> FEATURE:
<223> OTHER INFORMATION: T14

<400> SEQUENCE: 11

Glu Glu Gln Tyr Asn Ser Thr Tyr Arg
1               5
```

MANUFACTURING PROCESS FOR PROTEIN

CROSS-REFERENCE TO RELATED APPLICATIONS

This application claims priority benefit of U.S. Provisional Application No. 63/066,122, filed Aug. 14, 2020, which is herein incorporated by reference in its entirety.

REFERENCE TO SEQUENCE LISTING SUBMITTED ELECTRONICALLY VIA EFS-WEB

The content of the electronically submitted sequence listing in ASCII text file (Name 3338_188PC01_Seqlisting_ST25.txt; Size: 24,720 bytes; and Date of Creating: Aug. 12, 2021), filed with the application, is incorporated herein by reference in its entirety.

BACKGROUND OF THE DISCLOSURE

The market for protein therapeutics has grown significantly and the pace of development continues to increase. It is a challenge, however, for the industry to maintain the desired quality attributes, e.g., glycosylation, while maintaining the quantity, reducing the cost of production, and providing production flexibility. Efficient manufacturing scale production of protein therapeutics is required to continue to meet the needs of the market.

Glycosylation is one of the most abundant of all protein post-translational modifications (PTMs). It results from the addition of sugar residues to protein sidechains to form a glycoprotein. Mammalian glycoprotein oligosaccharides are commonly built from a limited number of monosaccharides but their structural diversity is vast, mainly because they often form complex branching patterns.

Glycosylation plays an important role in many specific biological functions, including immune defense, fertilization, viral replication, parasitic infection, cell growth, inflammation, and cell-cell adhesion. For pharmaceutical glycoproteins, glycosylation affects stability of protein conformation, clearance rate, protection from proteolysis, and improves protein solubility. Since different glycoforms have the potential to have different biological properties, the ability to monitor and control glycosylation during production is critical to the quality of a biopharmaceutical molecule.

However, glycosylation during fermentation naturally occurs with a certain degree of heterogeneity and can be affected by many different factors, such as the expression system, process conditions, media composition, feed protocols, purification process, or any combination thereof. Consequently, there are needs to improve the protein manufacturing process including culturing, while maintaining the glycosylation pattern of the protein consistent.

SUMMARY OF THE DISCLOSURE

The present disclosure is related to a method of improving the yield of a protein by cells, comprising culturing the cells in a bioreactor for a protein induction phase under suitable conditions, wherein the suitable conditions comprise an initial temperature set point of 36° C., a second temperature set point of 33° C., and a third temperature set point of 31° C.; an initial pH set point of 7.0 and a second pH set point of 6.9; an initial viable cell density (VCD) set point between $0.15\times10^6$ cells/mL and $0.45\times10^6$ cells/mL, e.g., $0.30\times10^6$ cells/mL; an initial pH of 6.9; an initial $CO_2$ set point between 10% to 40%; or any combination thereof. In some aspects, the suitable conditions comprise an initial temperature set point of 36° C., a second temperature set point of 33° C., and a third temperature set point of 31° C.; an initial pH set point of 7.0 and a second pH set point of 6.9; an initial viable cell density (VCD) set point of $0.30\times10^6$; and an initial $CO_2$ set point between 15% and 25%.

The present disclosure is related to a method of controlling cell growth rate, cell viability, viable cell density and/or titer of cells for producing a protein comprising culturing the cells in a bioreactor for a protein induction phase under an initial temperature set point of 36° C. and culturing the cell in a second temperature set point of 33° C. and a final temperature set point of 31° C.

The present disclosure is also related to a method of improving the yield of a protein by cells, comprising culturing the cells in a bioreactor under suitable conditions, wherein the suitable conditions comprise (i) an initial temperature set point of 36.0° C. and a second temperature set point lower than 36.0° C.; (ii) an initial temperature set point lower than 36.5° C. and a final temperature set point of 31.0° C.; or (iii) an initial temperature set point lower than 36.5° C., a second temperature set point of 33.0° C., and a final temperature set point lower than 33.0° C.

In some aspects, the final temperature set point occurs at about 228 to about 252 hours. In some aspects, the final temperature set point occurs at about 228 hours, about 234 hours, about 240 hours, about 246 hours, or about 252 hours after the initial temperature set point. In some aspects, the final temperature set point is 31.0° C. and occurs after 240 hours. In some aspects, the second temperature set point occurs at about 120 hours to about 168 hours. In some aspects, the second temperature set point occurs at about 120 hours, about 126 hours, about 132 hours, about 138 hours, about 144 hours, about 150 hours, about 156 hours, about 162 hours, or about 168 hours. In some aspects, the second temperature set point is 33.0° C. after 144 hours.

In some aspects, the conditions improve the protein yield by at least 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, or at least about 400%; as compared to a method without the suitable conditions. In some aspects, the method reduces cell growth rate. In some aspects, the cell growth exhibits a mean 0-5 day doubling time of from about 30.0 hours to about 40.0 hours. In some aspects, the cell growth exhibits a mean 0-5 day doubling time of about 35.1 hours.

In some aspects, the method controls a cell viability. In some aspects, the cell viability exhibits a mean peak viable cell density (VCD) of from about $10.0\times10^6$ cells/mL to about $15.0\times10^6$ cells/mL. In some aspects, the cell viability exhibits a mean peak viable cell density (VCD) of about $11.2\times10^6$ cells/mL. In some aspects, the cell viability exhibits a mean 0-14 day integral of viable cell density (IVCD) of from about $0.05\times10^9$ cells/mL to about $0.11\times10^9$ cells/mL. In some aspects, the cell viability exhibits a mean 0-14 day integral of viable cell density (IVCD) of about $0.10\times10^9$ cells/mL. In some aspects, the method controls a titer. In some aspects, the titer exhibits a mean day 14 titer of about 1.50 g/L to about 3.5 g/L. In some aspects, the titer exhibits a mean day 14 titer of about 2.87 g/L. In some aspects, the titer exhibits a mean specific productivity of from about 20.0 pg/cell-day to about 40.0 pg/cell-day. In some aspects, the titer exhibits a mean specific productivity of about 38.5 pg/cell-day. In some aspects, the process further comprises modifying an upstream bioreactor parameter, wherein the upstream reactor parameter is selected from the group consisting of (i) a feed time, (ii) an initial pH, (iii) a pH shift, (iv) a $CO_2$, (v) an initial cell density, or (vi) any combination thereof.

In some aspects, the method controls a glycosylation profile of the protein. In some aspects, the glycosylation profile comprises one or more N-linked glycans. In some aspects, the N-linked glycans comprise: G0F, G1F, G2F, S1G1F, S1G2F, and/or S2G2F. In some aspects, the methods further comprise measuring the glycosylation profile after day 14. In some aspects, the protein comprises a CTLA4 domain. In some aspects, the protein is a fusion protein. In some aspects, the fusion protein comprises an Fc portion. In some aspects, the protein is abatacept. In some aspects, the protein is an amino acid sequence as set forth in SEQ ID NO: 5. In some aspects, the one or more N-linked glycans are located at one or more residues selected from the group consisting of Asn76 (T5), Asn108 (T7), and/or Asn207 (T14) of abatacept. In some aspects, G0F comprises a relative abundance of less than or equal to about 7.0% or about 6.5%. In some aspects, G1F comprises a relative abundance of less than or equal to about 7.5% or of about 7%. In some aspects, G2F comprises a relative abundance of less than or equal to about 25% or of about 1.5% to about 23%. In some aspects, S1G1F comprises a relative abundance of less than or equal to about 13.5% or of about 12.5%. In some aspects, S1G2F comprises a relative abundance of more than or equal to about 33% or of about 32% to about 49%. In some aspects, S2G2F comprises a relative abundance of more than or equal to about 12% or of about 14% to about 48.5%. In some aspects, G2F comprises a relative abundance of about 1.5% to about 23%, S1G2F comprises a relative abundance of about 32% to about 49%, and/or S2G2F comprises a relative abundance of about 14% to about 48.5%. In some aspects, G2F comprises a relative abundance of less than or equal to about 25%, S1G2F comprises a relative abundance of more than or equal to about 33%, and/or S2G2F comprises a relative abundance of more than or equal to about 12%. In some aspects, G0F comprises a relative abundance of less than or equal to about 6.5%, G1F comprises a relative abundance of less than or equal to about 7%, G2F comprises a relative abundance of about 1.5% to about 23%, S1G1F comprises a relative abundance of less than or equal to about 12.5%, S1G2F comprises a relative abundance of about 32% to about 49%, and/or S2G2F comprises a relative abundance of about 14% to about 48.5%. In some aspects, G0F comprises a relative abundance of less than or equal to about 7.0%. In some aspects, G1F comprises a relative abundance of less than or equal to about 7.5%, G2F comprises a relative abundance of less than or equal to about 25%, S1G1F comprises a relative abundance of less than or equal to about 13.5%, S1G2F comprises a relative abundance of more than or equal to about 33%, and/or S2G2F comprises a relative abundance of more than or equal to about 12%.

In some aspects, the one or more N-linked glycans are located at residue Asn76 (T5) and comprise a relative abundance of G0F between about 2.0% and about 10.0%. In some aspects, the one or more N-linked glycans are located at residue Asn76 (T5) and comprise a relative abundance of G0F between about 2.5% and about 10%, about 2.5%, about 9.5%, about 2.5% and about 9%, about 2.5% and about 8.5%, about 2.5% and about 8%, about 2.5% and about 7.5%, about 2.5% and about 7%, about 2.5% and about 6.5%, about 3.0% and about 10%, about 3.0%, about 9.5%, about 3.0% and about 9%, about 3.0% and about 8.5%, about 3.0% and about 8%, about 3.0% and about 7.5%, about 3.0% and about 7%, or about 3.0% and about 6.5%. In some aspects, the one or more N-linked glycans are located at residue Asn76 (T5) and comprise a relative abundance of G0F between about 3.2% and 6.6%, between about 3.2% and about 4.6%, or between 3.2% and about 6.6%. In some aspects, the relative abundance of G0F is about 4.0%.

In some aspects, the one or more N-linked glycans are located at residue Asn108 (T7) and comprise a relative abundance of G0F between about 1.0% and about 6%. In some aspects, the one or more N-linked glycans are located at residue Asn108 (T7) and comprise a relative abundance of G0F between about 1.0% and about 6%, about 1.0% and about 5.5%, about 1.0% and about 5.0%, about 1.0% and about 4.5%, about 1.0% and about 4.0%, about 1.5% and about 6%, about 1.5% and about 5.5%, about 1.5% and about 5.0%, about 1.5% and about 4.5%, about 1.5% and about 4.0%, about 2.0% and about 6%, about 2.0% and about 5.5%, about 2.0% and about 5.0%, about 2.0% and about 4.5%, or about 2.0% and about 4.0%. In some aspects, the one or more N-linked glycans are located at residue Asn108 (T7) and comprise a relative abundance of G0F between about 2.1% and about 4.0%, between about 1.8% and about 3.5%, or between about 1.8% and 4.0%. In some aspects, the relative abundance of G0F is about 3.4%.

In some aspects, the one or more N-linked glycans are located at residue Asn76 (T5) and comprise a relative abundance of G2F between about 5% and about 12%. In some aspects, the one or more N-linked glycans are located at residue Asn76 (T5) and comprise a relative abundance of G2F between about 5% and about 12%, about 5% and about 11.5%, about 5% and about 11%, about 5% and about 10.5%, about 5% and about 10%, about 5.5% and about 12%, about 5.5% and about 11.5%, about 5.5% and about 11%, about 5.5% and about 10.5%, about 5.5% and about 10%, about 6% and about 12%, about 6% and about 11.5%, about 6% and about 11%, about 6% and about 10.5%, about 6% and about 10%, about 6.5% and about 12%, about 6.5% and about 11.5%, about 6.5% and about 11%, about 6.5% and about 10.5%, about 6.5% and about 10%, about 7% and about 12%, about 7% and about 11.5%, about 7% and about 11%, about 7% and about 10.5%, or about 7% and about 10%. In some aspects, the one or more N-linked glycans are located at residue Asn76 (T5) and comprise a relative abundance of G2F between about 7.2% and about 9.8%, between about 6.3% and 10.6%, or about 7.2% and about 10.6%. In some aspects, the relative abundance of G2F is about 7.8%.

In some aspects, the one or more N-linked glycans are located at residue Asn108 (T7) and comprise a relative abundance of G2F between about 5% and about 21%. In some aspects, the one or more N-linked glycans are located at residue Asn108 (T7) and comprise a relative abundance of G2F between about 5% and about 21%, about 5% and about 20.5%, about 5% and about 20%, about 5% and about 19.5%, about 5% and about 19%, about 5.5% and about 21%, about 5.5% and about 20.5%, about 5.5% and about 20%, about 5.5% and about 19.5%, about 5.5% and about 19%, about 6% and about 21%, about 6% and about 20.5%, about 6% and about 20%, about 6% and about 19.5%, about 6% and about 19%, about 6.5% and about 21%, about 6.5% and about 20.5%, about 6.5% and about 20%, about 6.5% and about 19.5%, about 6.5% and about 19%, about 7% and about 21%, about 7% and about 20.5%, about 7% and about 20%, about 7% and about 19.5%, about 7% and about 19%, about 7.5% and about 21%, about 7.5% and about 20.5%, about 7.5% and about 20%, about 7.5% and about 19.5%, about 7.5% and about 19%, about 8% and about 21%, about 8% and about 20.5%, about 8% and about 20%, about 8% and about 19.5%, or about 8% and about 19%. In some aspects, the one or more N-linked glycans are located at residue Asn108 (T7) and comprise a relative abundance of G2F between about 8.2% and about 14.1%, about 8.0% and about 18.6%, or about 8.2% and about 14.1%. In some aspects, the relative abundance of G2F is about 12.4%. In some aspects, G2F further comprises a galactose-alpha-1,3-galactose moiety (G2F-Gal), wherein the G2F-Gal comprise a relative abundance of less than or equal to about 1.4%. In some aspects, G2F-Gal comprises a relative abundance of between about 1.0% to about 1.4%. In some aspects, G2F-Gal comprises a relative abundance of between about 0.4% to about 0.9%.

In some aspects, the one or more N-linked glycans are located at residue Asn76 (T5) and comprise a relative abundance of S1G2F between about 29% and about 38%. In some aspects, the one or more N-linked glycans are located at residue Asn76 (T5) and comprise a relative abundance of S1G2F between about 29% and about 38%, about 29% and about 37.5%, about 29% and about 37%, about 29% and about 36.5%, about 29.5% and about 38%, about 29.5% and about 37.5%, about 29.5% and about 37%, about 29.5% and about 36.5%, about 30% and about 38%, about 30% and about 37.5%, about 30% and about 37%, about 30% and about 36.5%, about 31.5% and about 38%, about 31.5% and about 37.5%, about 31.5% and about 37%, about 31.5% and about 36.5%. In some aspects, the one or more N-linked glycans are located at residue Asn76 (T5) and comprise a relative abundance of S1G2F between about 31.6% and about 35.1%, about 31.3% and about 36.5%, or about 31.3% and about 36.5%. In some aspects, the relative abundance of S1G2F is about 33.3%.

In some aspects, the one or more N-linked glycans are located at residue Asn108 (T7) and comprise a relative abundance of S1G2F between 33% and about 45%. In some aspects, the one or more N-linked glycans are located at residue Asn108 (T7) and comprise a relative abundance of S1G2F between about 33% and about 45%, about 33% and about 44.5%, about 33% and about 44%, about 33% and about 43.5%, about 33% and about 43%, about 33% and about 42.5%, about 33.5% and about 45%, about 33.5% and about 44.5%, about 33.5% and about 44%, about 33.5% and about 43.5%, about 33.5% and about 43%, about 33.5% and about 42.5%, about 34% and about 45%, about 34% and about 44.5%, about 34% and about 44%, about 34% and about 43.5%, about 34% and about 43%, about 34% and about 42.5%, about 34.5% and about 45%, about 34.5% and about 44.5%, about 34.5% and about 44%, about 34.5% and about 43.5%, about 34.5% and about 43%, or about 34.5% and about 42.5%. In some aspects, the one or more N-linked glycans are located at residue Asn108 (T7) and comprise a relative abundance of S1G2F between about 34.2% and about 37.7%, about 35.5% and about 42.3%, or about 34.2% and about 42.3%. In some aspects, the relative abundance of S1G2F is about 36.5%. In some aspects, S1G2F further comprises a galactose-alpha-1,3-galactose moiety (S1G2F-Gal), wherein the S1G2F-Gal comprise a relative abundance of less than or equal to about 4.7%. In some aspects, the S1G2F-Gal comprises a relative abundance of between about 2.3% to about 4.7%. In some aspects, wherein the S1G2F-Gal comprises a relative abundance of between about 1.4% to about 1.8%.

In some aspects, the one or more N-linked glycans are located at residue Asn76 (T5) and comprise a relative abundance of S2G2F between about 13% and about 25%. In some aspects, the one or more N-linked glycans are located at residue Asn76 (T5) and comprise a relative abundance of S2G2F between about 13% and about 25%, about 13% and about 24.5%, about 13% and about 24%, about 13% and about 23.5%, about 13% and about 23%, about 13.5% and about 25%, about 13.5% and about 24.5%, about 13.5% and about 24%, about 13.5% and about 23.5%, about 13.5% and about 23%, about 14% and about 25%, about 14% and about 24.5%, about 14% and about 24%, about 14% and about 23.5%, about 14% and about 23%, about 14.5% and about 25%, about 14.5% and about 24.5%, about 14.5% and about 24%, about 14.5% and about 23.5%, about 14.5% and about 23%, about 15% and about 25%, about 15% and about 24.5%, about 15% and about 24%, about 15% and about 23.5%, about 15% and about 23%, about 15.5% and about 25%, about 15.5% and about 24.5%, about 15.5% and about 24%, about 15.5% and about 23.5%, or about 15.5% and about 23%. In some aspects, the one or more N-linked glycans are located at residue Asn76 (T5) and comprise a relative abundance of S2G2F between about 18.1% and about 22.9%, about 15.4% and about 20%, about 15.4% and about 22.9%. In some aspects, the relative abundance of S2G2F is about 18.5%.

In some aspects, the one or more N-linked glycans are located at residue Asn108 (T7) and comprise a relative abundance of S2G2F between about 18% and about 36%. In some aspects, the one or more N-linked glycans are located at residue Asn108 (T7) and comprise a relative abundance of S2G2F between about 18% and about 36%, about 18% and about 35.5%, about 18% and about 35%, about 18% and about 34.5%, about 18% and about 34%, about 18% and about 33.5%, about 18.5% and about 36%, about 18.5% and about 35.5%, about 18.5% and about 35%, about 18.5% and about 34.5%, about 18.5% and about 34%, about 18.5% and about 33.5%, about 19% and about 36%, about 19% and about 35.5%, about 19% and about 35%, about 19% and about 34.5%, about 19% and about 34%, about 19% and about 33.5%, about 19.5% and about 36%, about 19.5% and about 35.5%, about 19.5% and about 35%, about 19.5% and about 34.5%, about 19.5% and about 34%, about 19.5% and about 33.5%, about 20% and about 36%, about 20% and about 35.5%, about 20% and about 35%, about 20% and about 34.5%, about 20% and about 34%, about 20% and about 33.5%, about 20.5% and about 36%, about 20.5% and about 35.5%, about 20.5% and about 35%, about 20.5% and about 34.5%, about 20.5% and about 34%, or about 20.5% and about 33.5%. In some aspects, the one or more N-linked glycans are located at residue Asn108 (T7) and comprise a relative abundance of S2G2F between about 23.2% and about 33.8%, about 20.8% and about 32.6%, or about 20.8% and 33.8%. In some aspects, the relative abundance of S2G2F is about 23.5%.

In some aspects, the one or more N-linked glycan are located at residue Asn76 (T5) and comprise a relative abundance of S1G3F between about 2% and about 8%. In some aspects, the one or more N-linked glycan are located at residue Asn76 (T5) and comprise a relative abundance of S1G3F between about 2% and about 8%, about 2% and about 7.5%, about 2% and about 7%, about 2% and about 6.5%, about 2% and about 6%, about 2% and about 5.5%, about 2.5% and about 8%, about 2.5% and about 7.5%, about 2.5% and about 7%, about 2.5% and about 6.5%, about 2.5% and about 6%, about 2.5% and about 5.5%, about 3% and about 8%, about 3% and about 7.5%, about 3% and about 7%, about 3% and about 6.5%, about 3% and about 6%, about 3% and about 5.5%, about 3.5% and about 8%, about 3.5% and about 7.5%, about 3.5% and about 7%, about 3.5% and about 6.5%, about 3.5% and about 6%, about 3.5% and about 5.5%, about 4% and about 8%, about 4% and about 7.5%, about 4% and about 7%, about 4% and about 6.5%, about 4% and about 6%, or about 4% and about 5.5%. In some aspects, the one or more N-linked glycan are located at residue Asn76 (T5) and comprise a relative abundance of S1G3F between about 4.4% and about 5.6% or about 4.0% and about 5.5%. In some aspects, the relative abundance of S1G3F is about 4.6%.

In some aspects, the one or more N-linked glycans are located at residue Asn108 (T7) and comprise a relative abundance of S1G3F between about 0.5% and about 4%. In some aspects, the one or more N-linked glycans are located at residue Asn108 (T7) and comprise a relative abundance of S1G3F between about 0.5% and about 4%, about 0.5% and about 3.5%, about 0.5% and about 3%, about 0.5% and about 2.5%, about 1% and about 4%, about 1% and about 3.5%, about 1% and about 3%, or about 1% and about 2.5%. In some aspects, the one or more N-linked glycans are located at residue Asn108 (T7) and comprise a relative abundance of S1G3F between about 1.4% and about 2.2%, about 1.1% and about 1.9%, or about 1.1% and about 2.2%. In some aspects, the relative abundance of S1G3F is about 1.8%.

In some aspects, the one or more N-linked glycans are located at residue Asn76 (T5) and comprise a relative abundance of S2G4F between about 0.5% and about 4%. In some aspects, the one or more N-linked glycans are located at residue Asn76 (T5) and comprise a relative abundance of S2G4F between about 0.5% and about 4%, about 0.5% and about 3.5%, about 0.5% and about 3%, about 0.5% and about 2.5%, about 1% and about 4%, about 1% and about 3.5%, about 1% and about 3%, or about 1% and about 2.5%. In some aspects, the one or more N-linked glycans are located at residue Asn76 (T5) and comprise a relative abundance of S2G4F between about 1.9% and about 2.4%, about 1.4% and about 2.1%, or about 1.4% and about 2.4%. In some aspects, the relative abundance of S2G4F is about 2.3%.

In some aspects, the one or more N-linked glycans are sialic acid and have a molar ratio of NANA of from about 8 to about 11. In some aspects, the one or more N-linked glycans are sialic acid and have a molar ratio of NANA of from about 8.3 to about 11, from about 9.5 and about 10.1, or from about 8.3 to about 10.1. In some aspects, the molar ratio of NANA is about 10.0.

In some aspects, the one or more N-linked glycans are sialic acid and have a molar ratio of NANA of from about 0.1 to about 2.0. In some aspects, the one or more N-linked glycans are sialic acid and have a molar ratio of NANA of from 0.90 to about 1.20 or from about 0.3 to about 1.2. In some aspects, the molar ratio of NANA is about 1.0.

In some aspects, the glycosylation profile is analyzed via a N-linked carbohydrate profile release method. In some aspects, the glycosylation profile includes one or more asialylated glycans (Domain I), mono-sialylated glycans (Domain II), di-sialylated glycans (Domain III), and/or tri-sialylated and tetra-sialylated glycans (Domain IV+V). In some aspects, the asialylated glycans (Domain I) have a molar ratio of from about 28 to about 37, from about 29 to about 32, from about 28 to about 32, or from about 29 to about 37. In some aspects, the asialylated glycans (Domain I) have a molar ratio of about 31. In some aspects, the mono-sialylated glycans (Domain II) have a molar ratio of from about 26 to about 28, from about 27 to about 33, from about 26 to from about 33, from about 27 to about 28. In some aspects, the mono-sialylated glycans (Domain II) have a molar ratio of about 27. In some aspects, the di-sialylated glycans (Domain III) have a molar ratio of from about 27 to about 28, from about 22 to about 31, from about 27 to about 31, or from about 22 to about 28. In some aspects, the di-sialylated glycans (Domain III) have a molar ratio of about 27.4. In some aspects, the tri-sialylated and tetra-sialylated glycans (Domain IV+V) have a molar ratio of from about 13 to about 16, from about 8 to about 16, or from about 8 to about 16. In some aspects, the tri-sialylated and tetra-sialylated glycans (Domain IV+V) have a molar ratio of about 14.6.

In some aspects, the glycosylation profile includes one or more O-linked glycans. In some aspects, the glycosylation profile does not include more than one galactose-alpha-1,3-galactose (alpha-gal) linkage. In some aspects, the CTLA4 comprises a C-terminal lysine. In some aspects, the C-terminal lysine comprises a relative abundance of about 20% to about 25%. In some aspects, the C-terminal lysine comprises a relative abundance of about 3% to about 10%. In some aspects, the O-linked glycans are located at residues Ser129, Ser130, Ser136, and/or Ser139. In some aspects, the bioreactor comprises a feed media comprising glucose or galactose. In some aspects, the cells are mammalian cells. In some aspects, the cells are Chinese hamster ovary (CHO) cells. In some aspects, the cells are CHO-K1 cells, CHO-DXB11 cells, or CHO-DG44 cells.

The methods of the present disclosure also include a method of analyzing bi-antennary glycans of a CTLA4-Fc fusion protein, comprising measuring one or more N-linked glycans attached to one or more asparagine residues in the CTLA4 protein, wherein one of the bi-antennary glycans is G2F. In some aspects, the bi-antennary glycans are selected from a group consisting of G0F, G1F, G2F, S1G1F, S1G2F, and/or S2G2F. In some aspects, the bi-antennary glycans are measured via Ultra Performance Liquid Chromatography with fluorescence detection (UPLC-FLR). In some aspects, the Fc domain of the CTLA4-Fc fusion protein is cleaved prior to the measuring. In some aspects, the methods further comprise harvesting the protein from the bioreactor. In some aspects, the methods further comprise running the protein through a viral inactivation process. In some aspects, the viral inactivation process is run with 0.5% Triton X-100.

In some aspects, the methods further comprise adjusting the concentration of the protein. In some aspects, the methods further comprise formulating the protein.

BRIEF DESCRIPTION OF THE DRAWINGS

FIG. 1D shows the specific N-linked glycosylation sites (T5 on Asn76, T7 on Asn108, and T14 on Asn207) on the Abatacept molecule. The protease and the amino acid sequence are also shown.

FIG. 2B shows the mean peak VCD ($10^6$ cells/mL), peak VCD Dunnett's test p-value, mean day 0-5 doubling time (hrs), doubling time Dunnett's test p-value, mean day 0-14 IVCD ($10^9$ cells day/mL), IVCD Dunnett's test p-value, and VCD profile value in table form, after experimentation with various factors: High $CO_2$ represents a $CO_2$ set point of 22.4%. Late first feed is a first feed at 96 hours. Low initial pH is an induction pH of 6.9. Low initial VCD is an induction density of $0.15\times10^6$ cells/mL. High initial VCD is an induction density of $0.45\times10^6$ cells/mL. Low overall Temp is a temperature shift profile using three set points, 36° C. as an initial temperature set point, 33° C. as a second temperature set point, and 31° C. as a final temperature set point. Low Temperature Shift 1 is a temperature shift profile using three set points, 37° C. as an initial temperature set point, 33° C. as a second temperature set point, and 32° C. as a final temperature set point. Low Temperature Shift 2 is a temperature shift profile using three set points, 37° C. as an initial temperature set point, 34° C. as a second temperature set point, and 31° C. as a final temperature set point.

FIGS. 4A-4H show various glycosylation data collected on day 14 of a bioreactor production run for abatacept. FIG. 4A shows a statistical comparison of Day 14 Sialic Acid and N-linked domains (Domains I, I, III, and IV+V). FIG. 4B shows a comparison of titer and specific productivity between test groups. High $CO_2$ represents a $CO_2$ set point of 22.4%. Late first feed is a first feed at 96 hours. Low initial pH is an induction pH of 6.9. Low initial VCD is an induction density of $0.15\times10^6$ cells/mL. High initial VCD is an induction density of $0.45\times10^6$ cells/mL. Low overall Temp is a temperature shift profile using three set points, 36° C. as an initial temperature set point, 33° C. as a second temperature set point, and 31° C. as a final temperature set point. Low Temperature Shift 1 is a temperature shift profile using three set points (37° C., 33° C., and 32° C.). Low Temperature Shift 2 is a temperature shift profile using three set points (37° C., 34° C., and 31° C.). FIG. 4C shows an analysis of the G0F glycan present at sites T5 and T7 at day 14 across 5-L bioreactor manufacturing runs using each testing condition. FIG. 4D shows an analysis of the G2F glycan present at sites T5 and T7 at day 14 across 5-L bioreactor manufacturing runs using each testing condition. FIG. 4E shows an analysis of the S1G2F glycan present at sites T5 and T7 at day 14 across 5-L bioreactor manufacturing runs using each testing condition. FIG. 4F shows an analysis of the S2G2F glycan present at sites T5 and T7 at day 14 across 5-L bioreactor manufacturing runs using each testing condition. FIG. 4G shows an analysis of the S1G3F glycan present at sites T5 and T7 at day 14 across 5-L bioreactor manufacturing runs using each testing condition. FIG. 4H shows an analysis of the S2G4F glycan present at the T5 site at day 14 across 5-L bioreactor manufacturing runs using each testing condition.

FIG. 5 shows day 16 harvest data regarding N-linked glycosylation (domains I, II, III, and IV+V), High Molecular Weight contaminants, host cell protein, and ribosomal DNA (rDNA) contamination. Its Dunnett's test p-value results for Day 16 pre-harvest N-link, HMW, HCP and rDNA are also provided.

FIG. 6A shows a diagram of the tested process parameter for the 5-L scale bioreactors. FIGS. 6B-6C show the glycosylation profile of protein produced across a number of sample bioreactor runs, along with contaminants such as HMW, HCP, and DNA.

FIG. 7 shows a summary of the process attributes that are affected by modifications in the process parameters.

FIG. 8A shows the relative abundance of various glycoforms present on the T5 glycosylation site across the processes used in the present disclosure (J), and an alternate process (F).

FIG. 9A shows the relative abundance of various glycoforms present on the T5 glycosylation site across the processes used in the present disclosure (J), and an alternate process (F).

DETAILED DESCRIPTION OF THE DISCLOSURE

Figure 1A:
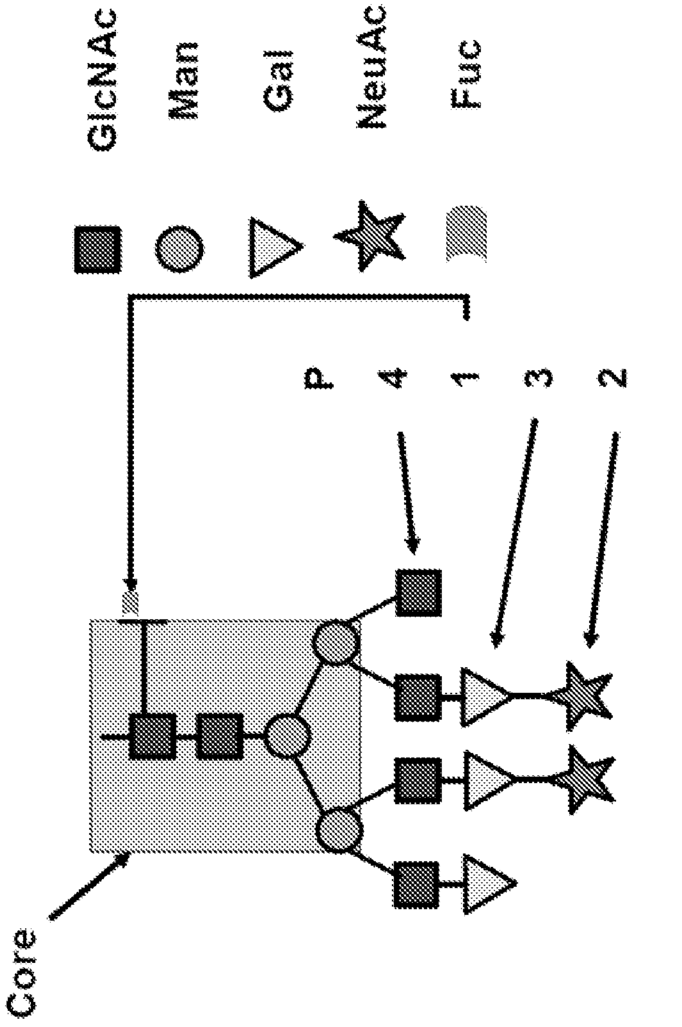
FIG. 1A show the general structure of common N-linked glycans. GlcNAc (square) is N-Acetylglucosamine. Man (circle) is Mannose. Gal (solid triangle) is Galactose. NeuAc or Neu5Ac (star) is N-Acetylneuraminic acid. Fuc (bullet) is Fucose. The core structure is shown in a grayed box.

The present disclosure is directed to methods of improving the yield of a protein by cells while maintaining the desired property, e.g., glycosylation pattern, of the protein. In some aspects, the methods of improving yields comprises culturing the cells in a bioreactor for a protein induction phase under suitable conditions including, but not limited to, adjusting to temperatures, setting pH, using a particular viable cell density, setting a $CO_2$ concentration, or any combination thereof.

I. Definitions

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one tenth and one hundredth of an integer), unless otherwise indicated.

As used herein, the term "CTLA4 extracellular domain" refers to a protein domain comprising all or a portion of the amino acid sequence shown in SEQ ID NO: 1, that binds to B7-1 (CD80) and/or B7-2 (CD86). In some aspects, a CTLA4 extracellular domain can comprise a polypeptide having an amino acid sequence that is at least 75%, 80%, 85%, 90%, 95%, 96%, 97%, 98%, or 99% identical to SEQ ID NO: 1. A CTLA4 extracellular domain is represented by the following sequence:

```
SEQ ID NO: 1:
MHVAQPAVVLASSRGIASFVCEYASPGKATEVRVTVLRQADSQVTEVCAAT

YMMGNELTFLDDSICTGTSSGNQVNLTIQGLRAMDTGLYICKVELMYPPPY

YLGIGNGTQIYVIDPEPCPDSD
```

As used herein, the terms "CTLA4-Ig" or "CTLA4-Ig molecule" or "CTLA4Ig molecule" or "CTLA4-Ig protein" or "CTLA4Ig protein" or "CTLA4-Fc" are used interchangeably, and refer to a protein molecule that comprises at least a CTLA4-Ig polypeptide having a CTLA4 extracellular domain and an immunoglobulin constant region or portion thereof. In some aspects, for example, a CTLA4-Ig polypeptide comprises at least the amino acid sequence of SEQ ID NO: 2. In certain aspects, the CTLA4 extracellular domain and the immunoglobulin constant region or portion thereof can be wild-type, or mutant or modified. A mutant CTLA4-Ig polypeptide is a CTLA4-Ig polypeptide comprising a mutant CTLA4 extracellular domain. A mutant CTLA4Ig molecule comprises at least a mutant CTLA4-Ig polypeptide. In some aspects, the CTLA4 extracellular domain and the immunoglobulin constant region or portion thereof can be mammalian, including human or mouse. In some aspects, a mutant CTLA4 extracellular domain can have an amino acid sequence that is at least 75%, 80%, 85%, 90%, 95%, 96%, 97%, 98%, or 99% identical to the CTLA4 extracellular domain shown in any one or more of SEQ ID NO: 2, 3, 4, 5, 6, 7, or 8. The polypeptide can further comprise additional protein domains. A CTLA4-Ig molecule can refer to a monomer of the CTLA4-Ig polypeptide, and also can refer to multimer forms of the polypeptide, such as dimers, tetramers, and hexamers, etc. (or other high molecular weight species). CTLA4-Ig molecules are also capable of binding to CD80 and/or CD86. Examples of CTLA4-Ig and fragments (e.g., abatacept) are shown in SEQ ID NOs: 2, 3, 4, 5, 6, 7, and 8. In some aspects, abatacept is a combination of SEQ ID NO: 2, 3, 4, 5, 6, 7, and 8.

```
[CTLA4-Ig amino acid sequence]
                                      SEQ ID NO: 2
MGVLLTQRTLLSLVLALLFPSMASMAMHVAQPAVVLASSRGIASFVCEYAS

PGKATEVRVTVLRQADSQVTEVCAATYMMGNELTFLDDSICTGTSSGNQVN

LTIQGLRAMDTGLYICKVELMYPPPYYLGIGNGTQIYVIDPEPCPDSDQEP

KSSDKTHTSPPSPAPELLGGSSVFLFPPKPKDTLMISRTPEVTCVVVDVSH

EDPEVKFNWYVDGVEVHNAKTKPREEQYNSTYRVVSVLTVLHQDWLNGKEY

KCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGN

VFSCSVMHEALHNHYTQKSLSLSPGK

[amino acids 25-383 of SEQ ID NO: 2]
                                      SEQ ID NO: 3
MAMHVAQPAVVLASSRGIASFVCEYASPGKATEVRVTVLRQADSQVTEVCA

ATYMMGNELTFLDDSICTGTSSGNQVNLTIQGLRAMDTGLYICKVELMYPP

PYYLGIGNGTQIYVIDPEPCPDSDQEPKSSDKTHTSPPSPAPELLGGSSVF

LFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSP

GK
```

-continued

[amino acids 26-383 of SEQ ID NO: 2]

SEQ ID NO: 4

```
AMHVAQPAVVLASSRGIASFVCEYASPGKATEVRVTVLRQADSQVTEVCAA
TYMMGNELTFLDDSICTGTSSGNQVNLTIQGLRAMDTGLYICKVELMYPPP
YYLGIGNGTQIYVIDPEPCPDSDQEPKSSDKTHTSPPSPAPELLGGSSVFL
FPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG
K
```

[amino acids 27-383 of SEQ ID NO: 2]

SEQ ID NO: 5

```
MHVAQPAVVLASSRGIASFVCEYASPGKATEVRVTVLRQADSQVTEVCAAT
YMMGNELTFLDDSICTGTSSGNQVNLTIQGLRAMDTGLYICKVELMYPPPY
YLGIGNGTQIYVIDPEPCPDSDQEPKSSDKTHTSPPSPAPELLGGSSVFLF
PPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPGK
```

[amino acids 25-382 of SEQ ID NO: 2]

SEQ ID NO: 6

```
MAMHVAQPAVVLASSRGIASFVCEYASPGKATEVRVTVLRQADSQVTEVCA
ATYMMGNELTFLDDSICTGTSSGNQVNLTIQGLRAMDTGLYICKVELMYPP
PYYLGIGNGTQIYVIDPEPCPDSDQEPKSSDKTHTSPPSPAPELLGGSSVF
LFPPKPKDTLMISRTPEVTCVVVDVSHEDPEVKFNWYVDGVEVHNAKTKPR
EEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLSP
G
```

[amino acids 26-382 of SEQ ID NO: 2]

SEQ ID NO: 7

```
AMHVAQPAVVLASSRGIASFVCEYASPGKATEVRVTVLRQADSQVTEVCAA
TYMMGNELTFLDDSICTGTSSGNQVNLTIQGLRAMDTGLYICKVELMYPPP
YYLGIGNGTQIYVIDPEPCPDSDQEPKSSDKTHTSPPSPAPELLGGSSVFL
FPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG
```

[amino acids 27-382 of SEQ ID NO: 2]

SEQ ID NO: 8

```
MHVAQPAVVLASSRGIASFVCEYASPGKATEVRVTVLRQADSQVTEVCAAT
YMMGNELTFLDDSICTGTSSGNQVNLTIQGLRAMDTGLYICKVELMYPPPY
YLGIGNGTQIYVIDPEPCPDSDQEPKSSDKTHTSPPSPAPELLGGSSVFLF
PPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPRE
```

-continued

```
PQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG
```

As used herein, the term "soluble CTLA4" means a molecule that can circulate in vivo or CTLA4 which is not bound to a cell membrane. For example, the soluble CTLA4 can include CTLA4-Ig which includes the extracellular region of CTLA4, linked to an Ig.

As used herein, the term "dimer" refers to a CTLA4-Ig protein or CTLA4-Ig molecule composed of two CTLA4-Ig polypeptides or monomers linked or joined together. The linkage between monomers or a dimer can be a non-covalent linkage or interaction, a covalent linkage or interaction (e.g., one or more disulfide bonds), or both. A CTLA4-Ig protein or CTLA4-Ig molecule composed of two identical monomers is a homodimer. A CTLA4-Ig homodimer also encompasses a molecule comprising two monomers that can differ slightly in sequence. A homodimer encompasses a dimer where the monomers joined together have substantially the same sequence. The monomers comprising a homodimer share considerable structural homology. For example, the differences in sequence can be due to N-terminal processing modifications of the monomer.

As used herein, the terms "glutamate" and "glutamic acid" are used interchangeably.

As used herein, "T5", T7", and T15" refer to specific glycosylation sites present on the Abatacept molecule. These labels correspond to Asparagine 76, Asparagine 108, and Asparagine 207, respectively, and correspond to the residues in SEQ ID NO: 5 (bolded). Peptide sequence of T5, T7 and T14 are listed in FIG. 1C. The relative abundance of major glycoforms was calculated from extracted ion chromatograms of glycopeptides.

The N-linked glycosylation sites have been identified at Asn76, Asn108 (CTLA4 region) and Asn207 (Fc region) with respect to SEQ ID NO: 5 by LC-MS tryptic peptide mapping with mass spectrometric detection. A five-character code is used to define carbohydrate structural classes, e.g., P2100, P2120, P2121, P3131, and P4142. With respect to this labeling scheme, the first character (P) in the code defines the released carbohydrate as an N-linked structure containing a trimannosyl core structure. The second character represents the number of N-Acetylglucosamine (GlcNAc) units attached to the core. The third character (0 or 1) represents whether there is a fucose (Fuc) attached to the first GlcNAc of the core. The fourth character represents the number of Galactose (Gal) sugars attached to the core. The fifth character represents the number of SA (N-acetylneuraminic acid or N-glycolylneuraminic acid) attached to the carbohydrate. P2100 can be also denoted as G0F. P2110 can be also denoted as G1F. P2120 can be also denoted as G2F. P2121 can be also denoted as S1G2F. P2122 can be also denoted as S2G2F (di. P3131 can be also denoted as S1G3F. P4142 can be also denoted as S2G4F. Representative diagrams of these glycans can be seen in FIGS. 1A and 1B.

As used herein, "Domain I" refers to asialylated glycans (such as G0F, G1F, and G2F), "Domain II" refers to monosialylated glycans (such as S1G1F and S1G2F), "Domain III" refers to di-sialylated glycans (such as S2G2F), and "Domain IV" and "Domain V" refer to tri-sialylated and tetra-sialylated glycans.

As used herein, the term "purified" refers to a composition comprising a CTLA4-Ig molecule or a selected population of CTLA4-Ig molecules that is removed from its natural environment (e.g., is isolated) and is at least 90% free, 91% free, 92% free, 93% free, 94% free, 95% free, 96% free, 97% free, 98% free, 99% free, 99.5% free, or 99.9% free from other components, such as cellular material or culture medium, with which it is naturally associated. "Purified" can also refer to a composition comprising a CTLA4-Ig molecule or a selected population of CTLA4-Ig molecules that is removed from its natural environment and is at least 60% free, 65% free, 70% free, 75% free, 80% free, or 85% free from other components, such as cellular material or culture medium, with which it is naturally associated. For example, with respect to a recombinantly produced CTLA4-Ig protein molecule, the term "purified" can also refer to a composition comprising a CTLA4-Ig protein molecule that is removed from the production environment such that the protein molecule is at least 90% free, 91% free, 92% free, 93% free, 94% free, 95% free, 96% free, 97% free, 98% free, 99% free, 99.5% free, or 99.9% free from protein molecules which are not polypeptides of SEQ ID NO: 2 or mutant polypeptides of SEQ ID NO: 2 which are of interest. "Purified" does not exclude mixtures of CTLA4-Ig molecules (such as dimers) with other CTLA4-Ig molecules (such as tetramer). "Purified" does not exclude pharmaceutically acceptable excipients or carriers combined with CTLA4-Ig molecules, wherein the CTLA4-Ig molecules have been taken out of their native environment.

As used herein, the term "large-scale process" is used interchangeably with the term "industrial-scale process". The term "culture vessel" is used interchangeably with "bioreactor", "reactor" and "tank". A bioreactor used on an industrial scale can be at least 2,000 L, at least 5,000 L, at least 10,000 L, at least 15,000 L, at least 20,000 L, at least 25,000 L, or any size appropriate for the large production scale necessary to produce an industrial supply.

A "liquid culture" refers to cells (for example, bacteria, plant, insect, yeast, or animal cells) grown on supports, or growing suspended in a liquid nutrient medium.

A "seed culture" refers to a cell culture grown in order to be used to inoculate larger volumes of culture medium. The seed culture can be used to inoculate larger volumes of media in order to expand the number of cells growing in the culture (for example, cells grown in suspension).

As used herein, the terms "culture medium" and "cell culture medium" and "feed medium" and "fermentation medium" refer to a nutrient solutions used for growing and or maintaining cells, especially mammalian cells. Without limitation, these solutions ordinarily provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range. The nutrient solution can be supplemented electively with one or more components from any of the following categories: (1) hormones and other growth factors such as, serum, insulin, transferrin, and epidermal growth factor; (2) salts, for example, magnesium, calcium, and phosphate; (3) buffers, such as HEPES; (4) nucleosides and bases such as, adenosine, thymidine, and hypoxanthine; (5) protein and tissue hydrolysates, for example peptone or peptone mixtures which can be obtained from purified gelatin, plant material, or animal byproducts; (6) antibiotics, such as gentamycin; (7) cell protective agents, for example pluronic polyol; and (8) galactose. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., Meth. Enz. 58:44 (1979), Barnes et al., Anal. Biochem. 102:255 (1980) can be used as culture media for the host cells. Any other necessary supplements can also be included at appropriate concentrations.

As used herein, "culturing" refers to growing one or more cells in vitro under defined or controlled conditions. Examples of culturing conditions which can be defined include temperature, gas mixture, time, and medium formulation.

As used herein, "expanding" refers to culturing one or more cells in vitro for the purpose of obtaining a larger number of cells in the culture.

As used herein, "temperature set point" refers to the temperature setting of a bioreactor or other upstream processing vessel used to grow cells and/or produce protein product. A temperature set point can be established at the outset of cell culture, where it can also be referred to as an "initial temperature set point". Subsequent changes in temperature during cell culture after the initial temperature set point can be referred to using ordinal numbering, i.e., a second temperature set point, or subsequently a third temperature set point. The last temperature set point before downstream processing can also be referred to as a "final temperature set point". In some instances, a process can comprise an initial temperature set point, a second temperature set point, and third (and final) temperature set point.

As used herein, "$CO_2$ set point" or "$CO_2$ set point" refers to the concentration of $CO_2$ present in an upstream production process. The $CO_2$ set point is represented in percentage (%) by volume.

As used herein, "population" refers to a group of two or more molecules ("population of molecules") or cells ("population of cells") that are characterized by the presence or absence of one or more measurable or detectable properties. In a homogeneous population, the molecules or cells in the population are characterized by the same or substantially the same properties (for example, the cells of a clonal cell line). In a heterogeneous population, the molecules or cells in the population are characterized by at least one property that is the same or substantially the same, where the cells or molecules can also exhibit properties that are not the same (for example, a population of CTLA4-Ig molecules having a substantially similar average sialic content, but having non-similar mannose content).

As used herein, "high molecular weight aggregate" is used interchangeably with "high molecular weight species" or "HMW" to refer to a CTLA4-Ig molecule comprising at least three CTLA4-Ig monomers. For example, a high molecular weight aggregate can be a tetramer, a pentamer or a hexamer.

As used herein "Protein A" refers to a protein that is approximately 42 kDa and binds very strongly to the Fc portion of an immunoglobulin, and its use in the purification of antibodies is well known in the art. Protein A has been extensively used in the art for purification. (Boyle et al., 1993; Hou et al. 1991). When applied to Protein A, the term "residual", or "rPA" refers to any remaining Protein A present in a mixture due its use in purification of a protein of interest or an antibody further upstream in a manufacturing process.

"Percent (%) yield" refers to the actual yield divided by the theoretical yield, and that value multiplied by 100. The actual yield can be given as the weight in gram or in mol (for example, a molar yield). The theoretical yield can be given as the ideal or mathematically calculated yield.

As used herein, "glycosylation content" refers to an amount of N-linked or O-linked sugar residues covalently attached to a protein molecule, such as a glycoprotein like a CTLA4-Ig molecule.

As used herein, "glycosylation" refers to the addition of complex oligosaccharide structures to a protein at specific sites within the polypeptide chain. Glycosylation of proteins and the subsequent processing of the added carbohydrates can affect protein folding and structure, protein stability, including protein half-life, and functional properties of a protein. Protein glycosylation can be divided into two classes by virtue of the sequence context where the modification occurs, O-linked glycosylation and N-linked glycosylation. O-linked polysaccharides are linked to a hydroxyl group, usually to the hydroxyl group of either a serine or a threonine residue. O-glycans are not added to every serine and threonine residue. O-linked oligosaccharides are usually mono or biantennary, i.e. they comprise one or at most two branches (antennas), and comprise from one to four different kinds of sugar residues, which are added one by one. N-linked polysaccharides are attached to the amide nitrogen of an asparagine. Only asparagines that are part of one of two tripeptide sequences, either asparagine-X-serine or asparagine-X-threonine (where X is any amino acid except proline), are targets for glycosylation. N-linked oligosaccharides can have from one to four branches referred to as mono-, bi-, tri-tetraantennary. The structures of and sugar residues found in N- and O-linked oligosaccharides are different. Despite that difference, the terminal residue on each branch of both N- and O-linked polysaccharide can be modified by a sialic acid molecule a modification referred as sialic acids capping. Sialic acid is a common name for a family of unique nine-carbon monosaccharides, which can be linked to other oligosaccharides. Two family members are N-acetyl neuraminic acid, abbreviated as Neu5Ac, NeuAc, or NANA, and N-glycolyl neuraminic acid, abbreviated as Neu5Gc or NANA. The most common form of sialic acid in humans is NANA. N-acetylneuraminic acid (NANA) is the primary sialic acid species present in CTLA4-Ig molecules. However, it should be noted that minor but detectable levels of N glycolylneuraminic acid (NANA) are also present in CTLA4-Ig molecules. Furthermore, the method described herein can be used to determine the number of moles of sialic acids for both NANA and NANA, and therefore levels of both NANA and NANA are determined and reported for CTLA4-Ig molecules. N- and O-linked oligosaccharides have different number of branches, which provide different number of positions to which sialic acid molecules can be attached. N-linked oligosaccharides can provide up to four attachment positions for sialic acids, while O-linked oligosaccharides can provide two sites for sialic acid attachment.

As used herein, the term "molar ratio of sialic acids to protein" or "MR" is calculated and given as number of moles of sialic acid molecules per moles of protein (CTLA4-Ig molecules) or dimer.

As used herein, the term "glycoprotein" refers to a protein that is modified by the addition of one or more carbohydrates, including the addition of one or more sugar residues.

As used herein, the term "sialylation" refers to the addition of a sialic acid residue to a protein, including a glycoprotein.

As used herein, the term "glycoprotein isoform" refers to a molecule characterized by its carbohydrate and sialic acid content as determined by isoelectric focusing (IEF) gel electrophoresis or other suitable methods for distinguishing different proteins in a mixture by their molecular weight, charge, and/or other characteristics. For example, each distinct band observed on an IEF gel represents molecules that have a particular isoelectric point (pI) and thus the same net overall charge. A glycoprotein isoform can be a distinct band observed on an IEF gel where each band can be a population of molecules that have a particular pI.

As used herein, Imaged Capillary Isoelectric Focusing (iCIEF) refers to a method used for the separation of proteins by their isoelectric point (pI). In this method, samples are prepared to a final concentration of ~1 mg/mL with water, methyl cellulose, ampholytes, and pI markers, and then injected by an autosampler into an imaged capillary isoelectric focusing system (iCIEF). Electrophoresis separates the samples through a pH gradient within a fluorocarbon (FC) coated capillary based on charge variance of the isoforms.

"Immune tolerance" refers to a state of unresponsiveness to a specific antigen or group of antigens to which a person is normally responsive (for example, a state in which a T cell can no longer respond to antigen).

"Potency" refers to a measure of the response as a function of ligand concentration. For example, agonist potency is quantified as the concentration of ligand that produces half the maximal effect ($EC_{50}$). A non-limiting pharmacological definition of potency includes components of affinity and efficacy, where, efficacy is the ability of a drug to evoke a response once bound. Potency is related to affinity, but potency and affinity are different measures of drug action.

As used herein, "pharmaceutically acceptable carrier" refers to a vehicle for a pharmacologically active agent. The carrier facilitates delivery of the active agent to the target site without terminating the function of the agent. Non-limiting examples of suitable forms of the carrier include solutions, creams, gels, gel emulsions, jellies, pastes, lotions, salves, sprays, ointments, powders, solid admixtures, aerosols, emulsions (e.g., water in oil or oil in water), gel aqueous solutions, aqueous solutions, suspensions, liniments, tinctures, and patches suitable for topical administration.

As used herein, the phrase "pharmaceutically acceptable composition" (or "pharmaceutical composition") refers to a composition that is acceptable for pharmaceutical administration, such as to a human being. Such a composition can include substances that are impurities at a level not exceeding an acceptable level for pharmaceutical administration (such level including an absence of such impurities), and can include pharmaceutically acceptable excipients, vehicles, carriers and other inactive ingredients, for example, to formulate such composition for ease of administration, in addition to any active agent(s). For example, a pharmaceutically acceptable CTLA4-Ig composition can include MCP-1 or DNA, so long as those substances are at a level acceptable for administration to humans.

"Drug substance" is the active pharmaceutical ingredient contained in a pharmaceutical composition. The term "drug substance" includes an active pharmaceutical ingredient in solution and/or in buffered form. "Drug product" is a pharmaceutical composition containing drug substance formulated for pharmaceutical administration. For purposes of the assays contained in the Examples and elsewhere herein, which can refer to drug substance and/or drug product, exemplary drug substances and drug products that can be assayed are as follows.

Exemplary drug product for CTLA4Ig molecules include:

| Composition of lyophilized CTLA4-Ig protein (250 mg/vial) drug product | |
|---|---|
| Component | Amount (mg/vial) |
| CTLA4-Ig protein | 262.5 |
| Maltose monohydrate | 525 |
| Sodium phosphate monobasic, monohydrate | 18.1 |
| Sodium chloride | 15.3 |
| Hydrochloric Acid | Adjust to pH 7.5 |
| Sodium hydroxide | Adjust to pH 7.5 |

The term "inoculation" as used herein refers to the addition of cells to culture medium to start the culture.

The term "induction" or "induction phase" or "growth phase" of the cell culture as used herein refers to the initial seeding of the bioreactor at the outset of upstream cell culture, and includes the period of exponential cell growth (for example, the log phase) where cells are primarily dividing rapidly. During this phase, the rate of increase in the density of viable cells is higher than at any other time point.

As used herein, the term "production phase" of the cell culture refers to the period of time during which cell growth is stationary or is maintained at a near constant level. The density of viable cells remains approximately constant over a given period of time. Logarithmic cell growth has terminated and protein production is the primary activity during the production phase. The medium at this time is generally supplemented to support continued protein production and to achieve the desired glycoprotein product.

As used herein, the terms "expression" or "expresses" are used to refer to transcription and translation occurring within a cell. The level of expression of a product gene in a host cell can be determined on the basis of either the amount of corresponding mRNA that is present in the cell or the amount of the protein encoded by the product gene that is produced by the cell, or both.

As used herein "N-linked glycan" refers to a protein modification where a glycan is linked to a glycoconjugate via a nitrogen linkage. The acceptors of the glycan are selected asparagine residues of polypeptide chains that have entered the periplasm or the lumen of the ER, respectively. Oligosaccharyltransferase, the central enzyme of the N-glycosylation pathway, catalyzes the formation of an N-glycosidic linkage of the oligosaccharide to the side-chain amide of asparagine residues that are specified by the consensus sequence N-X-S/T. All eukaryotic N-glycans share a common core sequence, Manα1-3(Manα1-6)Manβ1-4 GlcNAcβ1-4 GlcNAcβ1-Asn-X-Ser/Thr, and are classified into three types: (1) oligomannose, in which only Man residues extend the core; (2) complex, in which "antennae" initiated by GlcNAc extend the core; and (3) hybrid, in which Man extends the Manα1-6 arm of the core and one or two GlcNAcs extend the Manal-3 arm.

As used herein, "N-linked glycosylation" refers the attachment of oligosaccharides to a nitrogen atom, usually the N4 of asparagine residues. N-glycosylation can occur on secreted or membrane bound proteins, mainly in eukaryotes and archaea. A detailed review of the biosynthetic pathways and enzymes used to generate N-linked glycans (e.g., high mannose type oligosaccharides) are described in Stanley et al., "N-Glycans" in Essentials of Glycobiology, Ed. Varki, Cummings, and Eskho, Cold Spring Harbor Press, 2009.

As used herein, the term "mass spectrometry" refers to a sensitive technique used to detect, identify and quantitate molecules based on their mass-to-charge (m/z) ratio. Electric fields are used to separate ions according to their mass-to-charge ratio (m/z), the ratio of mass to the integer number of charges (z), as they pass along the central axis of parallel and equidistant poles or rods, such as a quadrupole, which contains four poles or rods. Each rod has two voltages applied, one of which is a fixed direct current and the second is an alternating current that cycles with a superimposed radio frequency. The magnitude of the applied electric field can be ordered such that only ions with a specific m/z ratio can travel through the quadrupole, prior to being detected. Ions with all other m/z values are deflected onto trajectories that would cause them to collide with the quadrupole rods and discharge, or be ejected from the mass analyzer field and removed via the vacuum. The quadrupole is often referred to as an exclusive detector because only ions with a specific m/z are stable in the quadrupole at any one time. Those ions with a stable trajectory are often referred to as having noncollisional, resonant or stable trajectories.

Generally, for an experiment on a triple-quadrupole mass spectrometer, the first quadrupole (Q1) is set to pass ions only of a specified m/z (precursor ions) of an expected chemical species in the sample. The second quadrupole (i.e. Q2 or the collision cell) is used to fragment the ions passing through Q1. The third quadrupole (Q3) is set to pass to the detector only ions of a specified m/z (fragment ions) corresponding to an expected fragmentation product of the expected chemical species. In some aspects, the sample is ionized in the mass spectrometer to generate one or more protonated or deprotonated molecular ions. In some aspects, the one or more protonated or deprotonated molecular are singly charged, doubly charged, triply charged or higher. In some aspects, the mass spectrometer is a triple quadrupole mass spectrometer. In some aspects, the resolutions used for Q1 and Q3 are unit resolution. In other aspects, the resolutions used for Q1 and Q3 are different. In other aspects, the resolution used for Q1 is higher than the unit resolution of Q3.

As used herein, the term "fluorophore" refers to a fluorescent chemical compound that can re-emit light upon light excitation. Fluorophores typically contain several combined aromatic groups, or planar or cyclic molecules with several π bonds. Two commonly used fluorophores are 2-AB (2-aminobenzamide) and 2-AA (anthranilic acid or 2-aminobenzoic acid). Other fluorophores include PA (2-Aminopyridine), AMAC (2-aminoacridone), ANDS (7-Amino-1,3-naphthalenedisulfonic acid), ANTS (8-Aminonaphthalene-1,3,6-trisulfonic acid), APTS (9-Aminopyrene-1,4,6-trisulfonic acid), and 3-(acetylamino)-6-aminoacridine.

A "glycan profile" as used in the disclosure should be understood to be any defined set of values of quantitative results for glycans that can be used for comparison to reference values or profiles derived from another sample or a group of samples. For instance, a glycan profile of a sample from a protein sample might be significantly different from a glycan profile of a sample from an alternate source. A glycan profile can aid in predicting or anticipating a protein's pharmacodynamic (PD) or pharmacokinetic (PK) therapeutic effects by comparing the profile to a reference or standard profile. Reference and sample glycan profiles can be generated by any analysis instrument capable of detecting glycans, such as mass spectrometry. The one or more N-glycans can be Galactose (Gal), N-Acetylgalactosamine (GalNAc), Galactosamine (GalN), Glucose (Glc), N-Acetylglucosamine (GlcNAc), Glucosamine (GlcN), Mannose (Man), N-Acetylmannosamine (ManNAc), Mannosamine (ManN), Xylose (Xyl), N-Acetylneuraminic acid (Neu5Ac), N-Glycolylneuraminic acid (Neu5Gc), 2-Keto-3-deoxynononic acid (Kdn), Fucose (Fuc), Glucuronic Acid (GlcA), Iduronic acid (IdoA), Galacturonic acid (GalA), Mannuronic acid (ManA), or any combination thereof.

As used herein, the phrase “working solution(s)” refers to solutions that are used in a method. Non-limiting examples of working solutions include buffers.

As used herein, “reference material” refers to a material that is used as a standard in a method. For example, a reference material can be used as a standard to which experimental samples will be compared.

The absence of a substance is contemplated where no lower limit is provided with regard to a range of amounts of such substance.

As used herein, recited temperatures in reference to cell culture refers to the temperature setting on the instrument that regulates the temperature of the bioreactor. Of course, the temperature of the liquid culture itself will adopt the temperature set on the instrument regulating the temperature for the bioreactor. Where the temperature refers to a cell culture that is maintained on a shelf in an incubator, the temperature then refers to the shelf temperature of the incubator.

II. Method of Improving Yield

The present disclosure provides method of improving the yield of a protein by cells, comprising culturing the cells in a bioreactor for a protein induction phase under suitable conditions, wherein the suitable conditions include, but are not limited to, adjustment of an initial temperature set point, adjustment of a second temperature set point, adjustment of a final temperature set point, adjustment of a feed time, adjustment of an initial pH, adjustment of a pH shift, adjustment of a $CO_2$ concentration, adjustment of an initial cell density, or adjustment of any combination thereof.

The methods of the present disclosure are useful to create reactor conditions where the reactor conditions improve protein yield. In some aspects, the conditions improve the protein yield by at least 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, or at least about 400%; as compared to a method without the suitable conditions, e.g., adjustment of the initial, the second, and the final temperature set points, e.g., temperature set points of 36° C., 33° C., and 31° C. In some aspects, the conditions improve the protein yield by at least 150%. In some aspects, the conditions improve the protein yield by at least 160%. In some aspects, the conditions improve the protein yield by at least 170%. In some aspects, the conditions improve the protein yield by at least 180%. In some aspects, the conditions improve the protein yield by at least 190%. In some aspects, the conditions improve the protein yield by at least 200%. In some aspects, the conditions improve the protein yield by at least 210%. In some aspects, the conditions improve the protein yield by at least 220%. In some aspects, the conditions improve the protein yield by at least 230%. In some aspects, the conditions improve the protein yield by at least 240%. In some aspects, the conditions improve the protein yield by at least 250%. In some aspects, the conditions improve the protein yield by at least 260%. In some aspects, the conditions improve the protein yield by at least 270%. In some aspects, the conditions improve the protein yield by at least 280%. In some aspects, the conditions improve the protein yield by at least 290%. In some aspects, the conditions improve the protein yield by at least 300%. In some aspects, the conditions improve the protein yield by at least 310%. In some aspects, the conditions improve the protein yield by at least 320%. In some aspects, the conditions improve the protein yield by at least 330%. In some aspects, the conditions improve the protein yield by at least 340%. In some aspects, the conditions improve the protein yield by at least 350%. In some aspects, the conditions improve the protein yield by at least 360%. In some aspects, the conditions improve the protein yield by at least 370%. In some aspects, the conditions improve the protein yield by at least 380%. In some aspects, the conditions improve the protein yield by at least 390%. In some aspects, the conditions improve the protein yield by at least 400%.

In some aspects, the present methods improve the protein yield by at least about 2 fold, at least about 3 fold, at least about 4 fold, at least about 5 fold, at least about 6 fold, at least about 7 fold, at least about 8 fold, at least about 9 fold, or at least about 10 fold higher than a method without the suitable conditions, e.g., adjustment of the initial, the second, and the final temperature set points, e.g., temperature set points of 36° C., 33° C., and 31° C. In some aspects, the present methods improve the protein yield by about 2 fold to about 3 fold. In some aspects, the present methods improve the protein yield by about 3 fold to about 4 fold. In some aspects, the present methods improve the protein yield by about 4 fold to about 5 fold. In some aspects, the present methods improve the protein yield by about 5 fold to about 6 fold. In some aspects, the present methods improve the protein yield by about 6 fold to about 7 fold. In some aspects, the present methods improve the protein yield by about 7 fold to about 8 fold. In some aspects, the present methods improve the protein yield by about 8 fold to about 9 fold.

The methods of the present disclosure are also useful to increase total protein output as a fraction of total host cell protein so that a larger protein yield per batch is achieved. In some aspects, the methods of the present disclosure are also useful to increase total protein output with a desired glycosylation pattern based on alterations to the protein's residence time in the Golgi and exposure to glycosylation enzymes. In some aspects, the conditions improve the protein yield of the protein with the desired glycosylation profile by at least 150%, at least about 160%, at least about 170%, at least about 180%, at least about 190%, at least about 200%, at least about 210%, at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, or at least about 400%; as compared to a method without the suitable conditions, e.g., adjustment of the initial, the second, and the final temperature set points, e.g., temperature set points of 36° C., 33° C., and 31° C.

The methods of the present disclosure are useful to reduce the growth rate and/or steady state cell density of the culture in order to improve overall yield and/or control the glycosylation profile of the protein. In some aspects, the method reduces cell growth rate. In some aspects, the cell growth exhibits a mean 0-5 day doubling time of from about 30.0 hours to about 45.0 hours, about 30.0 hours to about 40.0 hours, about 31 hours to about 44 hours, about 32 hours to about 43 hours, or about 33 hours to about 42 hours. In some aspects, the cell growth exhibits a mean 0-5 day doubling time of from about 30 hours to about 42 hours, e.g., 30 hours, 31 hours, 32 hours, 33 hours, 34 hours, 35 hours, 36 hours, 37 hours, 38 hours, 39 hours, 40 hours, 41 hours, or 42 hours. In some aspects, the cell growth exhibits a mean 0-5 day doubling time of from about 32 hours to about 38 hours. In some aspects, the cell growth exhibits a mean 0-5 day doubling time of from about 33 hours to about 37 hours. In some aspects, the cell growth exhibits a mean 0-5 day doubling time of from about 34 hours to about 36 hours.

In some aspects, the cell growth rate exhibits a mean 0-5 day doubling time of about 30 hours. In some aspects, the cell growth rate exhibits a mean 0-5 day doubling time of about 32 hours. In some aspects, the cell growth rate exhibits a mean 0-5 day doubling time of about 34 hours. In some aspects, the cell growth rate exhibits a mean 0-5 day doubling time of about 38 hours. In some aspects, the cell growth rate exhibits a mean 0-5 day doubling time of about 40 hours.

The methods of the present disclosure are also useful for controlling viable cell density or peak viable cell density during protein production. In some aspects, the cell viability exhibits a mean peak viable cell density (VCD) of from about $5\times10^6$ cells/mL to about $21\times10^6$ cells/mL. In some aspects, the cell viability exhibits a mean peak viable cell density (VCD) of from about $6\times10^6$ cells/mL to about $20\times10^6$ cells/mL. In some aspects, the cell viability exhibits a mean peak viable cell density (VCD) of from about $7\times10^6$ cells/mL to about $19\times10^6$ cells/mL. In some aspects, the cell viability exhibits a mean peak viable cell density (VCD) of from about $8\times10^6$ cells/mL to about $18\times10^6$ cells/mL. In some aspects, the cell viability exhibits a mean peak viable cell density (VCD) of from about $9\times10^6$ cells/mL to about $17\times10^6$ cells/mL. In some aspects, the cell viability exhibits a mean peak viable cell density (VCD) of from about $10\times10^6$ cells/mL to about $16\times10^6$ cells/mL In some aspects, the cell viability exhibits a mean peak viable cell density (VCD) of from about $11\times10^6$ cells/mL to about $15\times10^6$ cells/mL. In some aspects, the cell viability exhibits a mean peak viable cell density (VCD) of from about $12\times10^6$ cells/mL to about $14\times10^6$ cells/mL.

In some aspects, the cell viability exhibits a mean peak viable cell density (VCD) of about $6\times10^6$ cells/mL. In some aspects, the cell viability exhibits a mean peak viable cell density (VCD) of about $6\times10^6$ cells/mL. In some aspects, the cell viability exhibits a mean peak viable cell density (VCD) of about $10\times10^6$ cells/mL. In some aspects, the cell viability exhibits a mean peak viable cell density (VCD) of about $10.5\times10^6$ cells/mL In some aspects, the cell viability exhibits a mean peak viable cell density (VCD) of about $11\times10^6$ cells/mL. In some aspects, the cell viability exhibits a mean peak viable cell density (VCD) of about $11.5\times10^6$ cells/mL. In some aspects, the cell viability exhibits a mean peak viable cell density (VCD) of about $12\times10^6$ cells/mL. In some aspects, the cell viability exhibits a mean peak viable cell density (VCD) of about $12.5\times10^6$ cells/mL. In some aspects, the cell viability exhibits a mean peak viable cell density (VCD) of about $13\times10^6$ cells/mL. In some aspects, the cell viability exhibits a mean peak viable cell density (VCD) of about $13.5\times10^6$ cells/mL. In some aspects, the cell viability exhibits a mean peak viable cell density (VCD) of about $14\times10^6$ cells/mL. In some aspects, the cell viability exhibits a mean peak viable cell density (VCD) of about $14.5\times10^6$ cells/mL. In some aspects, the cell viability exhibits a mean peak viable cell density (VCD) of about $15\times10^6$ cell s/mL.

The methods of the present disclosure are also useful for improving or controlling a cell viability after a mean 0-14 day integral of viable cell density (IVCD). The IVCD measure is an alternate way of measuring production of an upstream process, as opposed to the instantaneous measure of viable cell density. Since each cell has a variable protein production lifetime and various cell culture conditions affect viable cell rates over time, the IVCD is useful to estimate the total production of protein product over the time of the entire process. In some aspects, the cell viability exhibits a mean 0-14 day integral of viable cell density (IVCD) of from about $0.05\times10^9$ cells/mL to about $0.2\times10^9$ cells/mL. In some aspects, the cell viability exhibits a mean 0-14 day integral of viable cell density (IVCD) of from about $0.1\times10^9$ cells/mL to about $0.15\times10^9$ cells/mL. In some aspects, the cell viability exhibits a mean 0-14 day integral of viable cell density (IVCD) of from about $0.05\times10^9$ cells/mL to about $0.15\times10^9$ cells/mL. In some aspects, the cell viability exhibits a mean 0-14 day integral of viable cell density (IVCD) of from about $0.05\times10^9$ cells/mL to about $0.1\times10^9$ cells/mL. In some aspects, the cell viability exhibits a mean 0-14 day integral of viable cell density (IVCD) of from about $0.09\times10^9$ cells/mL to about $0.13\times10^9$ cells/mL. In some aspects, the cell viability exhibits a mean 0-14 day integral of viable cell density (IVCD) of from about $0.09\times10^9$ cells/mL to about $0.11\times10^9$ cells/mL.

The methods of the present disclosure are also useful for controlling the protein titer. In some aspects, the titer is measured after a period of about 14 days. In some aspects, the titer exhibits a mean day 14 titer of from about 1.5 g/L to about 3.5 g/L. In some aspects, the titer exhibits a mean day 14 titer of from about 1.5 g/L to about 3 g/L. In some aspects, the titer exhibits a mean day 14 titer of from about 2 g/L to about 3 g/L. In some aspects, the titer exhibits a mean day 14 titer of from about 2 g/L to about 2.5 g/L. In some aspects, the titer exhibits a mean day 14 titer of from about 2.5 g/L to about 3 g/L. In some aspects, the titer exhibits a mean 14 day titer of about 2 g/L. In some aspects, the titer exhibits a mean 14 day titer of about 2.5 g/L. In some aspects, the titer exhibits a mean 14 day titer of about 2.8 g/L. In some aspects, the titer exhibits a mean 14 day titer of about 2.87 g/L. In some aspects, the titer exhibits a mean 14 day titer of about 2.9 g/L. In some aspects, the titer exhibits a mean 14 day titer of about 3 g/L. In some aspects, the titer exhibits a mean 14 day titer of about 3.5 g/L.

The methods of the present disclosure are also useful for controlling the protein production of cells, as measured by individual cell output production. Measuring output via individual cell output production is useful to monitor the cell health as a function of reactor conditions. In some aspects, the titer exhibits a mean specific productivity of from about 20 pg/cell-day to about 45 pg/cell-day. In some aspects, the titer exhibits a mean specific productivity of from about 20 pg/cell-day to about 40 pg/cell-day. In some aspects, the titer exhibits a mean specific productivity of from about 30 pg/cell-day to about 45 pg/cell-day. In some aspects, the titer exhibits a mean specific productivity of from about 20 pg/cell-day to about 35 pg/cell-day. In some aspects, the titer exhibits a mean specific productivity of from about 25 pg/cell-day to about 35 pg/cell-day. In some aspects, the titer exhibits a mean specific productivity of from about 25 pg/cell-day to about 30 pg/cell-day. In some aspects, the titer exhibits a mean specific productivity of from about 30 pg/cell-day to about 40 pg/cell-day. In some aspects, the titer exhibits a mean specific productivity of from about 30 pg/cell-day to about 35 pg/cell-day. In some aspects, the titer exhibits a mean specific productivity of about 20 pg/cell-day. In some aspects, the titer exhibits a mean specific productivity of about 25 pg/cell-day. In some aspects, the titer exhibits a mean specific productivity of about 30 pg/cell-day. In some aspects, the titer exhibits a mean specific productivity of about 31 pg/cell-day. In some aspects, the titer exhibits a mean specific productivity of about 32 pg/cell-day. In some aspects, the titer exhibits a mean specific productivity of about 33 pg/cell-day.

In some aspects, the titer exhibits a mean specific productivity of about 34 pg/cell-day. In some aspects, the titer exhibits a mean specific productivity of about 35 pg/cell-day. In some aspects, the titer exhibits a mean specific productivity of about 36 pg/cell-day. In some aspects, the titer exhibits a mean specific productivity of about 37 pg/cell-day. In some aspects, the titer exhibits a mean specific productivity of about 38 pg/cell-day. In some aspects, the titer exhibits a mean specific productivity of about 39 pg/cell-day. In some aspects, the titer exhibits a mean specific productivity of about 40 pg/cell-day. In some aspects, the titer exhibits a mean specific productivity of about 41 pg/cell-day. In some aspects, the titer exhibits a mean specific productivity of about 42 pg/cell-day. In some aspects, the titer exhibits a mean specific productivity of about 45 pg/cell-day.

The methods of the present disclosure can be utilized via the growth of cells in a vessel using an energy source. In some aspects, the vessel is a bioreactor and comprises a feed media comprising glucose or galactose. In some aspects, the cells are mammalian cells. In some aspects, the cells are eukaryotic cells. In some aspects, the cells are mammalian cells. In some aspects, the cells are selected from Chinese hamster ovary (CHO) cells, HEK293 cells, mouse myeloma (NS0), baby hamster kidney cells (BHK), monkey kidney fibroblast cells (COS-7), Madin-Darby bovine kidney cells (MDBK), and any combination thereof. In one aspect, the cells are Chinese hamster ovary cells. In some aspects, the cells are insect cells, e.g., *Spodoptera frugiperda* cells. In other aspects, the cells are mammalian cells. Such mammalian cells include but are not limited to CHO, VERO, BHK, Hela, MDCK, HEK 293, NIH 3T3, W138, BT483, Hs578T, HTB2, BT2O and T47D, NS0, CRL7O3O, COS (e.g., COS 1 or COS), PER.C6, VERO, HsS78 Bst, HEK-293T, HepG2, SP210, R1.1, B-W, L-M, BSC1, BSC40, YB/20, BMT10 and HsS78 Bst cells. In some aspects, the mammalian cells are CHO cells. In some aspects the CHO cell is CHO-DG44, CHOZN, CHO/dhfr−, CHOK1SV GS-KO, or CHO-S. In some aspects, the CHO cell is CHO-DG4. In some aspects, the CHO cell is CHOZN. Other suitable CHO cell lines disclosed herein include CHO-K (e.g., CHO K1), CHO pro3-, CHO P12, CHO-K1/SF, DUXB11, CHO DUKX; PA-DUKX; CHO pro5; DUK-BII or derivatives thereof.

IIA. Temperature

The temperature of a production vessel such as a bioreactor can be an important aspect of bioproduction because the temperature of the bioreactor plays a role in cell growth, viable cell density, cell longevity and/or glycosylation activity of glycosylating enzymes inside a cell. Temperature changes can significantly affect the rate of enzymatic reactions within the cell, denature proteins, and/or cause other effects on a cell culture. Cells can be cultured at an initial temperature set point such as 37° C., for example, to encourage maximum viable cell density, and then the temperature can be modified to another temperature set point (i.e., a second temperature set point or a final temperature set point) to prolong cell longevity or to enhance desired glycosylation activity within the cell. One or more temperature set points can be used during the various phases of an upstream production process to improve the overall cell density, protein yield, or protein glycosylation profile of a protein of interest. In some aspects, the methods are directed to one or more temperature adjustments during protein production. Temperature adjustments can be a decrease of operating temperature during a manufacturing process. Temperature adjustments can also be an increase of operating temperature during a manufacturing process. In some aspects, the methods of the present disclosure use at least one, at least two, at lease three, or at least four temperature adjustments during a manufacturing process.

The methods of the present disclosure are also related to controlling cell growth rate, cell viability, viable cell density and/or titer of cells for producing a protein. The initial temperature set point is important for creating reactor conditions conducive to cellular expansion and growth of the cells during the log growth phase. After the initial log phase, a second temperature set point that is lower than the initial set point is used to reduce the cellular expansion conditions to prevent overgrowth of the cell culture, which would lead to undesirable cell densities and a subsequent loss in total cell viability. In some aspects, the methods of the present disclosure involve culturing the cells in a bioreactor for an induction phase under an initial temperature set point of 36° C., subsequently culturing the cells in a second temperature set point of 33° C., and finally culturing the cells at a final temperature set point of 31° C. In some aspects, the methods of the present disclosure use at least two, at least three, at least four, or at least five temperature set points, e.g., an initial temperature set point, a final set point, or more set points after the initial temperature set point but before the final set point. In some aspects, the methods of the present disclosure use at least three temperature set points, i.e., an initial temperature set point, a second temperature set point, and a final temperature set point.

In some aspects, the initial temperature set point for the present method is about 37° C. and a second temperature set point is lower than about 36° C. In some aspects, the initial temperature set point is about 36° C. and a second temperature set point is lower than the first temperature set point, e.g., about 35° C., about 34° C., about 33° C., about 32° C., or about 31° C. In some aspects, the initial temperature set point is about 37° C. and a second temperature set point is lower than about 34° C. In some aspects, the initial temperature set point is about 36° C. and a second temperature set point is lower than about 35° C., about 34° C., or about 33° C. In some aspects, the initial temperature set point is lower than about 36.5° C. and the final temperature set point is about 31° C. In some aspects, the initial temperature set point is about 36.0° C. and the final temperature set point is about 31° C. In some aspects, the initial temperature set point is lower than about 35.5° C. and the final temperature set point is about 31° C. In some aspects, the initial temperature set point is lower than about 35.0° C. and the final temperature set point is about 31° C. In some aspects, the initial temperature set point is lower than about 36.5° C., a second temperature set point is about 33° C., and a final temperature set point is lower than about 33° C. or about 32° C. In some aspects, the initial temperature set point is about 36.0° C., a second temperature set point is about 33° C., and a final temperature set point is lower than about 33° C. or about 32° C. In some aspects, the initial temperature set point is about 36.0° C., a second temperature set point is about 33° C., and a final temperature set point is lower than about 32° C. In some aspects, the initial temperature set point is about 36.0° C., a second temperature set point is about 33° C., and a final temperature set point is about 31° C.

The methods of the present disclosure can comprise an initial temperature set point, a second temperature set point, and a third and/or final set point. The initial, second, and third and/or final temperature set points are used to further control steady-state cell density during a manufacturing process, control viable cell percentages, manage cell-cycle divisions of the culture, and/or alter the glycosylation rates and glycosylation profile of produced proteins. In some aspects, the third temperature set point is lower than the second temperature set point. In some aspects, the initial temperature set point is a temperature between 37° C. and 34° C., e.g., 37° C., 36° C., 35° C., or 34° C.; the second temperature set point is a temperature between 34° C. and 32° C., e.g., 34° C., 33° C., or 32° C.; and the final temperature set point is a temperature between 32° C. and 30° C., e.g., 32° C., 31° C., or 30° C., wherein the second temperature set point is lower than the first temperature set point and the final temperature set point is lower than the second temperature set point. In some aspects, the initial temperature set point is a temperature between 37° C. and 34° C., e.g., 37° C., 36° C., 35° C., or 34° C.; the second temperature set point is a temperature between 34° C. and 32° C., e.g., 34° C., 33° C., or 32° C.; and the final temperature set point is a temperature between 32° C. and 30° C., e.g., 32° C., 31° C., or 30° C., wherein the first temperature set point is not 37° C., the second temperature set point is not 34° C., and/or the final temperature set point is not 32° C.

The methods of the present disclosure can comprise an initial temperature set point, a second temperature set point, a third temperature set point, and optionally a fourth temperature set point, optionally a fifth temperature set point, and optionally a sixth temperature setpoint. These fourth, fifth, and sixth temperature set points are used to further control steady-state cell density during a manufacturing process, control viable cell percentages, manage cell-cycle divisions of the culture, and/or alter the glycosylation rates and glycosylation profile of produced proteins. In some aspects, the methods further comprise setting an optional fourth temperature set point, an optional fifth temperature set point, an optional sixth temperature set point, wherein the optional fourth temperature set point, the fifth temperature set point, and/or the sixth temperature set point are lower than the third temperature set point. In some aspects, the methods further comprises setting an optional fourth temperature set point, an optional fifth temperature set point, and an optional sixth temperature set point, wherein the optional fourth temperature set point, the fifth temperature set point, and/or the sixth temperature set point are higher than the third temperature set point In some aspects, the fourth, fifth, or sixth temperature set point, the fifth temperature set point, and/or the sixth temperature set point is about 30° C., about 31° C., about 32° C., about 33° C., about 34° C., about 35° C., about 36° C., about 37° C., about 38° C., about 39° C., or about 40° C. In some aspects, the fourth, fifth, or sixth temperature set point, the fifth temperature set point, and/or the sixth temperature set point is about 30° C. In some aspects, the fourth, fifth, or sixth temperature set point is about 31° C. In some aspects, the fourth, fifth, or sixth temperature set point is about 32° C. In some aspects, the fourth, fifth, or sixth temperature set point is about 33° C. In some aspects, the fourth, fifth, or sixth temperature set point is about 34° C. In some aspects, the fourth, fifth, or sixth temperature set point is about 35° C. In some aspects, the fourth, fifth, or sixth temperature set point is about 36° C. In some aspects, the fourth, fifth, or sixth temperature set point is about 37° C. In some aspects, the fourth, fifth, or sixth temperature set point is about 38° C. In some aspects, the fourth, fifth, or sixth temperature set point is about 39° C. In some aspects, the fourth, fifth, or sixth temperature set point is about 40° C.

Apart from the temperature set points, the methods of the present disclosure also involve modification of the timing of the temperature set points to carry out a temperature shift within a specific time window. The timing of the temperature shift is important to control the cell density, cell growth, and protein production characteristics of the cell culture during the upstream process. In some aspects, the methods of the present disclosure are related to a method of improving the yield of a protein by cells, comprising culturing the cells in a bioreactor under suitable conditions, wherein the suitable conditions comprise (i) an initial temperature set point of 36.0° C. and a second temperature set point lower than 36° C.; (ii) an initial temperature set point lower than 36.5° C. and a final temperature set point of 31° C.; or (iii) an initial temperature set point lower than 36.5° C., a second temperature set point of 33° C., and a final temperature set point lower than 33° C. In some aspects, the methods of the present disclosure are related to a method of improving the yield of a protein by cells, comprising culturing the cells in a bioreactor under suitable conditions, wherein the suitable conditions comprise (i) an initial temperature set point of 36.0° C. and a second temperature set point lower than 34° C.; (ii) an initial temperature set point lower than 36.5° C. and a final temperature set point of 31° C.; or (iii) an initial temperature set point lower than 36.5° C., a second temperature set point of 32° C., and a final temperature set point lower than 32° C.

In some aspects, the cells are cultured in a bioreactor under suitable conditions, comprising (i) an initial temperature set point higher than 35° C. but lower than 37° C. and a second temperature set point higher than 32° C. but lower than 34° C., (ii) an initial temperature set point higher than 35.5° C. but lower than 37.5° C. and a second temperature set point higher than 32° C. but lower than 34° C., and (iii) an initial temperature set point higher than 35° C. but lower than 37° C., a second temperature set point higher than 32° C. but lower than 34° C., and a final temperature set point higher than 30° C. but lower than 32° C.

The methods of the present disclosure are also useful for improving yield of a protein by cells by adjusting the temperature set point in the bioreactor after an initial temperature set point. In some aspects, the initial temperature set point is higher than about 35° C. and lower than 37° C., e.g., about 36° C., the second temperature set point is higher than about 32° C. and lower than about 34° C., about 33° C., and the third temperature set point is higher than about 30° C. and lower than about 32° C., e.g., about 31° C., wherein the second temperature set point occurs at about 120 hours to about 168 hours, e.g., about 5 days, about 6 days, or about 7 days, after the initial temperature set point. In some aspects, the initial temperature set point is higher than about 35° C. and lower than 37° C., e.g., about 36° C., the second temperature set point is higher than about 32° C. and lower than about 34° C., about 33° C., and the third temperature set point is higher than about 30° C. and lower than about 32° C., e.g., about 31° C., wherein the second temperature set point occurs at about 120 hours, about 126 hours, about 132 hours, about 138 hours, about 144 hours, about 150 hours, about 156 hours, about 162 hours, or about 168 hours after the initial temperature set point.

In some aspects, the initial temperature set point is higher than about 35° C. and lower than 37° C., e.g., about 36° C., the second temperature set point is higher than about 32° C. and lower than about 34° C., about 33° C., and the third temperature set point is higher than about 30° C. and lower than about 32° C., e.g., about 31° C., wherein the second temperature set point occurs at about 120 hours, 5 days, after the initial temperature set point. In some aspects, the initial temperature set point is higher than about 35° C. and lower than 37° C., e.g., about 36° C., the second temperature set point is higher than about 32° C. and lower than about 34° C., about 33° C., and the third temperature set point is higher than about 30° C. and lower than about 32° C., e.g., about 31° C., wherein the second temperature set point occurs at about 144 hours, 6 days, after the initial temperature set point. In some aspects, the initial temperature set point is higher than about 35° C. and lower than 37° C., e.g., about 36° C., the second temperature set point is higher than about 32° C. and lower than about 34° C., about 33° C., and the third temperature set point is higher than about 30° C. and lower than about 32° C., e.g., about 31° C., wherein the second temperature set point occurs at about 168 hours, 7 days, after the initial temperature set point. In some aspects, the second temperature set point occurs at about 192 hours, e.g., 8 days, after the initial temperature set point.

The methods of the present disclosure are also used to control the transition timing to the final temperature set point. In some aspects, the initial temperature set point is higher than about 35° C. and lower than 37° C., e.g., about 36° C., the second temperature set point is higher than about 32° C. and lower than about 34° C., about 33° C., and the final temperature set point is higher than about 30° C. and lower than about 32° C., e.g., about 31° C., wherein the final temperature set point occurs at from about 168 hours to about 312 hours, about 7 days, about 8 days, about 9 days, about 10 days, about 11 days, about 12 days, or about 13 days, after the initial temperature set point, from 7 days to 12 days, from 8 days to 13 days, from 9 days to 13 days, from 8 days to 12 days, from 8 days to 11 days. In some aspects, the initial temperature set point is higher than about 35° C. and lower than 37° C., e.g., about 36° C., the second temperature set point is higher than about 32° C. and lower than about 34° C., about 33° C., and the final temperature set point is higher than about 30° C. and lower than about 32° C., e.g., about 31° C., wherein the final temperature set point occurs at from about 192 hours to about 300 hours. In some aspects, the final temperature set point occurs at from about 216 hours to about 288 hours. In some aspects, the final temperature set point occurs at from about 216 hours to about 264 hours.

IIB. pH

In one aspect, the methods of the present disclosure involve improving or controlling protein production by modifying pH of the process. The regulation of intracellular pH is a fundamental physiological process of great significance to the growth and metabolism of cells. Since intracellular pH has wide ranging consequences for the transport of nutrients and hormones, and for enzymatic reactions in the cells, cells devote a lot of energy to the regulation of cytoplasmic pH. Furthermore, pH plays a role in the glycosylation rates and profiles of protein produced by the cell.

In some aspects, modifying pH can be done by using more than one pH set point, more than two pH set points, more than three pH set points, more than four pH set points or more than five pH set points during the culturing process. In some aspects, modifying pH uses an initial pH set point and a second pH set point. In some aspects, modifying pH uses an initial pH set point, a second pH set point, and a third pH set point. In some aspects, modifying pH comprises decreasing pH during the culturing process. In some aspects, modifying pH comprises decreasing pH at least by about 0.5, at least by about 1.0, at least by about 1.5, at least by about 2.0, at least by about 0.1, at least by about 0.2, at least by about 0.3, or at least by about 0.4. In some aspects, modifying pH comprises decreasing pH at least by about 0.1. In some aspects, modifying pH comprises decreasing pH at least by about 0.2. In some aspects, modifying pH comprises decreasing pH at least by about 0.5. In some aspects, modifying pH comprises decreasing pH at least by about 1. In some aspects, modifying pH comprises decreasing pH at least by about 1.5. In some aspects, modifying pH comprises decreasing pH at least by about 2.

In some aspects, the initial pH set point is pH 7.0 and the second pH set point is 6.9. In some aspects, the initial pH is 7.0. In some aspects, the initial pH set point is 6. In some aspects, the initial pH set point is 6.1. In some aspects, the initial pH set point is 6.2. In some aspects, the initial pH set point is 6.3. In some aspects, the initial pH set point is 6.4. In some aspects, the initial pH set point is 6.5. In some aspects, the initial pH set point is 6.6. In some aspects, the initial pH set point is 6.7. In some aspects, the initial pH set point is 6.8. In some aspects, the initial pH set point is 6.9. In some aspects, the initial pH set point is 7. In some aspects, the second pH set point is 6. In some aspects, the second pH set point is 6.1. In some aspects, the second pH set point is 6.2. In some aspects, the second pH set point is 6.3. In some aspects, the second pH set point is 6.4. In some aspects, the second pH set point is 6.5. In some aspects, the second pH set point is 6.6. In some aspects, the second pH set point is 6.7. In some aspects, the second pH set point is 6.8. In some aspects, the second pH set point is 6.9. In some aspects, the second pH set point is 7. In some aspects, the third pH set point is 6. In some aspects, the third pH set point is 6.1. In some aspects, the third pH set point is 6.2. In some aspects, the third pH set point is 6.3. In some aspects, the third pH set point is 6.4. In some aspects, the third pH set point is 6.5. In some aspects, the third pH set point is 6.6. In some aspects, the third pH set point is 6.7. In some aspects, the third pH set point is 6.8. In some aspects, the third pH set point is 6.9. In some aspects, the third pH set point is 7. In some aspects, the initial pH is 7.0 and the second pH is 6.9. In some aspects, the initial pH is 7.1 and the second pH is 6.8. In some aspects, the initial pH is 7.1 and the second pH is 6.9. In some aspects, the initial pH is 7.1 and the second pH is 7.0. In some aspects, the initial pH is 6.9 and the second pH is 6.8. In some aspects, the initial pH is 6.9 and the second pH is 6.7.

Not only is the pH of the upstream production process important, the timing of any pH shift during production also plays a significant role in the process. A pH shift during production leads to alterations in the process performance mainly due to effects on cell growth and metabolism. The methods of the present disclosure are related to shifting the pH during protein production to control the glycosylation of the proteins. In some aspects, the pH is shifted to a pH of about 6.0. In some aspects, the pH is shifted to a pH of about 6.1. In some aspects, the pH is shifted to a pH of about 6.2. In some aspects, the pH is shifted to a pH of about 6.3. In some aspects, the pH is shifted to a pH of about 6.4. In some aspects, the pH is shifted to a pH of about 6.5. In some aspects, the pH is shifted to a pH of about 6.6. In some aspects, the pH is shifted to a pH of about 6.7. In some aspects, the pH is shifted to a pH of about 6.8. In some aspects, the pH is shifted to a pH of about 6.9. In some aspects, the pH is shifted to a pH of about 7.0. In some aspects, the pH is shifted to a pH of about 7.1. In some aspects, the pH is shifted to a pH of about 7.2. In some aspects, the pH is shifted to a pH of about 7.3. In some aspects, the pH is shifted to a pH of about 7.4. In some aspects, the pH is shifted to a pH of about 7.5.

The time after culture induction in which the pH is adjusted (referred hereafter as "pH shift" or "pH timing") during production also leads to alterations in the process due to effects of cell growth and metabolism. The methods of the present disclosure are related to shifting the pH during protein production to control glycosylation of the proteins. In some aspects, the pH shift is from about 50 hours to about 150 hours after induction. In some aspects, the pH shift is from about 72 hours to about 120 hours after induction. In some aspects, the pH shift is from about 80 hours to about 100 hours after induction. In some aspects, the pH shift is about 90 hours after induction. In some aspects, the pH shift is about 100 hours after induction. In some aspects, the pH shift is about 96 hours after induction.

IIC. Viable Cell Density

The initial viable cell density (VCD) or seed density of cells at the outset of a bioreactor process can be an important aspect of the upstream growth process as the initial viable cell density (VCD) impacts the steady-state and/or maximum viable cell density of the cell culture during production. A higher initial cell density can lead to a much higher number of cells produced during the initial growth phase of the upstream process, and can ultimately lead to faster cellular death and a shorter bioreactor run time. The bioreactor production process can be shortened, but in some cases, the post-translational modifications made to proteins produced by the process can be affected, as a shorter bioreactor run time can lead to altered residence time of the proteins in the Golgi, and therefore altered post-translational modifications, such as changes to the glycosylation pattern of the protein. Because of the wide implications that the initial cell density can have on the overall yield and quality output of the protein, the initial viable cell density is an important parameter for upstream protein production.

In some aspects, the methods of the present disclosure involve seeding a bioreactor with an initial viable cell density (VCD). In some aspects, the initial viable cell density (VCD) set point is between about $0.05\times10^6$ cells/mL and about $0.95\times10^6$ cells/mL. In some aspects, the initial viable cell density (VCD) set point is between about $0.05\times10^6$ cells/mL and about $0.9\times10^6$ cells/mL. In some aspects, the initial viable cell density (VCD) set point is between about $0.05\times10^6$ cells/mL and about $0.85\times10^6$ cells/mL. In some aspects, the initial viable cell density (VCD) set point is between about $0.05\times10^6$ cells/mL and about $0.8\times10^6$ cells/mL. In some aspects, the initial viable cell density (VCD) set point is between about $0.05\times10^6$ cells/mL and about $0.75\times10^6$ cells/mL. In some aspects, the initial viable cell density (VCD) set point is between about $0.05\times10^6$ cells/mL and about $0.7\times10^6$ cells/mL. In some aspects, the initial viable cell density (VCD) set point is between about $0.05\times10^6$ cells/mL and about $0.65\times10^6$ cells/mL. In some aspects, the initial viable cell density (VCD) set point is between about $0.1\times10^6$ cells/mL and about $0.6\times10^6$ cells/mL. In some aspects, the initial viable cell density (VCD) set point is between about $0.15\times10^6$ cells/mL and about $0.6\times10^6$ cells/mL. In some aspects, the initial viable cell density (VCD) set point is between about $0.15\times10^6$ cells/mL and about $0.55\times10^6$ cells/mL. In some aspects, the initial viable cell density (VCD) set point is between about $0.15\times10^6$ cells/mL and about $0.5\times10^6$ cells/mL. In some aspects, the initial viable cell density (VCD) set point is between about $0.15\times10^6$ cells/mL and about $0.45\times10^6$ cells/mL. In some aspects, the initial viable cell density (VCD) set point is between about $0.15\times10^6$ cells/mL and about $0.4\times10^6$ cells/mL. In some aspects, the initial viable cell density (VCD) set point is between about $0.2\times10^6$ cells/mL and about $0.4\times10^6$ cells/mL. In some aspects, the initial viable cell density (VCD) set point is between about $0.2\times10^6$ cells/mL and about $0.35\times10^6$ cells/mL. In some aspects, the initial viable cell density (VCD) set point is between about $0.25\times10^6$ cells/mL and about $0.35\times10^6$ cell s/mL.

IID. Cell Feed Time

The methods of the present disclosure can also be achieved through altering a cell feed time to affect or control growth conditions of the cells. The timing of a feeding process is important to produce the desired growth properties of a cell culture production process, such as cell density. The optimal feeding strategy in bioreactors depends on the structure of the reaction kinetics and the interaction between the different reactions, such as protein synthesis and post-translational modification of those proteins (i.e., glycosylation). Both overfeeding and underfeeding a cellular population are detrimental to cell growth and product formation, and therefore the timing of the feeds can be important to ensure maximum product yield. Underfeeding of cultures can lead to nutrient depletion and cell death, while overfeeding can lead to an excess of nutrients, an increase in osmolality and cellular stress in dense cellular environments, and undesirable post-translational modifications of a protein of interest.

In some aspects, the cell feed time is from about 24 hours to about 100 hours after induction. In some aspects, the cell feed time is from about 48 hours to about 100 hours after induction. In some aspects, the cell feed time is from about 48 hours to about 72 hours after induction. In some aspects, the cell feed time is from about 48 hours to about 96 hours after induction. In some aspects, the cell feed time is from about 72 hours to about 96 hours after induction. In some aspects, the cell feed time is about 24 hours after induction. In some aspects, the cell feed time is about 48 hours after induction. In some aspects, the cell feed time is about 72 hours after induction. In some aspects, the cell feed time is about 96 hours after induction.

IIE. $CO_2$

The methods of the present disclosure are also related to an initial $CO_2$ set point. The concentration of $CO_2$ in an upstream bioreactor process is an important element to control cellular growth and pH. High concentrations of $CO_2$ can lead to additional $CO_2$ dissolved in the cell culture medium which would lower the pH of the cell culture medium. Furthermore, the concentration of $CO_2$ will likely change during an upstream biomanufacturing process because carbon dioxide is the inevitable product of respiration processes and as such always present in aerobic bioprocesses. High concentrations of $CO_2$ during manufacturing can lead to reductions in the growth rate of the cell culture and/or the protein production output. Protein glycosylation patterns are also affected by changes in $CO_2$ concentration as changes to protein production rates can affect protein residence time in the Golgi.

In some aspects, the initial $CO_2$ set point is between about 5% and about 50%, between about 10% and about 45%, between about 10% and about 40%, between about 10% and about 35%, between about 10% and about 30%, between about 15% and about 30%, between about 15% and about 25%, or between about 20% and about 25 In some aspects, the initial $CO_2$ set point is between about 0% and about 75%. In some aspects, the initial $CO_2$ set point is between about 5% and about 50%. In some aspects, the initial $CO_2$ set point is between about 10% and about 45%. In some aspects, the initial $CO_2$ set point is between about 10% and about 40%. In some aspects, the initial $CO_2$ set point is between about 10% and about 35%. In some aspects, the initial $CO_2$ set point is between about 10% and about 30%. In some aspects, the initial $CO_2$ set point is between about 15% and about 30%. In some aspects, the initial $CO_2$ set point is between about 15% and about 25%. In some aspects, the initial $CO_2$ set point is between about 10% and about 25%. In some aspects, the initial $CO_2$ set point is about 15% about 16%, about 17% (e.g., 16.8%), about 18%, about 19%, about 20%, about 21%, about 22%, about 23%, about 24%, or about 25%. In some aspects, the initial $CO_2$ set point is about 17% (e.g., 16.8%). In some aspects, the initial $CO_2$ set point is about 22%, e.g., 22.4%. In some aspects, the initial $CO_2$ set point is about 23%.

In some aspects, the initial $CO_2$ concentration is monitored and maintained throughout the cell culturing process. In other aspects, the initial $CO_2$ concentration is set, but is not monitored throughout the cell culturing process.

IIF. Combination of Conditions

In some aspects, the methods of the present disclosure comprise any combination of the above listed conditions. In some aspects, the methods comprise two or more conditions selected from the group consisting of: (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C.; (ii) an initial pH set point of pH 7.0 and a second pH set point of 6.9; (iii) an initial viable cell density (VCD) set point between about $0.15\times10^6$ cells/mL and about $0.45\times10^6$ cells/mL; (iv) an initial pH of 6.9; (v) a pH shift at about 96 hours; and (vi) an initial $CO_2$ set point between about 15% and about 25%, e.g., about 16.8%.

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C. and (ii) an initial pH set point of pH 7.0 and a second pH set point of 6.9.

In some aspects, the methods comprise (i) an initial temperature set point of 36° C., a second temperature set point of 33° C., and a third temperature set point of 31° C. and (ii) an initial viable cell density (VCD) set point of from about $0.15\times10^6$ cells to about $0.45\times10^6$ cells (e.g., $0.30\times10^6$ cells).

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C. and (ii) an initial $CO_2$ set point between about 15% and about 25%, e.g., about 15%, about 16%, about 16.8%, about 17%, about 22%, or about 22.4%.

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., (ii) an initial pH set point of pH 7.0 and a second pH set point of 6.9, and (iii) an initial viable cell density (VCD) set point of from about $0.15\times10^6$ cells to about $0.45\times10^6$ cells (e.g., $0.30\times10^6$ cells).

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., and (ii) an initial pH set point of pH 6.9.

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., (ii) an initial pH set point of pH 6.9, and (iii) an initial viable cell density (VCD) set point of from about $0.15\times10^6$ cells to about $0.45\times10^6$ cells (e.g., $0.30\times10^6$ cells).

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., (ii) an initial pH set point of pH 7.0 and a second pH set point of pH 6.9, or an initial pH set point of pH 6.9, and (iii) an initial $CO_2$ set point between about 15% and about 25%, e.g., about 15%, about 16%, about 16.8%, about 17%, about 22%, or about 22.4%.

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., (ii) an initial pH set point of pH 7.0 and a second pH set point of pH 6.9, or an initial pH set point of pH 6.9, (iii) an initial viable cell density (VCD) set point of from about $0.15\times10^6$ cells to about $0.45\times10^6$ cells (e.g., $0.30\times10^6$ cells); and (iv) an initial $CO_2$ set point between about 15% and about 25%, e.g., about 15%, about 16%, about 16.8%, about 17%, about 22%, or about 22.4%.

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., (ii) an initial pH set point of pH 7.0 and a second pH set point of pH 6.9, or an initial pH set point of pH 6.9, (iii) an initial $CO_2$ set point between about 15% and about 25%, e.g., about 15%, about 16%, about 16.8%, about 17%, about 22%, or about 22.4%, and (iv) an initial viable cell density (VCD) set point of from about $0.15\times10^6$ cells to about $0.45\times10^6$ cells (e.g., $0.30\times10^6$ cells).

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., (ii) an initial pH set point of pH 7.0 and a second pH set point of pH 6.9, or an initial pH set point of pH 6.9, wherein the shift from the initial pH set point to the second pH set point is at about 96 hours; and (iii) an initial $CO_2$ set point between about 15% and about 25%, e.g., about 15%, about 16% (e.g., about 16.8%), about 17%, about 22%, or about 22.4%.

In some aspects, the methods comprise (i) an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., (ii) an initial pH set point of pH 7.0 and a second pH set point of pH 6.9, wherein the shift from the initial pH set point to the second pH set point is at about 96 hours; and (iii) an initial $CO_2$ set point between about 15% and about 25%, e.g., about 15%, about 16%, about 16.8%, about 17%, about 22%, or about 22.4%; and (iv) an initial viable cell density (VCD) set point of from about $0.15 \times 10^6$ cells to about $0.45 \times 10^6$ cells (e.g., $0.30 \times 10^6$ cells).

III. Glycosylation Profile

The methods and conditions of the present disclosure are useful for affecting, maintaining, controlling, and/or modifying the glycosylation profile of a protein produced by the present methods. In some aspects, the method controls a glycosylation profile of the protein. In some aspects, the glycosylation profile of the protein comprises one or more N-linked glycans.

The methods of the present disclosure can be achieved or substantiated via glycan analysis using a variety of methods, including a glycan release assay. The first step in glycan analysis of glyco-conjugates such as glycoproteins is the release of the sugars from the molecules to which they are attached. N-linked glycans on a glycoprotein can be released by an amidase such as Peptide-N-glycosidase F (PNGase F). Most methods for the analysis of oligosaccharides from biological sources require a glycan derivatization step: glycans can be derivatized to introduce a chromophore or fluorophore, facilitating detection after chromatographic or electrophoretic separation. Derivatization can also be applied to link charged or hydrophobic groups at the reducing end to enhance glycan separation and mass-spectrometric detection. Moreover, derivatization steps such as permethylation aim at stabilizing sialic acid residues, enhancing mass-spectrometric sensitivity, and supporting detailed structural characterization by (tandem) mass spectrometry.

Mass spectrometry ("MS" or "mass-spec") is an analytical technique used to measure the mass-to-charge ratio ions. This is achieved by ionizing the sample and separating ions of differing masses and recording their relative abundance by measuring intensities of ion flux. A typical mass spectrometer comprises three parts: an ion source, a mass analyzer, and a detector system. The ion source is the part of the mass spectrometer that ionizes the substance under analysis (the analyte). The ions are then transported by magnetic or electric fields to the mass analyzer that separates the ions according to their mass-to-charge ratio (m/z). Many mass spectrometers use two or more mass analyzers for tandem mass spectrometry (MS/MS). The detector records the charge induced or current produced when an ion passes by or hits a surface. A mass spectrum is the result of measuring the signal produced in the detector when scanning m/z ions with a mass analyzer.

In some aspects, N-linked glycans can be analyzed by hydrophobic interaction liquid chromatography (HILIC). Glycans can be cleaved from CTLA4, fluorescently labeled, and separated by HILIC for analysis. Tagging the glycans with a fluorescent label (e.g., 2-aminobenzamide) allows the glycans to be detected at femtomole levels. In some aspects, CTLA4 N-linked glycans are analyzed by HILIC coupled to mass spectrometry.

A variety of N-linked glycans can be present in the glycosylation profile of a protein. In some aspects, the N-linked glycans comprise G0F, G1F, G2F, S1G1F, S1G2F, S2G2F, S1G3F, and/or S2G4F. Representative diagrams of G0F, G1F, G2F, S1G1F, S2G2F, S1G3F, and S2G4F can be seen in FIGS. 1B-1C. In some aspects, the methods of the present disclosure involve measuring the glycosylation profile after day 1, day 2, day 3, day 4, day 5, day 6, day 7, day 8, day 9, day 10, day 11, day 12, day 13, day 14, day 15, day 16, day 17, day 18, day 9, day 20, or day 21. In some aspects, the methods of the present disclosure involve measuring the glycosylation profile after day 7. In some aspects, the methods of the present disclosure involve measuring the glycosylation profile after day 14. In some aspects, the methods of the present disclosure involve measuring the glycosylation profile after day 21.

In some aspects, a glycosylated protein is a CTLA4 protein. A CTLA4 molecule or CTLA4 extracellular domain can be fused to an Fc, wherein the molecule is referred to as CTLA4-Fc or CTLA4-Ig. An "Fc region" (fragment crystallizable region), "Fc domain," or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains; IgM and IgE Fc regions comprise three heavy chain constant domains (CH domains 2-4) in each polypeptide chain. The IgG isotype is divided in subclasses in certain species: IgG1, IgG2, IgG3 and IgG4 in humans, and IgG1, IgG2a, IgG2b and IgG3 in mice. For IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the Kabat numbering scheme. The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally-occurring Fc). The methods of the present disclosure are also useful for producing a protein comprising a CTLA4 domain. The methods of the present disclosure are also useful for producing a CTLA4 domain fused to an Fc portion. In some aspects, the protein is a fusion protein. In some aspects, the fusion protein comprises an Fc portion. In some aspects, the protein is abatacept. In some aspects, the protein comprises a sequence selected from the group consisting of SEQ ID Nos: 1-8. In some aspects, the protein comprises SEQ ID NO: 1. In some aspects, the protein comprises SEQ ID NO: 2. In some aspects, the protein comprises SEQ ID NO: 3. In some aspects, the protein comprises SEQ ID NO: 4. In some aspects, the protein comprises SEQ ID NO: 5. In some aspects, the protein comprises SEQ ID NO: 6. In some aspects, the protein comprises SEQ ID NO: 7. In some aspects, the protein comprises SEQ ID NO: 8.

The CTLA4-Ig fusion protein can comprise one or more mutations. In some aspects, the CTLA4-Ig fusion protein is (a) a CTLA4-Ig fusion protein having an amino acid sequence of SEQ ID NO:8 (methionine at amino acid position 27 and glycine at amino acid position 382); (b) a CTLA4-Ig fusion protein having an amino acid sequence of SEQ ID NO: 5 (methionine at amino acid position 27 and lysine at amino acid position 383); (c) a CTLA4-Ig fusion protein having an amino acid sequence of SEQ ID NO: 7 (alanine at amino acid position 26 and glycine at amino acid position 382); (d) a CTLA4-Ig fusion protein having an amino acid sequence of SEQ ID NO: 4 (alanine at amino acid position 26 and lysine at amino acid position 383); (e) a CTLA4-Ig fusion protein having an amino acid sequence of SEQ ID NO: 6 (methionine at amino acid position 25 and glycine at amino acid position 382); or (f) a CTLA4-Ig fusion protein having an amino acid sequence of SEQ ID NO: 3 (methionine at amino acid position 25 and lysine at amino acid position 383). In some aspects, the CTLA4-Ig fusion proteins are (a) about 90% of the CTLA4-Ig polypeptides comprise an amino acid sequence of SEQ ID NO: 2 beginning with the methionine at residue 27; (b) about 10% of the CTLA4-Ig polypeptides comprise the amino acid sequence of SEQ ID NO: 2 beginning with the alanine at residue number 26; (c) about 4% of the CTLA4-Ig polypeptides comprise the amino acid sequence of SEQ ID NO: 2 ending with the lysine at residue number 383, (d) about 96% of the CTLA4-Ig polypeptides comprise the amino acid sequence of SEQ ID NO: 2 ending with the glycine at residue number 382; and optionally, (e) about less than 1% of the CTLA4-Ig polypeptides comprise the amino acid sequence of SEQ ID NO: 2 beginning with the methionine at residue number 25.

The proteins of the present disclosure have glycosylation sites. Glycosylation is a process involving the addition of complex oligosaccharide structures to a protein at specific sites within the polypeptide chain. Glycosylation of proteins and the subsequent processing of the added carbohydrates can affect protein folding and structure, protein stability, including protein half-life, and functional properties of a protein. Protein glycosylation can be divided into two classes by virtue of the sequence context where the modification occurs, O-linked glycosylation and N-linked glycosylation. O-linked polysaccharides are linked to a hydroxyl group, usually to the hydroxyl group of either a serine or a threonine residue. O-glycans are not added to every serine and threonine residue. O-linked oligosaccharides are usually mono or biantennary, i.e., they comprise one or at most two branches (antennas), and comprise from one to four different kinds of sugar residues, which are added one by one. N-linked polysaccharides are attached to the amide nitrogen of an asparagine. Only asparagines that are part of one of two tripeptide sequences, either asparagine-X-serine or asparagine-X-threonine (where X is any amino acid except proline), are targets for glycosylation. N-linked oligosaccharides can have from one to four branches referred to as mono-, bi-, tri-tetraantennary. In some aspects, the one or more N-linked glycans are located at one or more asparagine residues selected from the group consisting of Asn76 (T5), Asn108 (T7), and/or Asn207 (T14) of abatacept.

In some aspects, the one or more N-linked glycans are located at residue Asn76 (T5) and comprise a relative abundance of G0F between about 2.0% and about 10.0%. In some aspects, the one or more N-linked glycans are located at residue Asn76 (T5) and comprise a relative abundance of G0F between about 2.5% and about 10%, between about 2.5% and about 9.5%, between about 2.5% and about 9%, between about 2.5% and about 8.5%, between about 2.5% and about 8%, between about 2.5% and about 7.5%, about 2.5% and about 7%, between about 2.5% and about 6.5%, between about 3.0% and about 10%, between about 3.0%, about 9.5%, between about 3.0% and about 9%, between about 3.0% and about 8.5%, between about 3.0% and about 8%, between about 3.0% and about 7.5%, between about 3.0% and about 7%, or between about 3.0% and about 6.5%.

In some aspects, the one or more N-linked glycans are located at residue Asn76 (T5) and comprise a relative abundance of G0F between about 3.2% and about 6.6%, between about 3.2% and about 4.6%, or between 3.2% and about 5.6%. In some aspects, the one or more N-linked glycans are located at residue Asn76 (T5) and comprise a relative abundance of G0F between about 3.2% and about 4.6%, In some aspects, the one or more N-linked glycans are located at residue Asn76 (T5) and comprise a relative abundance of G0F between about 3.2% and about 6.6%, In some aspects, the one or more N-linked glycans are located at residue Asn76 (T5) and comprise a relative abundance of G0F between about 3.2% and about 5.6%.

In some aspects, the one or more N-linked glycans are located at residue Asn108 (T7) and comprise a relative abundance of G0F between about 1.0% and about 6%.

In some aspects, the one or more N-linked glycans are located at residue Asn108 (T7) and comprise a relative abundance of G0F between about 1.0% and about 6%, about 1.0% and about 5.5%, about 1.0% and about 5.0%, about 1.0% and about 4.5%, about 1.0% and about 4.0%, about 1.5% and about 6%, about 1.5% and about 5.5%, about 1.5% and about 5.0%, about 1.5% and about 4.5%, about 1.5% and about 4.0%, about 2.0% and about 6%, about 2.0% and about 5.5%, about 2.0% and about 5.0%, about 2.0% and about 4.5%, or about 2.0% and about 4.0%. In some aspects, the one or more N-linked glycans are located at residue Asn108 (T7) and comprise a relative abundance of G0F between about 2.1% and about 4.0%, between about 1.8% and about 3.5%, or between about 1.8% and 4.0%.

In some aspects, the one or more N-linked glycans are located at residue Asn108 (T7) and comprise a relative abundance of G0F between about 1.0% and about 6%. In some aspects, the one or more N-linked glycans are located at residue Asn108 (T7) and comprise a relative abundance of G0F between about 1.0% and about 5.5%. In some aspects, the one or more N-linked glycans are located at residue Asn108 (T7) and comprise a relative abundance of G0F between about 1.0% and about 5.0%. In some aspects, the one or more N-linked glycans are located at residue Asn108 (T7) and comprise a relative abundance of G0F between about 1.0% and about 4.5%. In some aspects, the one or more N-linked glycans are located at residue Asn108 (T7) and comprise a relative abundance of G0F between about 1.0% and about 4.0%. In some aspects, the one or more N-linked glycans are located at residue Asn108 (T7) and comprise a relative abundance of G0F between about 1.5% and about 6%. In some aspects, the one or more N-linked glycans are located at residue Asn108 (T7) and comprise a relative abundance of G0F between about 1.5% and about 5.5%. In some aspects, the one or more N-linked glycans are located at residue Asn108 (T7) and comprise a relative abundance of G0F between about 1.5% and about 5.0%. In some aspects, the one or more N-linked glycans are located at residue Asn108 (T7) and comprise a relative abundance of G0F between about 1.5% and about 4.5%. In some aspects, the one or more N-linked glycans are located at residue Asn108 (T7) and comprise a relative abundance of G0F between about 1.5% and about 4.0%.

The methods of the present disclosure are useful for controlling or maintaining the G2F content of a protein. The G2F content of a protein is related to the protein's elimination rate from the human body, and therefore the present methods are also directed to controlling the elimination half-life of a protein by controlling its glycan content, including G2F content. In some aspects, the methods of the present disclosure are useful for increasing the circulating half-life of a protein by reducing its elimination rate. In some aspects, the protein is recombinant (e.g., abatacept). In some aspects, the protein's elimination half-life is reduced. In some aspects, the protein's circulating half-life is increased.

In some aspects, the one or more N-linked glycans are located at residue Asn76 (T5) and comprise a relative abundance of G2F between about 5% and about 12%. In some aspects, the one or more N-linked glycans are located at residue Asn76 (T5) and comprise a relative abundance of G2F between about 5% and about 12%, about 5% and about 11.5%, about 5% and about 11%, about 5% and about 10.5%, about 5% and about 10%, about 5.5% and about 12%, about 5.5% and about 11.5%, about 5.5% and about 11%, about 5.5% and about 10.5%, about 5.5% and about 10%, about 6% and about 12%, about 6% and about 11.5%, about 6% and about 11%, about 6% and about 10.5%, about 6% and about 10%, about 6.5% and about 12%, about 6.5% and about 11.5%, about 6.5% and about 11%, about 6.5% and about 10.5%, about 6.5% and about 10%, about 7% and about 12%, about 7% and about 11.5%, about 7% and about 11%, about 7% and about 10.5%, or about 7% and about 10%. In some aspects, the one or more N-linked glycans are located at residue Asn76 (T5) and comprise a relative abundance of G2F between about 7.2% and about 9.8%, between about 6.3% and 10.6%, or about 7.2% and about 10.6%. In some aspects, the one or more N-linked glycans are located at residue Asn108 (T7) and comprise a relative abundance of G2F between about 5% and about 21%. In some aspects, the methods comprise culturing a protein under any one of conditions disclosed herein, e.g., a condition of an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., wherein the protein has N-linked glycans, e.g., G2F, at residue Asn76 (T5) with a relative abundance of G2F between about 5% and about 12%.

In some aspects, the one or more N-linked glycans are located at residue Asn76 (T5) and comprise a relative abundance of G2F between about 5% and about 11.5%. In some aspects, the one or more N-linked glycans are located at residue Asn76 (T5) and comprise a relative abundance of G2F between about 5% and about 11%. In some aspects, the one or more N-linked glycans are located at residue Asn76 (T5) and comprise a relative abundance of G2F between about 5% and about 10.5%. In some aspects, the one or more N-linked glycans are located at residue Asn76 (T5) and comprise a relative abundance of G2F between about 5% and about 10%. In some aspects, the one or more N-linked glycans are located at residue Asn76 (T5) and comprise a relative abundance of G2F between about 5.5% and about 12%. In some aspects, the one or more N-linked glycans are located at residue Asn76 (T5) and comprise a relative abundance of G2F between about 5.5% and about 11.5%. In some aspects, the one or more N-linked glycans are located at residue Asn76 (T5) and comprise a relative abundance of G2F between about 5.5% and about 11%. In some aspects, the one or more N-linked glycans are located at residue Asn76 (T5) and comprise a relative abundance of G2F between about 5.5% and about 10.5%. In some aspects, the one or more N-linked glycans are located at residue Asn76 (T5) and comprise a relative abundance of G2F between about 5.5% and about 10%. In some aspects, the one or more N-linked glycans are located at residue Asn76 (T5) and comprise a relative abundance of G2F between about 7.2% and about 9.8%. In some aspects, the one or more N-linked glycans are located at residue Asn76 (T5) and comprise a relative abundance of G2F between about 6.3% and about 10.6%. In some aspects, the one or more N-linked glycans are located at residue Asn76 (T5) and comprise a relative abundance of G2F between about 5% and about 21%.

In some aspects, the one or more N-linked glycans are located at residue Asn108 (T7) and comprise a relative abundance of G2F between about 5% and about 21%, about 5% and about 20.5%, about 5% and about 20%, about 5% and about 19.5%, about 5% and about 19%, about 5.5% and about 21%, about 5.5% and about 20.5%, about 5.5% and about 20%, about 5.5% and about 19.5%, about 5.5% and about 19%, about 6% and about 21%, about 6% and about 20.5%, about 6% and about 20%, about 6% and about 19.5%, about 6% and about 19%, about 6.5% and about 21%, about 6.5% and about 20.5%, about 6.5% and about 20%, about 6.5% and about 19.5%, about 6.5% and about 19%, about 7% and about 21%, about 7% and about 20.5%, about 7% and about 20%, about 7% and about 19.5%, about 7% and about 19%, about 7.5% and about 21%, about 7.5% and about 20.5%, about 7.5% and about 20%, about 7.5% and about 19.5%, about 7.5% and about 19%, about 8% and about 21%, about 8% and about 20.5%, about 8% and about 20%, about 8% and about 19.5%, or about 8% and about 19%.

In some aspects, the one or more N-linked glycans are located at residue Asn108 (T7) and comprise a relative abundance of G2F between about 8.2% and about 14.1%, about 8.0% and about 18.6%, or about 8.2% and about 14.1%. In some aspects, G2F further comprises a galactose-alpha-1,3-galactose moiety (G2F-Gal), wherein the G2F-Gal comprise a relative abundance of less than or equal to about 1.4%. In some aspects, the G2F-Gal comprises a relative abundance of between about 1.0% to about 1.4%. In some aspects, the G2F-Gal comprises a relative abundance of between about 0.4% to about 0.9%.

In some aspects, the glycosylation profile does not include more than one galactose-alpha-1,3-galactose (alpha-gal) linkage.

In some aspects, the one or more N-linked glycans are located at residue Asn108 (T7) and comprise a relative abundance of G2F between about 5% and about 21%. In some aspects, the one or more N-linked glycans are located at residue Asn108 (T7) and comprise a relative abundance of G2F between about 5% and about 20.5%. In some aspects, the one or more N-linked glycans are located at residue Asn108 (T7) and comprise a relative abundance of G2F between about 5% and about 20%. In some aspects, the one or more N-linked glycans are located at residue Asn108 (T7) and comprise a relative abundance of G2F between about 5.5% and about 21%. In some aspects, the one or more N-linked glycans are located at residue Asn108 (T7) and comprise a relative abundance of G2F between about 5.5% and about 21%. In some aspects, the one or more N-linked glycans are located at residue Asn108 (T7) and comprise a relative abundance of G2F between about 5.5% and about 20.5%. In some aspects, the one or more N-linked glycans are located at residue Asn108 (T7) and comprise a relative abundance of G2F between about 8.2% and about 14.1%. In some aspects, the one or more N-linked glycans are located at residue Asn108 (T7) and comprise a relative abundance of G2F between about 8.0% and about 18.6%. In some aspects, the one or more N-linked glycans are located at residue Asn108 (T7) and comprise a relative abundance of G2F between about 8.2% and about 14.1%.

In some aspects, the methods comprise culturing a protein under any one of conditions disclosed herein, e.g., a condition of an initial temperature set point between about 35° C. and about 37° C., e.g., about 36° C., a second temperature set point between 32° C. and about 34° C., e.g., about 33° C., and a third temperature set point between about 30° C. and about 32° C., e.g., about 31° C., wherein the protein has N-linked glycans, e.g., G2F, at residue Asn108 (T7) with a relative abundance of G2F between about 5% and about 21%.

In some aspects, the one or more N-linked glycans are located at residue Asn76 (T5) and comprise a relative abundance of S1G2F between about 29% and about 38%. In some aspects, the one or more N-linked glycans are located at residue Asn76 (T5) and comprise a relative abundance of S1G2F between about 29% and about 38%, about 29% and about 37.5%, about 29% and about 37%, about 29% and about 36.5%, about 29.5% and about 38%, about 29.5% and about 37.5%, about 29.5% and about 37%, about 29.5% and about 36.5%, about 30% and about 38%, about 30% and about 37.5%, about 30% and about 37%, about 30% and about 36.5%, about 31.5% and about 38%, about 31.5% and about 37.5%, about 31.5% and about 37%, about 31.5% and about 36.5%.

In some aspects, the one or more N-linked glycans are located at residue Asn76 (T5) and comprise a relative abundance of S1G2F between about 29.5% and about 38%. In some aspects, the one or more N-linked glycans are located at residue Asn76 (T5) and comprise a relative abundance of S1G2F between about 29.5% and about 37.5%. In some aspects, the one or more N-linked glycans are located at residue Asn76 (T5) and comprise a relative abundance of S1G2F between about 29.5% and about 37%. In some aspects, the one or more N-linked glycans are located at residue Asn76 (T5) and comprise a relative abundance of S1G2F between about 29.5% and about 36.5%. In some aspects, the one or more N-linked glycans are located at residue Asn76 (T5) and comprise a relative abundance of S1G2F between about 29% and about 38%. In some aspects, the one or more N-linked glycans are located at residue Asn76 (T5) and comprise a relative abundance of S1G2F between about 29.5% and about 37.5%. In some aspects, the one or more N-linked glycans are located at residue Asn76 (T5) and comprise a relative abundance of S1G2F between about 29.5% and about 37%. In some aspects, the one or more N-linked glycans are located at residue Asn76 (T5) and comprise a relative abundance of S1G2F between about 29.5% and about 36.5%. In some aspects, the one or more N-linked glycans are located at residue Asn76 (T5) and comprise a relative abundance of S1G2F between about 30% and about 38%. In some aspects, the one or more N-linked glycans are located at residue Asn76 (T5) and comprise a relative abundance of S1G2F between about 30% and about 37.5%. In some aspects, the one or more N-linked glycans are located at residue Asn76 (T5) and comprise a relative abundance of S1G2F between about 30% and about 37%. In some aspects, the one or more N-linked glycans are located at residue Asn76 (T5) and comprise a relative abundance of S1G2F between about 30% and about 36.5%. In some aspects, the one or more N-linked glycans are located at residue Asn76 (T5) and comprise a relative abundance of S1G2F between about 31.6% and about 35.1%, about 31.3% and about 36.5%, or about 31.3% and about 36.5%. In some aspects, the one or more N-linked glycans are located at residue Asn76 (T5) and comprise a relative abundance of S1G2F between about 31.6% and about 35.1%. In some aspects, the one or more N-linked glycans are located at residue Asn76 (T5) and comprise a relative abundance of S1G2F between about 31.3% and about 36.5%. In some aspects, the one or more N-linked glycans are located at residue Asn76 (T5) and comprise a relative abundance of S1G2F between about 31.3% and about 36.5%.

In some aspects, the one or more N-linked glycans are located at residue Asn108 (T7) and comprise a relative abundance of S1G2F between 33% and about 45%. In some aspects, the one or more N-linked glycans are located at residue Asn108 (T7) and comprise a relative abundance of S1G2F between about 33% and about 45%, about 33% and about 44.5%, about 33% and about 44%, about 33% and about 43.5%, about 33% and about 43%, about 33% and about 42.5%, about 33.5% and about 45%, about 33.5% and about 44.5%, about 33.5% and about 44%, about 33.5% and about 43.5%, about 33.5% and about 43%, about 33.5% and about 42.5%, about 34% and about 45%, about 34% and about 44.5%, about 34% and about 44%, about 34% and about 43.5%, about 34% and about 43%, about 34% and about 42.5%, about 34.5% and about 45%, about 34.5% and about 44.5%, about 34.5% and about 44%, about 34.5% and about 43.5%, about 34.5% and about 43%, or about 34.5% and about 42.5%.

In some aspects, the one or more N-linked glycans are located at residue Asn108 (T7) and comprise a relative abundance of S1G2F between about 33% and about 45%. In some aspects, the one or more N-linked glycans are located at residue Asn108 (T7) and comprise a relative abundance of S1G2F between about 33% and about 44.5%. In some aspects, the one or more N-linked glycans are located at residue Asn108 (T7) and comprise a relative abundance of S1G2F between about 33% and about 44%. In some aspects, the one or more N-linked glycans are located at residue Asn108 (T7) and comprise a relative abundance of S1G2F between about 33% and about 43.5%. In some aspects, the one or more N-linked glycans are located at residue Asn108 (T7) and comprise a relative abundance of S1G2F between about 33% and about 43%. In some aspects, the one or more N-linked glycans are located at residue Asn108 (T7) and comprise a relative abundance of S1G2F between about 33% and about 43.5%. In some aspects, the one or more N-linked glycans are located at residue Asn108 (T7) and comprise a relative abundance of S1G2F between about 33% and about 43%. In some aspects, the one or more N-linked glycans are located at residue Asn108 (T7) and comprise a relative abundance of S1G2F between about 33% and about 42.5%.

In some aspects, the one or more N-linked glycans are located at residue Asn108 (T7) and comprise a relative abundance of S1G2F between about 33% and about 45%. In some aspects, the one or more N-linked glycans are located at residue Asn108 (T7) and comprise a relative abundance of S1G2F between about 33.5% and about 44.5%. In some aspects, the one or more N-linked glycans are located at residue Asn108 (T7) and comprise a relative abundance of S1G2F between about 33.5% and about 44%. In some aspects, the one or more N-linked glycans are located at residue Asn108 (T7) and comprise a relative abundance of S1G2F between about 33.5% and about 43.5%. In some aspects, the one or more N-linked glycans are located at residue Asn108 (T7) and comprise a relative abundance of S1G2F between about 33.5% and about 43%. In some aspects, the one or more N-linked glycans are located at residue Asn108 (T7) and comprise a relative abundance of S1G2F between about 33.5% and about 43.5%. In some aspects, the one or more N-linked glycans are located at residue Asn108 (T7) and comprise a relative abundance of S1G2F between about 33.5% and about 43%. In some aspects, the one or more N-linked glycans are located at residue Asn108 (T7) and comprise a relative abundance of S1G2F between about 33.5% and about 42.5%.

In some aspects, the one or more N-linked glycans are located at residue Asn108 (T7) and comprise a relative abundance of S1G2F between about 34% and about 45%. In some aspects, the one or more N-linked glycans are located at residue Asn108 (T7) and comprise a relative abundance of S1G2F between about 34% and about 44.5%. In some aspects, the one or more N-linked glycans are located at residue Asn108 (T7) and comprise a relative abundance of S1G2F between about 34% and about 44%. In some aspects, the one or more N-linked glycans are located at residue Asn108 (T7) and comprise a relative abundance of S1G2F between about 34% and about 43.5%. In some aspects, the one or more N-linked glycans are located at residue Asn108 (T7) and comprise a relative abundance of S1G2F between about 34% and about 43%. In some aspects, the one or more N-linked glycans are located at residue Asn108 (T7) and comprise a relative abundance of S1G2F between about 34% and about 43.5%. In some aspects, the one or more N-linked glycans are located at residue Asn108 (T7) and comprise a relative abundance of S1G2F between about 34% and about 43%. In some aspects, the one or more N-linked glycans are located at residue Asn108 (T7) and comprise a relative abundance of S1G2F between about 34% and about 42.5%. In some aspects, the one or more N-linked glycans are located at residue Asn108 (T7) and comprise a relative abundance of S1G2F between about 34.2% and about 37.7%, about 35.5% and about 42.3%, or about 34.2% and about 42.3%. In some aspects, the one or more N-linked glycans are located at residue Asn108 (T7) and comprise a relative abundance of S1G2F between about 34.2% and about 42.3%. In some aspects, the one or more N-linked glycans are located at residue Asn108 (T7) and comprise a relative abundance of S1G2F between about 35.2% and about 42.3%. In some aspects, the one or more N-linked glycans are located at residue Asn108 (T7) and comprise a relative abundance of S1G2F between about 34.2% and about 37.7%. In some aspects, S1G2F further comprises a galactose-alpha-1,3-galactose moiety (S1G2F-Gal), wherein the S1G2F-Gal comprise a relative abundance of less than or equal to about 4.7%. In some aspects, the S1G2F-Gal comprises a relative abundance of between about 2.3% to about 4.7%. In some aspects, S1G2F-Gal comprises a relative abundance of between about 1.4% to about 1.8%.

In some aspects, the one or more N-linked glycans are located at residue Asn76 (T5) and comprise a relative abundance of S2G2F between about 13% and about 25%. In some aspects, the one or more N-linked glycans are located at residue Asn76 (T5) and comprise a relative abundance of S2G2F between about 13% and about 25%, between about 13% and about 24.5%, between about 13% and about 24%, between about 13% and about 23.5%, between about 13% and about 23%, between about 13.5% and about 25%, between about 13.5% and about 24.5%, between about 13.5% and about 24%, between about 13.5% and about 23.5%, between about 13.5% and about 23%, between about 14% and about 25%, between about 14% and about 24.5%, between about 14% and about 24%, between about 14% and about 23.5%, between about 14% and about 23%, between about 14.5% and about 25%, between about 14.5% and about 24.5%, between about 14.5% and about 24%, between about 14.5% and about 23.5%, between about 14.5% and about 23%, between about 15% and about 25%, between about 15% and about 24.5%, between about 15% and about 24%, between about 15% and about 23.5%, between about 15% and about 23%, between about 15.5% and about 25%, between about 15.5% and about 24.5%, between about 15.5% and about 24%, between about 15.5% and about 23.5%, or about 15.5% and about 23%.

In some aspects, the one or more N-linked glycans are located at residue Asn76 (T5) and comprise a relative abundance of S2G2F between about 13% and about 25%. In some aspects, the one or more N-linked glycans are located at residue Asn76 (T5) and comprise a relative abundance of S2G2F between about 13% and about 24.5%. In some aspects, the one or more N-linked glycans are located at residue Asn76 (T5) and comprise a relative abundance of S2G2F between about 13% and about 24%. In some aspects, the one or more N-linked glycans are located at residue Asn76 (T5) and comprise a relative abundance of S2G2F between about 13% and about 23.5%. In some aspects, the one or more N-linked glycans are located at residue Asn76 (T5) and comprise a relative abundance of S2G2F between about 13% and about 23.5%.

In some aspects, the one or more N-linked glycans are located at residue Asn76 (T5) and comprise a relative abundance of S2G2F between about 13.5% and about 25%. In some aspects, the one or more N-linked glycans are located at residue Asn76 (T5) and comprise a relative abundance of S2G2F between about 13.5% and about 24.5%. In some aspects, the one or more N-linked glycans are located at residue Asn76 (T5) and comprise a relative abundance of S2G2F between about 13.5% and about 24%. In some aspects, the one or more N-linked glycans are located at residue Asn76 (T5) and comprise a relative abundance of S2G2F between about 13.5% and about 23.5%. In some aspects, the one or more N-linked glycans are located at residue Asn76 (T5) and comprise a relative abundance of S2G2F between about 13.5% and about 23.5%. In some aspects, the one or more N-linked glycans are located at residue Asn76 (T5) and comprise a relative abundance of S2G2F between about 14% and about 25%. In some aspects, the one or more N-linked glycans are located at residue Asn76 (T5) and comprise a relative abundance of S2G2F between about 14% and about 24.5%. In some aspects, the one or more N-linked glycans are located at residue Asn76 (T5) and comprise a relative abundance of S2G2F between about 14% and about 24%. In some aspects, the one or more N-linked glycans are located at residue Asn76 (T5) and comprise a relative abundance of S2G2F between about 14% and about 23.5%. In some aspects, the one or more N-linked glycans are located at residue Asn76 (T5) and comprise a relative abundance of S2G2F between about 14% and about 23.5%. In some aspects, the one or more N-linked glycans are located at residue Asn76 (T5) and comprise a relative abundance of S2G2F between about 15% and about 25%. In some aspects, the one or more N-linked glycans are located at residue Asn76 (T5) and comprise a relative abundance of S2G2F between about 15% and about 24.5%. In some aspects, the one or more N-linked glycans are located at residue Asn76 (T5) and comprise a relative abundance of S2G2F between about 15% and about 24%. In some aspects, the one or more N-linked glycans are located at residue Asn76 (T5) and comprise a relative abundance of S2G2F between about 15% and about 23.5%. In some aspects, the one or more N-linked glycans are located at residue Asn76 (T5) and comprise a relative abundance of S2G2F between about 15% and about 23.5%.

In some aspects, the one or more N-linked glycans are located at residue Asn76 (T5) and comprise a relative abundance of S2G2F between about 18.1% and about 22.9%, about 15.4% and about 20%, and about 15.4% and about 22.9%. In some aspects, the one or more N-linked glycans are located at residue Asn76 (T5) and comprise a relative abundance of S2G2F between about 18% and about 24%, between about 18% and about 23%, or between about 19% and about 23%. In some aspects, the one or more N-linked glycans are located at residue Asn76 (T5) and comprise a relative abundance of S2G2F between about 18.1% and about 22.9%. In some aspects, the one or more N-linked glycans are located at residue Asn76 (T5) and comprise a relative abundance of S2G2F between about 15.4% and about 20%. In some aspects, the one or more N-linked glycans are located at residue Asn76 (T5) and comprise a relative abundance of S2G2F between about 15.4% and about 22.9%. In some aspects, the one or more N-linked glycans are located at residue Asn76 (T5) and comprise a relative abundance of S2G2F between about 18% and about 24%. In some aspects, the one or more N-linked glycans are located at residue Asn76 (T5) and comprise a relative abundance of S2G2F between about 18% and about 23%. In some aspects, the one or more N-linked glycans are located at residue Asn76 (T5) and comprise a relative abundance of S2G2F between about 19% and about 23%.

In some aspects, the one or more N-linked glycans are located at residue Asn108 (T7) and comprise a relative abundance of S2G2F between about 18% and about 36%. In some aspects, the one or more N-linked glycans are located at residue Asn108 (T7) and comprise a relative abundance of S2G2F between about 18% and about 36%, about 18% and about 35.5%, about 18% and about 35%, about 18% and about 34.5%, about 18% and about 34%, about 18% and about 33.5%, about 18.5% and about 36%, about 18.5% and about 35.5%, about 18.5% and about 35%, about 18.5% and about 34.5%, about 18.5% and about 34%, about 18.5% and about 33.5%, about 19% and about 36%, about 19% and about 35.5%, about 19% and about 35%, about 19% and about 34.5%, about 19% and about 34%, about 19% and about 33.5%, about 19.5% and about 36%, about 19.5% and about 35.5%, about 19.5% and about 35%, about 19.5% and about 34.5%, about 19.5% and about 34%, about 19.5% and about 33.5%, about 20% and about 36%, about 20% and about 35.5%, about 20% and about 35%, about 20% and about 34.5%, about 20% and about 34%, about 20% and about 33.5%, about 20.5% and about 36%, about 20.5% and about 35.5%, about 20.5% and about 35%, about 20.5% and about 34.5%, about 20.5% and about 34%, or about 20.5% and about 33.5%. In some aspects, the one or more N-linked glycans are located at residue Asn108 (T7) and comprise a relative abundance of S2G2F between about 18% and about 36%. In some aspects, the one or more N-linked glycans are located at residue Asn108 (T7) and comprise a relative abundance of S2G2F between about 18% and about 35.5%. In some aspects, the one or more N-linked glycans are located at residue Asn108 (T7) and comprise a relative abundance of S2G2F between about 18% and about 35%. In some aspects, the one or more N-linked glycans are located at residue Asn108 (T7) and comprise a relative abundance of S2G2F between about 18% and about 34.5%.

In some aspects, the one or more N-linked glycans are located at residue Asn108 (T7) and comprise a relative abundance of S2G2F between about 18% and about 34%. In some aspects, the one or more N-linked glycans are located at residue Asn108 (T7) and comprise a relative abundance of S2G2F between about 18% and about 33.5%. In some aspects, the one or more N-linked glycans are located at residue Asn108 (T7) and comprise a relative abundance of S2G2F between about 18.5% and about 36%. In some aspects, the one or more N-linked glycans are located at residue Asn108 (T7) and comprise a relative abundance of S2G2F between about 18.5% and about 35.5%. In some aspects, the one or more N-linked glycans are located at residue Asn108 (T7) and comprise a relative abundance of S2G2F between about 18.5% and about 35%. In some aspects, the one or more N-linked glycans are located at residue Asn108 (T7) and comprise a relative abundance of S2G2F between about 18.5% and about 34.5%. In some aspects, the one or more N-linked glycans are located at residue Asn108 (T7) and comprise a relative abundance of S2G2F between about 18.5% and about 34%. In some aspects, the one or more N-linked glycans are located at residue Asn108 (T7) and comprise a relative abundance of S2G2F between about 18.5% and about 33.5%. In some aspects, the one or more N-linked glycans are located at residue Asn108 (T7) and comprise a relative abundance of S2G2F between about 19% and about 36%.

In some aspects, the one or more N-linked glycans are located at residue Asn108 (T7) and comprise a relative abundance of S2G2F between about 19% and about 35.5%. In some aspects, the one or more N-linked glycans are located at residue Asn108 (T7) and comprise a relative abundance of S2G2F between about 19% and about 35%. In some aspects, the one or more N-linked glycans are located at residue Asn108 (T7) and comprise a relative abundance of S2G2F between about 19% and about 34.5%. In some aspects, the one or more N-linked glycans are located at residue Asn108 (T7) and comprise a relative abundance of S2G2F between about 19% and about 34%. In some aspects, the one or more N-linked glycans are located at residue Asn108 (T7) and comprise a relative abundance of S2G2F between about 19% and about 33.5%. In some aspects, the one or more N-linked glycans are located at residue Asn108 (T7) and comprise a relative abundance of S2G2F between about 19.5% and about 36%. In some aspects, the one or more N-linked glycans are located at residue Asn108 (T7) and comprise a relative abundance of S2G2F between about 19.5% and about 35.5%. In some aspects, the one or more N-linked glycans are located at residue Asn108 (T7) and comprise a relative abundance of S2G2F between about 19.5% and about 35%. In some aspects, the one or more N-linked glycans are located at residue Asn108 (T7) and comprise a relative abundance of S2G2F between about 19.5% and about 34.5%.

In some aspects, the one or more N-linked glycans are located at residue Asn108 (T7) and comprise a relative abundance of S2G2F between about 19.5% and about 34%. In some aspects, the one or more N-linked glycans are located at residue Asn108 (T7) and comprise a relative abundance of S2G2F between about 19.5% and about 33.5%. In some aspects, the one or more N-linked glycans are located at residue Asn108 (T7) and comprise a relative abundance of S2G2F between about 20% and about 36%. In some aspects, the one or more N-linked glycans are located at residue Asn108 (T7) and comprise a relative abundance of S2G2F between about 20% and about 35.5%. In some aspects, the one or more N-linked glycans are located at residue Asn108 (T7) and comprise a relative abundance of S2G2F between about 20% and about 35%.

In some aspects, the one or more N-linked glycans are located at residue Asn108 (T7) and comprise a relative abundance of S2G2F between about 20% and about 34.5%. In some aspects, the one or more N-linked glycans are located at residue Asn108 (T7) and comprise a relative abundance of S2G2F between about 20% and about 34%. In some aspects, the one or more N-linked glycans are located at residue Asn108 (T7) and comprise a relative abundance of S2G2F between about 20% and about 33.5%. In some aspects, the one or more N-linked glycans are located at residue Asn108 (T7) and comprise a relative abundance of S2G2F between about 23.2% and about 33.8%. In some aspects, the one or more N-linked glycans are located at residue Asn108 (T7) and comprise a relative abundance of S2G2F between about 20.8% and about 32.6%. In some aspects, the one or more N-linked glycans are located at residue Asn108 (T7) and comprise a relative abundance of S2G2F between about 20.8% and about 33.8%. In some aspects, the one or more N-linked glycans are located at residue Asn108 (T7) and comprise a relative abundance of S2G2F between about 23.2% and about 33.8%, about 20.8% and about 32.6%, or about 20.8% and 33.8%.

In some aspects, the one or more N-linked glycans are located at residue Asn76 (T5) and comprise a relative abundance of S1G3F between about 2% and about 8%. In some aspects, the one or more N-linked glycan are located at residue Asn76 (T5) and comprise a relative abundance of S1G3F between about 2% and about 8%, about 2% and about 7.5%, about 2% and about 7%, about 2% and about 6.5%, about 2% and about 6%, about 2% and about 5.5%, about 2.5% and about 8%, about 2.5% and about 7.5%, about 2.5% and about 7%, about 2.5% and about 6.5%, about 2.5% and about 6%, about 2.5% and about 5.5%, about 3% and about 8%, about 3% and about 7.5%, about 3% and about 7%, about 3% and about 6.5%, about 3% and about 6%, about 3% and about 5.5%, about 3.5% and about 8%, about 3.5% and about 7.5%, about 3.5% and about 7%, about 3.5% and about 6.5%, about 3.5% and about 6%, about 3.5% and about 5.5%, about 4% and about 8%, about 4% and about 7.5%, about 4% and about 7%, about 4% and about 6.5%, about 4% and about 6%, or about 4% and about 5.5%.

In some aspects, the one or more N-linked glycans are located at residue Asn76 (T5) and comprise a relative abundance of S1G3F between about 2% and about 8%. In some aspects, the one or more N-linked glycans are located at residue Asn76 (T5) and comprise a relative abundance of S1G3F between about 2% and about 7.5%. In some aspects, the one or more N-linked glycans are located at residue Asn76 (T5) and comprise a relative abundance of S1G3F between about 2% and about 7%. In some aspects, the one or more N-linked glycans are located at residue Asn76 (T5) and comprise a relative abundance of S1G3F between about 2% and about 6.5%. In some aspects, the one or more N-linked glycans are located at residue Asn76 (T5) and comprise a relative abundance of S1G3F between about 2% and about 6%. In some aspects, the one or more N-linked glycans are located at residue Asn76 (T5) and comprise a relative abundance of S1G3F between about 2% and about 5.5%. In some aspects, the one or more N-linked glycans are located at residue Asn76 (T5) and comprise a relative abundance of S1G3F between about 2.5% and about 8%. In some aspects, the one or more N-linked glycans are located at residue Asn76 (T5) and comprise a relative abundance of S1G3F between about 2.5% and about 7.5%. In some aspects, the one or more N-linked glycans are located at residue Asn76 (T5) and comprise a relative abundance of S1G3F between about 2.5% and about 7%. In some aspects, the one or more N-linked glycans are located at residue Asn76 (T5) and comprise a relative abundance of S1G3F between about 2.5% and about 6.5%. In some aspects, the one or more N-linked glycans are located at residue Asn76 (T5) and comprise a relative abundance of S1G3F between about 2.5% and about 6%.

In some aspects, the one or more N-linked glycans are located at residue Asn76 (T5) and comprise a relative abundance of S1G3F between about 2.5% and about 5.5%. In some aspects, the one or more N-linked glycans are located at residue Asn76 (T5) and comprise a relative abundance of S1G3F between about 3% and about 8%. In some aspects, the one or more N-linked glycans are located at residue Asn76 (T5) and comprise a relative abundance of S1G3F between about 3% and about 7.5%. In some aspects, the one or more N-linked glycans are located at residue Asn76 (T5) and comprise a relative abundance of S1G3F between about 3% and about 7%. In some aspects, the one or more N-linked glycans are located at residue Asn76 (T5) and comprise a relative abundance of S1G3F between about 3% and about 6.5%. In some aspects, the one or more N-linked glycans are located at residue Asn76 (T5) and comprise a relative abundance of S1G3F between about 3% and about 6%.

In some aspects, the one or more N-linked glycans are located at residue Asn76 (T5) and comprise a relative abundance of S1G3F between about 3% and about 5.5%. In some aspects, the one or more N-linked glycans are located at residue Asn76 (T5) and comprise a relative abundance of S1G3F between about 3.5% and about 8%. In some aspects, the one or more N-linked glycans are located at residue Asn76 (T5) and comprise a relative abundance of S1G3F between about 3.5% and about 7.5%. In some aspects, the one or more N-linked glycans are located at residue Asn76 (T5) and comprise a relative abundance of S1G3F between about 3.5% and about 7%. In some aspects, the one or more N-linked glycans are located at residue Asn76 (T5) and comprise a relative abundance of S1G3F between about 3.5% and about 6.5%. In some aspects, the one or more N-linked glycans are located at residue Asn76 (T5) and comprise a relative abundance of S1G3F between about 3.5% and about 6%. In some aspects, the one or more N-linked glycans are located at residue Asn76 (T5) and comprise a relative abundance of S1G3F between about 3.5% and about 5.5%. In some aspects, the one or more N-linked glycans are located at residue Asn76 (T5) and comprise a relative abundance of S1G3F between about 4% and about 8%. In some aspects, the one or more N-linked glycans are located at residue Asn76 (T5) and comprise a relative abundance of S1G3F between about 4% and about 7.5%. In some aspects, the one or more N-linked glycans are located at residue Asn76 (T5) and comprise a relative abundance of S1G3F between about 4% and about 7%. In some aspects, the one or more N-linked glycans are located at residue Asn76 (T5) and comprise a relative abundance of S1G3F between about 4% and about 6.5%. In some aspects, the one or more N-linked glycans are located at residue Asn76 (T5) and comprise a relative abundance of S1G3F between about 4% and about 6%. In some aspects, the one or more N-linked glycans are located at residue Asn76 (T5) and comprise a relative abundance of S1G3F between about 4% and about 5.5%. In some aspects, the one or more N-linked glycans are located at residue Asn76 (T5) and comprise a relative abundance of S1G3F between about 4.4% and about 5.6%. In some aspects, the one or more N-linked glycans are located at residue Asn76 (T5) and comprise a relative abundance of S1G3F between about 4% and about 5.6%. In some aspects, the one or more N-linked glycans are located at residue Asn76 (T5) and comprise a relative abundance of S1G3F between about 4.4% and about 5.6% or about 4.0% and about 5.5%.

In some aspects, the one or more N-linked glycans are located at residue Asn108 (T7) and comprise a relative abundance of S1G3F between about 0.5% and about 4%. In some aspects, the one or more N-linked glycans are located at residue Asn108 (T7) and comprise a relative abundance of S1G3F between about 0.5% and about 4%, about 0.5% and about 3.5%, about 0.5% and about 3%, about 0.5% and about 2.5%, about 1% and about 4%, about 1% and about 3.5%, about 1% and about 3%, or about 1% and about 2.5%.

In some aspects, the one or more N-linked glycans are located at residue Asn108 (T7) and comprise a relative abundance of S1G3F between about 1.4% and about 2.2%, about 1.1% and about 1.9%, or about 1.1% and about 2.2%. In some aspects, the one or more N-linked glycans are located at residue Asn108 (T7) and comprise a relative abundance of S1G3F between about 1% and about 3%, about 1% and about 2%, or about 1% and about 1.5%.

In some aspects, the one or more N-linked glycans are located at residue Asn76 (T5) and comprise a relative abundance of S1G3F between about 0.5% and about 4%. In some aspects, the one or more N-linked glycans are located at residue Asn76 (T5) and comprise a relative abundance of S1G3F between about 0.5% and about 3.5%. In some aspects, the one or more N-linked glycans are located at residue Asn76 (T5) and comprise a relative abundance of S1G3F between about 0.5% and about 3%. In some aspects, the one or more N-linked glycans are located at residue Asn76 (T5) and comprise a relative abundance of S1G3F between about 0.5% and about 2.5%. In some aspects, the one or more N-linked glycans are located at residue Asn76 (T5) and comprise a relative abundance of S1G3F between about 1% and about 4%. In some aspects, the one or more N-linked glycans are located at residue Asn76 (T5) and comprise a relative abundance of S1G3F between about 1% and about 3.5%. In some aspects, the one or more N-linked glycans are located at residue Asn76 (T5) and comprise a relative abundance of S1G3F between about 1% and about 3%. In some aspects, the one or more N-linked glycans are located at residue Asn76 (T5) and comprise a relative abundance of S1G3F between about 1% and about 2.5%. In some aspects, the one or more N-linked glycans are located at residue Asn76 (T5) and comprise a relative abundance of S1G3F between about 1.1% and about 1.9%. In some aspects, the one or more N-linked glycans are located at residue Asn76 (T5) and comprise a relative abundance of S1G3F between about 1.1% and about 2.2%. In some aspects, the one or more N-linked glycans are located at residue Asn76 (T5) and comprise a relative abundance of S1G3F between about 1.4% and about 2.2%. In some aspects, the one or more N-linked glycans are located at residue Asn76 (T5) and comprise a relative abundance of S1G3F between about 1% and about 3%. In some aspects, the one or more N-linked glycans are located at residue Asn76 (T5) and comprise a relative abundance of S1G3F between about 1% and about 2%. In some aspects, the one or more N-linked glycans are located at residue Asn76 (T5) and comprise a relative abundance of S1G3F between about 1% and about 1.5%.

In some aspects, the one or more N-linked glycans are located at residue Asn76 (T5) and comprise a relative abundance of S2G4F between about 0.5% and about 4%. In some aspects, the one or more N-linked glycans are located at residue Asn76 (T5) and comprise a relative abundance of S2G4F between about 0.5% and about 4%, about 0.5% and about 3.5%, about 0.5% and about 3%, about 0.5% and about 2.5%, about 1% and about 4%, about 1% and about 3.5%, about 1% and about 3%, or about 1% and about 2.5%. In some aspects, the one or more N-linked glycans are located at residue Asn76 (T5) and comprise a relative abundance of S2G4F between about 1.9% and about 2.4%, about 1.4% and about 2.1%, or about 1.4% and about 2.4%. In some aspects, the one or more N-linked glycans are located at residue Asn76 (T5) and comprise a relative abundance of S2G4F between about 1% and about 2%, about 1% and about 2%, or about 1.5% and about 2.5%.

In some aspects, the one or more N-linked glycans are located at residue Asn76 (T5) and comprise a relative abundance of S2G4F between about 0.5% and about 4%. In some aspects, the one or more N-linked glycans are located at residue Asn76 (T5) and comprise a relative abundance of S2G4F between about 0.5% and about 3.4%. In some aspects, the one or more N-linked glycans are located at residue Asn76 (T5) and comprise a relative abundance of S2G4F between about 0.5% and about 3%. In some aspects, the one or more N-linked glycans are located at residue Asn76 (T5) and comprise a relative abundance of S2G4F between about 0.5% and about 2.5%. In some aspects, the one or more N-linked glycans are located at residue Asn76 (T5) and comprise a relative abundance of S2G4F between about 1% and about 4%. In some aspects, the one or more N-linked glycans are located at residue Asn76 (T5) and comprise a relative abundance of S2G4F between about 1% and about 3.5%. In some aspects, the one or more N-linked glycans are located at residue Asn76 (T5) and comprise a relative abundance of S2G4F between about 1% and about 3%. In some aspects, the one or more N-linked glycans are located at residue Asn76 (T5) and comprise a relative abundance of S2G4F between about 1% and about 2.5%. In some aspects, the one or more N-linked glycans are located at residue Asn76 (T5) and comprise a relative abundance of S2G4F between about 1.9% and about 2.4%. In some aspects, the one or more N-linked glycans are located at residue Asn76 (T5) and comprise a relative abundance of S2G4F between about 1.4% and about 2.1%. In some aspects, the one or more N-linked glycans are located at residue Asn76 (T5) and comprise a relative abundance of S2G4F between about 1.4% and about 2.4%. In some aspects, the one or more N-linked glycans are located at residue Asn76 (T5) and comprise a relative abundance of S2G4F between about 1% and about 2%. In some aspects, the one or more N-linked glycans are located at residue Asn76 (T5) and comprise a relative abundance of S2G4F between about 1.5% and about 2.5%.

In some aspects, the one or more N-linked glycans are located at residue Asn76 (T5) alone, Asn108 (T7) alone, Asn207 (T14) alone, or any combination thereof, and comprise a relative abundance of G0F of less than or equal to about 7.0% or about 6.5%. In some aspects, the one or more N-linked glycans are located at residue Asn76 (T5) alone, Asn108 (T7) alone, Asn207 (T14) alone, or any combination thereof, and comprise a relative abundance of G0F of less than or equal to about 6.0%, less than or equal to about 5.5%, less than or equal to about 5.0%, less than or equal to about 4.5%, less than or equal to about 4.0%, less than or equal to about 3.5%, less than or equal to about 3.0%, less than or equal to about 2.5%, less than or equal to about 2.0%, less than or equal to about 1.5%, less than or equal to about 1.0%, less than or equal to about 0.5%, or about 0.0%.

In some aspects, the one or more N-linked glycans are located at residue Asn76 (T5) alone, Asn108 (T7) alone, Asn207 (T14) alone, or any combination thereof, and comprise a relative abundance of G1F of less than or equal to about 7.5% or 7.0%. In some aspects, the one or more N-linked glycans are located at residue Asn76 (T5) alone, Asn108 (T7) alone, Asn207 (T14) alone, or any combination thereof, and comprise a relative abundance of G1F of less than or equal to about 6.5%, less than or equal to about 6.0%, less than or equal to about 5.5%, less than or equal to about 5.0%, less than or equal to about 4.5%, less than or equal to about 4.0%, less than or equal to about 3.5%, less than or equal to about 3.0%, less than or equal to about 2.5%, less than or equal to about 2.0%, less than or equal to about 1.5%, less than or equal to about 1.0%, less than or equal to about 0.5%, or about 0.0%.

In some aspects, the one or more N-linked glycans are located at residue Asn76 (T5) alone, Asn108 (T7) alone, Asn207 (T14) alone, or any combination thereof, and comprise a relative abundance of G2F of less than or equal to about 25% or of about 1.5% to about 23%. In some aspects, the one or more N-linked glycans are located at residue Asn76 (T5) alone, Asn108 (T7) alone, Asn207 (T14) alone, or any combination thereof, and comprise a relative abundance of G2F of less than or equal to you about 24%, less than or equal to about 23%, less than or equal to about 22%, less than or equal to about 21%, less than or equal to about 20%, less than or equal to about 19%, less than or equal to about 18%, less than or equal to about 17%, less than or equal to about 16%, less than or equal to about 15%, less than or equal to about 14%, less than or equal to about 13%, less than or equal to about 12%, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2%, or less than or equal to about 1%. In some aspects, the one or more N-linked glycans are located at residue Asn76 (T5) alone, Asn108 (T7) alone, Asn207 (T14) alone, or any combination thereof, and comprise a relative abundance of G2F of about 2.0% to about 23%, of about 3% to about 23%, of about 4% to about 23%, of about 5% to about 23%, of about 6% to about 23%, of about 7% to about 23%, of about 8% to about 23%, of about 9% to about 23%, of about 10% to about 23%, of about 11% to about 23%, of about 12% to about 23%, of about 13% to about 23%, of about 14% to about 23%, of about 15% to about 23%, of about 16% to about 23%, of about 17% to about 23%, of about 18% to about 23%, of about 19% to about 23%, of about 20% to about 23%, of about 21% to about 23%, or of about 22% to about 23%.

In some aspects, the one or more N-linked glycans are located at residue Asn76 (T5) alone, Asn108 (T7) alone, Asn207 (T14) alone, or any combination thereof, and comprise a relative abundance of S1G1F of less than or equal to 13.5% or of about 12.5%. In some aspects, the one or more N-linked glycans are located at residue Asn76 (T5) alone, Asn108 (T7) alone, Asn207 (T14) alone, or any combination thereof, and comprise a relative abundance of S1G1F of less than or equal to about 12%, less than or equal to about 11%, less than or equal to about 10%, less than or equal to about 9%, less than or equal to about 8%, less than or equal to about 7%, less than or equal to about 6%, less than or equal to about 5%, less than or equal to about 4%, less than or equal to about 3%, less than or equal to about 2%, less than or equal to about 1%, or equal to about 0%.

In some aspects, the one or more N-linked glycans are located at residue Asn76 (T5) alone, Asn108 (T7) alone, Asn207 (T14) alone, or any combination thereof, and comprise a relative abundance of S1G2F of more than or equal to about 33% or of about 32% to about 49%. In some aspects, the one or more N-linked glycans are located at residue Asn76 (T5) alone, Asn108 (T7) alone, Asn207 (T14) alone, or any combination thereof, and comprise a relative abundance of S1G2F of more than or equal to about 34%, more than or equal to about 35%, more than or equal to about 36%, more than or equal to about 37%, more than or equal to about 38%, more than or equal to about 39%, more than or equal to about 40%, more than or equal to about 41%, more than or equal to about 42%, more than or equal to about 43%, more than or equal to about 44%, more than or equal to about 45%, more than or equal to about 46%, more than or equal to about 47%, more than or equal to about 48%, or more than or equal to about 49%. In some aspects, the one or more N-linked glycans are located at residue Asn76 (T5) alone, Asn108 (T7) alone, Asn207 (T14) alone, or any combination thereof, and comprise a relative abundance of S1G2F of about 33% to about 49%, about 34% to about 49%, about 35% to about 49%, about 36% to about 49%, about 37% to about 49%, about 38% to about 49%, about 39% to about 49%, about 40% to about 49%, about 41% to about 49%, about 42% to about 49%, about 43% to about 49%, about 44% to about 49%, about 45% to about 49%, about 46% to about 49%, about 47% to about 49%, or about 48% to about 49%.

In some aspects, the one or more N-linked glycans are located at residue Asn76 (T5) alone, Asn108 (T7) alone, Asn207 (T14) alone, or any combination thereof, and comprise a relative abundance of S2G2F of more than or equal to about 12% or of about 14% to about 48.5%. In some aspects, the one or more N-linked glycans are located at residue Asn76 (T5) alone, Asn108 (T7) alone, Asn207 (T14) alone, or any combination thereof, and comprise a relative abundance of S2G2F of about 15% to about 45.5%, about 15% to about 45.5%, about 16% to about 45.5%, about 16% to about 45.5%, about 17% to about 45.5%, about 18% to about 45.5%, about 19% to about 45.5%, about 20% to about 45.5%, about 21% to about 45.5%, about 22% to about 45.5%, about 23% to about 45.5%, about 24% to about 45.5%, about 25% to about 45.5%, about 26% to about 45.5%, about 27% to about 45.5%, about 28% to about 45.5%, about 29% to about 45.5%, about 30% to about 45.5%, about 31% to about 45.5%, about 32% to about 45.5%, about 33% to about 45.5%, about 34% to about 45.5%, about 35% to about 45.5%, about 36% to about 45.5%, about 37% to about 45.5%, about 38% to about 45.5%, about 39% to about 45.5%, about 40% to about 45.5%, about 41% to about 45.5%, about 42% to about 45.5%, about 43% to about 45.5%, about 44% to about 45.5%, about 44% to about 45.5%, or about 45% to about 45.5%.

In some aspects, the one or more N-linked glycans are located at residue Asn76 (T5) alone, Asn108 (T7) alone, Asn207 (T14) alone, or any combination thereof, and comprise a relative abundance of G2F comprising a relative abundance of about 1.5% to about 23%, S1G2F comprising a relative abundance of about 32% to about 49%, and/or S2G2F comprising a relative abundance of about 14% to about 48.5%.

In some aspects, the one or more N-linked glycans are located at residue Asn76 (T5) alone, Asn108 (T7) alone, Asn207 (T14) alone, or any combination thereof, and comprise a relative abundance of G2F comprising a relative abundance of less than or equal to about 25%, S1G2F comprising a relative abundance of more than or equal to about 33%, and/or S2G2F comprising a relative abundance of more than or equal to about 12%.

In some aspects, the one or more N-linked glycans are located at residue Asn76 (T5) alone, Asn108 (T7) alone, Asn207 (T14) alone, or any combination thereof, and comprise a relative abundance of G0F comprising a relative abundance of less than or equal to about 6.5%, G1F comprising a relative abundance of less than or equal to about 7%, G2F comprising a relative abundance of about 1.5% to about 23%, S1G1F comprising a relative abundance of less than or equal to about 12.5%, S1G2F comprising a relative abundance of about 32% to about 49%, and/or S2G2F comprising a relative abundance of about 14% to about 48.5%.

In some aspects, the one or more N-linked glycans are located at residue Asn76 (T5) alone, Asn108 (T7) alone, Asn207 (T14) alone, or any combination thereof, and comprise a relative abundance of G0F comprising a relative abundance of less than or equal to about 7.0%, G1F comprising a relative abundance of less than or equal to about 7.5%, G2F comprising a relative abundance of less than or equal to about 25%, S1G1F comprising a relative abundance of less than or equal to about 13.5%, S1G2F comprising a relative abundance of more than or equal to about 33%, and/or S2G2F comprising a relative abundance of more than or equal to about 12%.

The methods of the present disclosure are also useful for characterizing, analyzing, or controlling the sialic acid content of proteins. In some aspects, the one or more N-linked glycans are sialic acid and have a molar ratio of NANA of from about 8 to about 11. In some aspects, the one or more N-linked glycans are sialic acid and have a molar ratio of NANA of from about 8.3 to about 11, from about 9.5 and about 10.1, or from about 8.3 to about 10.1. In some aspects, the one or more N-linked glycans are sialic acid and have a molar ratio of NANA of from about 8.3 to about 11. In some aspects, the one or more N-linked glycans are sialic acid and have a molar ratio of NANA of from about 9.5 to about 10.1. In some aspects, the one or more N-linked glycans are sialic acid and have a molar ratio of NANA of from about 8.3 to about 10.1. In some aspects, the one or more N-linked glycans are sialic acid and have a molar ratio of NANA of from about 8 to about 11. In some aspects, the one or more N-linked glycans are sialic acid and have a molar ratio of NANA of from about 8 to about 10. In some aspects, the one or more N-linked glycans are sialic acid and have a molar ratio of NANA of from about 9 to about 10.

In some aspects, the one or more N-linked glycans are sialic acid and have a molar ratio of NANA of from about 0.1 to about 2.0. In some aspects, the one or more N-linked glycans are sialic acid and have a molar ratio of NANA of from 0.90 to about 1.20 or from about 0.3 to about 1.2. In some aspects, the one or more N-linked glycans are sialic acid and have a molar ratio of NANA of from 0.80 to about 1.20. In some aspects, the one or more N-linked glycans are sialic acid and have a molar ratio of NANA of from 0.80 to about 1.30. In some aspects, the one or more N-linked glycans are sialic acid and have a molar ratio of NANA of from 0.80 to about 1.40. In some aspects, the one or more N-linked glycans are sialic acid and have a molar ratio of NANA of from 0.70 to about 1.40. In some aspects, the one or more N-linked glycans are sialic acid and have a molar ratio of NANA of from 0.70 to about 1.50. In some aspects, the one or more N-linked glycans are sialic acid and have a molar ratio of NANA of from about 0.1 to about 2. In some aspects, the one or more N-linked glycans are sialic acid and have a molar ratio of NANA of from about 0.9 to about 1.2. In some aspects, the one or more N-linked glycans are sialic acid and have a molar ratio of NANA of from about 0.3 to about 1.2. In some aspects, the one or more N-linked glycans are sialic acid and have a molar ratio of NANA of from about 0.8 to about 1.2. In some aspects, the one or more N-linked glycans are sialic acid and have a molar ratio of NANA of from about 0.8 to about 1.3. In some aspects, the one or more N-linked glycans are sialic acid and have a molar ratio of NANA of from about 0.8 to about 1.4. In some aspects, the one or more N-linked glycans are sialic acid and have a molar ratio of NANA of from about 0.7 to about 1.4. In some aspects, the one or more N-linked glycans are sialic acid and have a molar ratio of NANA of from about 0.7 to about 1.5. In some aspects, the one or more N-linked glycans are sialic acid and have a molar ratio of NANA of from about 0.8 to about 1.5.

The methods of the present disclosure are also useful or analyzing the sialylation profile of the glycans present on the protein. In some aspects, the glycosylation profile includes one or more asialylated glycans (Domain I), mono-sialylated glycans (Domain II), di-sialylated glycans (Domain III), and/or tri-sialylated and tetra-sialylated glycans (Domain IV+V). These domains can be analyzed via Imaged Capillary Isoelectric Focusing (iCIEF), which refers to a method used for the separation of proteins by their isoelectric point (pI). In this method, samples are prepared to a final concentration of ~1 mg/mL with water, methyl cellulose, ampholytes, and pI markers, and then injected by an autosampler into an imaged capillary isoelectric focusing system (iCIEF). Electrophoresis separates the samples through a pH gradient within a fluorocarbon (FC) coated capillary based on charge variance of the isoforms. Results are then compared to reference separations to compare and characterize groups of components.

In some aspects, the asialylated glycans (Domain I) have a molar ratio of from about 28 to about 37, from about 29 to about 32, from about 28 to about 32, or from about 29 to about 37. In some aspects, the asialylated glycans (Domain I) have a molar ratio of from about 28 to about 37. In some aspects, the asialylated glycans (Domain I) have a molar ratio of from about 26 to about 40. In some aspects, the asialylated glycans (Domain I) have a molar ratio of from about 28 to about 39. In some aspects, the asialylated glycans (Domain I) have a molar ratio of from about 29 to about 39. In some aspects, the asialylated glycans (Domain I) have a molar ratio of from about 29 to about 38. In some aspects, the asialylated glycans (Domain I) have a molar ratio of from about 29 to about 37. In some aspects, the asialylated glycans (Domain I) have a molar ratio of from about 30 to about 37.

In some aspects, the asialylated glycans (Domain I) have a molar ratio of about 25. In some aspects, the asialylated glycans (Domain I) have a molar ratio of about 25.5. In some aspects, the asialylated glycans (Domain I) have a molar ratio of about 26. In some aspects, the asialylated glycans (Domain I) have a molar ratio of about 26.5. In some aspects, the asialylated glycans (Domain I) have a molar ratio of about 27. In some aspects, the asialylated glycans (Domain I) have a molar ratio of about 27.5. In some aspects, the asialylated glycans (Domain I) have a molar ratio of about 28. In some aspects, the asialylated glycans (Domain I) have a molar ratio of about 28.5. In some aspects, the asialylated glycans (Domain I) have a molar ratio of about 29. In some aspects, the asialylated glycans (Domain I) have a molar ratio of about 29.5. In some aspects, the asialylated glycans (Domain I) have a molar ratio of about 30. In some aspects, the asialylated glycans (Domain I) have a molar ratio of about 30.5. In some aspects, the asialylated glycans (Domain I) have a molar ratio of about 31. In some aspects, the asialylated glycans (Domain I) have a molar ratio of about 31.5. In some aspects, the asialylated glycans (Domain I) have a molar ratio of about 32. In some aspects, the asialylated glycans (Domain I) have a molar ratio of about 32.5. In some aspects, the asialylated glycans (Domain I) have a molar ratio of about 33. In some aspects, the asialylated glycans (Domain I) have a molar ratio of about 33.5. In some aspects, the asialylated glycans (Domain I) have a molar ratio of about 34. In some aspects, the asialylated glycans (Domain I) have a molar ratio of about 34.5. In some aspects, the asialylated glycans (Domain I) have a molar ratio of about 35. In some aspects, the asialylated glycans (Domain I) have a molar ratio of about 35.5. In some aspects, the asialylated glycans (Domain I) have a molar ratio of about 36. In some aspects, the asialylated glycans (Domain I) have a molar ratio of about 36.5. In some aspects, the asialylated glycans (Domain I) have a molar ratio of about 37. In some aspects, the asialylated glycans (Domain I) have a molar ratio of about 37.5. In some aspects, the asialylated glycans (Domain I) have a molar ratio of about 38. In some aspects, the asialylated glycans (Domain I) have a molar ratio of about 38.5. In some aspects, the asialylated glycans (Domain I) have a molar ratio of about 39. In some aspects, the asialylated glycans (Domain I) have a molar ratio of about 39.5. In some aspects, the asialylated glycans (Domain I) have a molar ratio of about 40. In some aspects, the asialylated glycans (Domain I) have a molar ratio of about 31.

In some aspects, the mono-sialylated glycans (Domain II) have a molar ratio of from about 26 to about 28, from about 27 to about 33, from about 26 to from about 33, from about 27 to about 28. In some aspects, the mono-sialylated glycans (Domain II) have a molar ratio of from about 26 to about 33. In some aspects, the mono-sialylated glycans (Domain II) have a molar ratio of from about 26 to about 28. In some aspects, the mono-sialylated glycans (Domain II) have a molar ratio of from about 27 to about 28. In some aspects, the mono-sialylated glycans (Domain II) have a molar ratio of from about 27 to about 29. In some aspects, the mono-sialylated glycans (Domain II) have a molar ratio of from about 27 to about 30. In some aspects, the mono-sialylated glycans (Domain II) have a molar ratio of from about 27 to about 31. In some aspects, the mono-sialylated glycans (Domain II) have a molar ratio of from about 27 to about 32. In some aspects, the mono-sialylated glycans (Domain II) have a molar ratio of from about 27 to about 33.

In some aspects, the mono-sialylated glycans (Domain II) have a molar ratio of about 20. In some aspects, the mono-sialylated glycans (Domain II) have a molar ratio of about 20.5. In some aspects, the mono-sialylated glycans (Domain II) have a molar ratio of about 21. In some aspects, the mono-sialylated glycans (Domain II) have a molar ratio of about 21.5. In some aspects, the mono-sialylated glycans (Domain II) have a molar ratio of about 22. In some aspects, the mono-sialylated glycans (Domain II) have a molar ratio of about 22.5. In some aspects, the mono-sialylated glycans (Domain II) have a molar ratio of about 23. In some aspects, the mono-sialylated glycans (Domain II) have a molar ratio of about 23.5. In some aspects, the mono-sialylated glycans (Domain II) have a molar ratio of about 24. In some aspects, the mono-sialylated glycans (Domain II) have a molar ratio of about 24.5. In some aspects, the mono-sialylated glycans (Domain II) have a molar ratio of about 25. In some aspects, the mono-sialylated glycans (Domain II) have a molar ratio of about 25.5. In some aspects, the mono-sialylated glycans (Domain II) have a molar ratio of about 26. In some aspects, the mono-sialylated glycans (Domain II) have a molar ratio of about 26.5. In some aspects, the mono-sialylated glycans (Domain II) have a molar ratio of about 27. In some aspects, the mono-sialylated glycans (Domain II) have a molar ratio of about 27.5. In some aspects, the mono-sialylated glycans (Domain II) have a molar ratio of about 28. In some aspects, the mono-sialylated glycans (Domain II) have a molar ratio of about 28.5. In some aspects, the mono-sialylated glycans (Domain II) have a molar ratio of about 29. In some aspects, the mono-sialylated glycans (Domain II) have a molar ratio of about 29.5. In some aspects, the mono-sialylated glycans (Domain II) have a molar ratio of about 30. In some aspects, the mono-sialylated glycans (Domain II) have a molar ratio of about 30.5. In some aspects, the mono-sialylated glycans (Domain II) have a molar ratio of about 31. In some aspects, the mono-sialylated glycans (Domain II) have a molar ratio of about 31.5. In some aspects, the mono-sialylated glycans (Domain II) have a molar ratio of about 32. In some aspects, the mono-sialylated glycans (Domain II) have a molar ratio of about 32.5. In some aspects, the mono-sialylated glycans (Domain II) have a molar ratio of about 33. In some aspects, the mono-sialylated glycans (Domain II) have a molar ratio of about 33.5. In some aspects, the mono-sialylated glycans (Domain II) have a molar ratio of about 34. In some aspects, the mono-sialylated glycans (Domain II) have a molar ratio of about 34.5. In some aspects, the mono-sialylated glycans (Domain II) have a molar ratio of about 35. In some aspects, the mono-sialylated glycans (Domain II) have a molar ratio of about 27.

In some aspects, the di-sialylated glycans (Domain III) have a molar ratio of from about 27 to about 28, from about 22 to about 31, from about 27 to about 31, or from about 22 to about 28. In some aspects, the di-sialylated glycans (Domain III) have a molar ratio of from about 22 to about 28. In some aspects, the di-sialylated glycans (Domain III) have a molar ratio of from about 22 to about 31. In some aspects, the di-sialylated glycans (Domain III) have a molar ratio of from about 24 to about 31. In some aspects, the di-sialylated glycans (Domain III) have a molar ratio of from about 25 to about 31. In some aspects, the di-sialylated glycans (Domain III) have a molar ratio of from about 27 to about 28. In some aspects, the di-sialylated glycans (Domain III) have a molar ratio of from about 27 to about 35.

In some aspects, the di-sialylated glycans (Domain III) have a molar ratio of about 20. In some aspects, the di-sialylated glycans (Domain III) have a molar ratio of about 20.5. In some aspects, the di-sialylated glycans (Domain III) have a molar ratio of about 21. In some aspects, the di-sialylated glycans (Domain III) have a molar ratio of about 21.5. In some aspects, the di-sialylated glycans (Domain III) have a molar ratio of about 22. In some aspects, the di-sialylated glycans (Domain III) have a molar ratio of about 22.5. In some aspects, the di-sialylated glycans (Domain III) have a molar ratio of about 23. In some aspects, the di-sialylated glycans (Domain III) have a molar ratio of about 23.5. In some aspects, the di-sialylated glycans (Domain III) have a molar ratio of about 24. In some aspects, the di-sialylated glycans (Domain III) have a molar ratio of about 24.5. In some aspects, the di-sialylated glycans (Domain III) have a molar ratio of about 25. In some aspects, the di-sialylated glycans (Domain III) have a molar ratio of about 25.5. In some aspects, the di-sialylated glycans (Domain III) have a molar ratio of about 26. In some aspects, the di-sialylated glycans (Domain III) have a molar ratio of about 26.5. In some aspects, the di-sialylated glycans (Domain III) have a molar ratio of about 27. In some aspects, the di-sialylated glycans (Domain III) have a molar ratio of about 27.5. In some aspects, the di-sialylated glycans (Domain III) have a molar ratio of about 28. In some aspects, the di-sialylated glycans (Domain III) have a molar ratio of about 28.5. In some aspects, the di-sialylated glycans (Domain III) have a molar ratio of about 29. In some aspects, the di-sialylated glycans (Domain III) have a molar ratio of about 29.5. In some aspects, the di-sialylated glycans (Domain III) have a molar ratio of about 30. In some aspects, the di-sialylated glycans (Domain III) have a molar ratio of about 30.5. In some aspects, the di-sialylated glycans (Domain III) have a molar ratio of about 31. In some aspects, the di-sialylated glycans (Domain III) have a molar ratio of about 31.5. In some aspects, the di-sialylated glycans (Domain III) have a molar ratio of about 32. In some aspects, the di-sialylated glycans (Domain III) have a molar ratio of about 32.5. In some aspects, the di-sialylated glycans (Domain III) have a molar ratio of about 33. In some aspects, the di-sialylated glycans (Domain III) have a molar ratio of about 33.5. In some aspects, the di-sialylated glycans (Domain III) have a molar ratio of about 34. In some aspects, the di-sialylated glycans (Domain III) have a molar ratio of about 34.5. In some aspects, the di-sialylated glycans (Domain III) have a molar ratio of about 35. In some aspects, the di-sialylated glycans (Domain III) have a molar ratio of about 27.4.

In some aspects, the tri-sialylated and tetra-sialylated glycans (Domain IV+V) have a molar ratio of from about 13 to about 16, from about 8 to about 16, or from about 8 to about 16. In some aspects, the tri-sialylated and tetra-sialylated glycans (Domain IV+V) have a molar ratio of from about 8 to about 20. In some aspects, the tri-sialylated and tetra-sialylated glycans (Domain IV+V) have a molar ratio of from about 8 to about 16. In some aspects, the tri-sialylated and tetra-sialylated glycans (Domain IV+V) have a molar ratio of from about 10 to about 16. In some aspects, the tri-sialylated and tetra-sialylated glycans (Domain IV+V) have a molar ratio of from about 12 to about 16. In some aspects, the tri-sialylated and tetra-sialylated glycans (Domain IV+V) have a molar ratio of from about 13 to about 20. In some aspects, the tri-sialylated and tetra-sialylated glycans (Domain IV+V) have a molar ratio of from about 13 to about 18. In some aspects, the tri-sialylated and tetra-sialylated glycans (Domain IV+V) have a molar ratio of from about 13 to about 16. In some aspects, the tri-sialylated and tetra-sialylated glycans (Domain IV+V) have a molar ratio of from about 13 to about 16.

In some aspects, the tri-sialylated and tetra-sialylated glycans (Domain IV+V) have a molar ratio of about 5. In some aspects, the tri-sialylated and tetra-sialylated glycans (Domain IV+V) have a molar ratio of about 5.5. In some aspects, the tri-sialylated and tetra-sialylated glycans (Domain IV+V) have a molar ratio of about 6. In some aspects, the tri-sialylated and tetra-sialylated glycans (Domain IV+V) have a molar ratio of about 6.5. In some aspects, the tri-sialylated and tetra-sialylated glycans (Domain IV+V) have a molar ratio of about 7. In some aspects, the tri-sialylated and tetra-sialylated glycans (Domain IV+V) have a molar ratio of about 7.5. In some aspects, the tri-sialylated and tetra-sialylated glycans (Domain IV+V) have a molar ratio of about 8. In some aspects, the tri-sialylated and tetra-sialylated glycans (Domain IV+V) have a molar ratio of about 8.5. In some aspects, the tri-sialylated and tetra-sialylated glycans (Domain IV+V) have a molar ratio of about 9. In some aspects, the tri-sialylated and tetra-sialylated glycans (Domain IV+V) have a molar ratio of about 9.5. In some aspects, the tri-sialylated and tetra-sialylated glycans (Domain IV+V) have a molar ratio of about 10. In some aspects, the tri-sialylated and tetra-sialylated glycans (Domain IV+V) have a molar ratio of about 10.5. In some aspects, the tri-sialylated and tetra-sialylated glycans (Domain IV+V) have a molar ratio of about 11. In some aspects, the tri-sialylated and tetra-sialylated glycans (Domain IV+V) have a molar ratio of about 11.5. In some aspects, the tri-sialylated and tetra-sialylated glycans (Domain IV+V) have a molar ratio of about 12. In some aspects, the tri-sialylated and tetra-sialylated glycans (Domain IV+V) have a molar ratio of about 12.5. In some aspects, the tri-sialylated and tetra-sialylated glycans (Domain IV+V) have a molar ratio of about 13. In some aspects, the tri-sialylated and tetra-sialylated glycans (Domain IV+V) have a molar ratio of about 13.5. In some aspects, the tri-sialylated and tetra-sialylated glycans (Domain IV+V) have a molar ratio of about 14. In some aspects, the tri-sialylated and tetra-sialylated glycans (Domain IV+V) have a molar ratio of about 14.5. In some aspects, the tri-sialylated and tetra-sialylated glycans (Domain IV+V) have a molar ratio of about 15. In some aspects, the tri-sialylated and tetra-sialylated glycans (Domain IV+V) have a molar ratio of about 15.5. In some aspects, the tri-sialylated and tetra-sialylated glycans (Domain IV+V) have a molar ratio of about 16. In some aspects, the tri-sialylated and tetra-sialylated glycans (Domain IV+V) have a molar ratio of about 16.5. In some aspects, the tri-sialylated and tetra-sialylated glycans (Domain IV+V) have a molar ratio of about 17. In some aspects, the tri-sialylated and tetra-sialylated glycans (Domain IV+V) have a molar ratio of about 17.5. In some aspects, the tri-sialylated and tetra-sialylated glycans (Domain IV+V) have a molar ratio of about 18. In some aspects, the tri-sialylated and tetra-sialylated glycans (Domain IV+V) have a molar ratio of about 18.5. In some aspects, the tri-sialylated and tetra-sialylated glycans (Domain IV+V) have a molar ratio of about 19. In some aspects, the tri-sialylated and tetra-sialylated glycans (Domain IV+V) have a molar ratio of about 19.5. In some aspects, the tri-sialylated and tetra-sialylated glycans (Domain IV+V) have a molar ratio of about 20. In some aspects, the tri-sialylated and tetra-sialylated glycans (Domain IV+V) have a molar ratio of about 14.6.

The methods of the present disclosure are also useful for analyzing O-linked glycans. In some aspects, the glycosylation profile includes one or more O-linked glycans. In some aspects, the O-linked glycans are located at residues Ser129, Ser130, Ser136, and/or Ser139.

In some aspects, a CTLA4-Fc fusion protein described herein comprises a C-terminal lysine. In some aspects, the C-terminal lysine comprises a relative abundance of about 20% to about 25%. In some aspects, wherein the C-terminal lysine comprises a relative abundance of about 3% to about 10%.

The methods of the present disclosure are also useful for analyzing bi-antennary glycans of a CTLA4-Fc fusion protein, comprising measuring one or more N-linked glycans attached to one or more asparagine residues in the CTLA4 protein, wherein one of the bi-antennary glycans is G2F. In some aspects, one or more N-linked glycans attached to one or more asparagine residues in the CTLA4 protein are measured, wherein one of the bi-antennary glycans is G0F. In some aspects, the bi-antennary glycans are selected from a group consisting of G0F, G1F, G2F, S1G1F, S1G2F, and/or S2G2F. Liquid chromatography can be used to analyze the glycans of the present disclosure. A particular glycoprotein can display heterogeneity of carbohydrates. Heterogeneity can be seen at several levels: glycosylation sites can vary from completely occupied to unoccupied, and any specific site can be populated with many different oligosaccharide structures, wherein each structure can be modified by sialic acid molecules, such as NANA or NANA.

In some aspects, the present disclosure provides a method of analyzing bi-antennary glycans of a CTLA4-Fc fusion protein, comprising performing isoelectric focusing of the CTLA4-Fc fusion protein. In some aspects, the isoelectric focusing is imaged capillary isoelectric focusing. In some aspects, the isoelectric focused CTLA4-Fc fusion protein forms group I, group II, and group III. In some aspects, group I is less than or equal to 4% of total, group II is greater than or equal to 87% of total, and/or group III is less than or equal to 10% of total.

The carbohydrate content of the protein of the present disclosure can be analyzed by methods known in the art, including methods described in the Examples herein. Several methods are known in the art for glycosylation analysis and are useful in the context of the present disclosure. These methods provide information regarding the identity and the composition of the oligosaccharide attached to the produced peptide. Methods for carbohydrate analysis useful in connection with the present disclosure include, but are not limited to, lectin chromatography; high performance anion-exchange chromatography combined with pulsed amperometric detection (HPAEC-PAD), which uses high pH anion exchange chromatography to separate oligosaccharides based on charge; NMR; Mass spectrometry; HPLC; porous graphitized carbon (GPC) chromatography.

Methods for releasing oligosaccharides include 1) enzymatic methods, which are commonly performed using peptide-N-glycosidase F/endo-α-galactosidase; 2) β-elimination methods, using a harsh alkaline environment to release mainly O-linked structures; and 3) chemical methods using anhydrous hydrazine to release both N- and O-linked oligosaccharides. Methods for analysis can comprise one or more of the following steps: 1. dialyzing the sample against deionized water to remove all buffer salts, followed by lyophilization; 2. releasing intact oligosaccharide chains with anhydrous hydrazine; 3. treating the intact oligosaccharide chains with anhydrous methanolic HCl to liberate individual monosaccharides as O-methyl derivatives; 4. N-acetylating any primary amino groups; 5. derivatizing to yield per-O-trimethylsilyl methyl glycosides; 6. Separating the derivatives by capillary gas-liquid chromatography (GLC) on a CP-SIL8 column; 7. identifying individual glycoside derivatives by retention time from the GLC and mass spectroscopy, compared to known standards; and 8. quantifying individual derivatives by FID with an internal standard (13-O-methyl-D-glucose). In some aspects, the bi-antennary glycans are measured via Ultra Performance Liquid Chromatography with fluorescence detection (UPLC-FLR). In some aspects, the Fc domain of the CTLA4-Fc fusion protein is cleaved prior to the measuring. In some aspects, the protein is run through a viral inactivation process. In some aspects, the viral inactivation process is run with 0.5% Triton X-100.

IV. Pharmaceutical Compositions

The compositions prepared by the methods of the present disclosure also contemplate pharmaceutical formulations. A composition that is acceptable for pharmaceutical administration, such a composition can include substances that are impurities at a level not exceeding an acceptable level for pharmaceutical administration (such level including an absence of such impurities), and can include pharmaceutically acceptable excipients, vehicles, carriers and other inactive ingredients, for example, to formulate such composition for ease of administration, in addition to any active agent(s). For example, a pharmaceutically acceptable CTLA4-Ig composition can include MCP-1 or DNA, so long as those substances are at a level acceptable for administration to humans.

The disclosure also provides any of the described CTLA4-Ig molecules as a lyophilized mixture. Formulations comprising CTLA4-Ig to be lyophilized can further comprise three basic components: (1) an additional active ingredient(s) including other proteins or small molecules (such as immunosuppressants), (2) an excipient(s) and (3) a solvent(s). Excipients include pharmaceutically acceptable reagents to provide good lyophilized cake properties (bulking agents) as well as to provide lyoprotection and/or cryoprotection of proteins ("stabilizer"), maintenance of pH (buffering agents), and proper conformation of the protein during storage so that substantial retention of biological activity (including active ingredient stability, such as protein stability) is maintained. With respect to excipients, an example of a formulation can include one or more of a buffering agent(s), a bulking agent(s), a protein stabilizer(s) and an antimicrobial(s). Sugars or polyols can be used as nonspecific protein stabilizers in solution and during freeze-thawing and freeze-drying. Polymers can be used to stabilize proteins in solution and during freeze-thawing and freeze-drying. One popular polymer is serum albumin, which has been used both as a cryoprotectant and lyoprotectant. In one aspect, the disclosure provides formulations that are albumin free. Various salts can be used as bulking agents. Illustrative salt bulking agents include, for example, NaCl, MgCl2 and CaCl2.

Certain amino acids can be used as cryoprotectants and/or lyoprotectants and/or bulking agents. Amino acids that can be used include, but are not limited to, glycine, proline, 4-hydroxyproline, L-serine, sodium glutamate, alanine, arginine and lysine hydrochloride. Many buffering agents covering a wide pH range are available for selection in formulations. Buffering agents include, for example, acetate, citrate, glycine, histidine, phosphate (sodium or potassium), diethanolamine and Tris. Buffering agents encompasses those agents which maintain the solution pH in an acceptable range prior to lyophilization. In one aspect, the disclosure provides a lyophilized CTLA4-Ig mixture comprising at least 90%, 95%, 99%, or 99.5% CTLA4-Ig dimer, including any sequence according to any one of SEQ ID Nos: 1-8. In one aspect, the disclosure provides a lyophilized CTLA4-Ig mixture comprising at least 90%, 95%, 99%, or 99.5% CTLA4-Ig dimer and not more than 5%, 4%, 3%, 2%, or 1% CTLA4-Ig tetramer. In another aspect, the disclosure provides a lyophilized CTLA4-Ig mixture comprising at least 90%, 95%, 99%, or 99.5% CTLA4-Ig dimer, and not more than 5%, 4%, 3%, 2%, or 1% CTLA4-Ig tetramer, and not more than 2%, 1.5%, 1.0%, 0.8%, 0.5%, or 0.3% CTLA4-Ig monomer. In a further aspect, the disclosure provides a lyophilized CTLA4-Ig mixture comprising at least 8.0 moles of sialic acid per mole of CTLA4-Ig dimer or to CTLA4-Ig molecule. In another aspect, the disclosure provides a lyophilized CTLA4-Ig mixture comprising: from about 15 to about 35 moles of GlcNac per mole of CTLAIg molecules or dimer; from about 1 to about 5 moles of GalNac per mole of CTLA4-Ig dimer or to CTLA4-Ig molecule; from about 5 moles to about 20 moles of galactose per mole of CTLA4-Ig dimer or to CTLA4-Ig molecule; from about 2 to about 10 moles of fucose per mole of CTLA4-Ig dimer or to CTLA4-Ig molecule; and/or from about 5-15 moles of mannose per mole of CTLA4-Ig dimer or to CTLA4-Ig molecule.

The disclosure also provides any of the described CTLA4-Ig molecules as a subcutaneous (SC) formulation. An IV formulation is inconvenient for a subject in need of frequent, chronic therapy. The subject has to make frequent trips to receive drug via an IV infusion that may last as long as an hour. Consequently, a SC formulation that could be self-administered at home would be very beneficial. For subcutaneous administration, a dosage form with high protein concentrations is desired. Treatments with high doses of more than 1 mg/kg (>100 mg per dose) require development of formulations at concentrations exceeding 100 mg/ml because of the small volume (<1.5 ml) that can be given by the SC routes. The SC formulations of the disclosure comprise the CTLA4Ig molecule at a protein concentration of at least 100 mg/ml in combination with a sugar at stabilizing levels, preferably a protein concentration of at least 125 mg/ml in combination with a sugar at stabilizing levels, in an aqueous carrier. The sugar is preferably in a weight ratio of at least 1:1.1 protein to sugar. The stabilizer is preferably employed in an amount no greater than that which may result in a viscosity undesirable or unsuitable for administration via SC syringe. The sugar is preferably disaccharides, most preferably sucrose. The SC formulation may also comprise one or more of the components selected from the list consisting of buffering agents, surfactants, and preservatives.

V. Methods of Treatment

The compositions prepared by the methods of the present disclosure are useful to treat a variety of diseases. The disclosure provides for a method for inhibiting T cell proliferation (or activation), the method comprising contacting a T cell with an effective amount of a CTLA4-Ig composition of the disclosure. The disclosure provides for a method for inhibiting an immune response in a subject, the method comprising administering to a subject in need thereof an effective amount of a CTLA4-Ig composition of the disclosure. The disclosure provides for a method for inducing immune tolerance to an antigen in a subject, the method comprising administering to a subject in need thereof an effective amount of a CTLA4-Ig composition of the disclosure. The disclosure provides for a method for treating inflammation in a subject, the method comprising administering to a subject in need thereof an effective amount of a CTLA4-Ig composition of the disclosure. The disclosure provides for a method for treating rheumatoid arthritis comprising administering to a subject in need thereof an effective amount of a CTLA4-Ig composition of the disclosure.

The disclosure provides for a method for treating psoriasis in a subject, the method comprising administering to a subject in need thereof an effective amount of a CTLA4-Ig composition of the disclosure. The disclosure provides for a method for treating or preventing an allergy in a subject, the method comprising administering to a subject in need thereof an effective amount of a CTLA4-Ig composition of the disclosure. The disclosure provides for a method for treating or preventing graft vs host disease in a subject, the method comprising administering to a subject in need thereof an effective amount of a CTLA4-Ig composition of the disclosure. The disclosure provides for a method for treating or preventing rejection of a transplanted organ in a subject, the method comprising administering to a subject in need thereof an effective amount of a CTLA4-Ig composition of the disclosure.

The disclosure provides for a method for treating Crohn's Disease in a subject, the method comprising administering to a subject in need thereof an effective amount of a CTLA4-Ig composition of the disclosure. The disclosure provides a method for treating type I diabetes in a subject, the method comprising administering to a subject in need thereof an effective amount of a CTLA4-Ig composition of the disclosure.

The disclosure provides a method for treating oophoritis in a subject, the method comprising administering to a subject in need thereof an effective amount of a CTLA4-Ig composition of the disclosure. The disclosure provides a method for treating glomerulonephritis in a subject, the method comprising administering to a subject in need thereof an effective amount of a CTLA4-Ig composition of the disclosure. The disclosure provides a method for treating allergic encephalomyelitis in a subject, the method comprising administering to a subject in need thereof an effective amount of a CTLA4-Ig composition of the disclosure.

The disclosure provides a method for treating myasthenia gravis in a subject, the method comprising administering to a subject in need thereof an effective amount of a CTLA4-Ig composition of the disclosure. Thus, in certain aspects of the disclosure, the disclosure provides CTLA4-Ig molecules produced by a cell line in a production method described herein in order to treat T-cell related diseases or disorders, that include but are not limited to, generally any T-cell dependent lymphoproliferative disease or disorder and any T-cell dependent autoimmune disease or disorder, and more specifically: T cell lymphoma, T cell acute lymphoblastic leukemia, testicular angiocentric T cell lymphoma, benign lymphocytic angiitis, graft versus host disease (GVHD), immune disorders associated with graft transplantation rejection, psoriasis, inflammation, allergy, oophoritis, glomerulonephritis, encephalomyelitis, Hashimoto's thyroiditis, Graves' disease, Addison's disease, primary myxedema, pernicious anemia, autoimmune atrophic gastritis, rheumatoid arthritis, insulin dependent diabetes mellitis, good pasture's syndrome, myasthenia gravis, pemphigus, sympathetic ophthalmia, autoimmune uveitis, autoimmune hemolytic anemia, idiopathic thrombocytopenia, primary biliary cirrhosis, chronic action hepatitis, scleroderma, polymyositis, and mixed connective tissue disease.

The disclosure provides for a method for inhibiting T cell proliferation (or activation), the method comprising contacting a T cell with an effective amount of a CTLA4-Ig composition of the disclosure in combination with or without another agent, such as methotrexate. The disclosure provides a method for inhibiting an immune response in a subject, the method comprising administering to a subject in need thereof an effective amount of a CTLA4-Ig composition of the disclosure either alone or in combination with methotrexate. The disclosure provides a method for inducing immune tolerance to an antigen in a subject, the method comprising administering to a subject in need thereof an effective amount of a CTLA4-Ig composition of the disclosure in combination with methotrexate.

Various aspects of the disclosure are described in further detail in the following subsections. The present disclosure is further illustrated by the following examples which should not be construed as further limiting. The contents of all references cited throughout this application are expressly incorporated herein by reference.

EXAMPLES

Example 1

5 L Bench Scale Manufacturing

Abatacept is a genetically engineered fusion protein, which consists of the functional binding domain of human Cytotoxic T-Lymphocyte Antigen-4 (CTLA-4) and the Fc domain of human monoclonal immunoglobulin, of the IgG1 class. Abatacept is comprised of 2 homologous glycosylated polypeptide chains of approximately 46 kDa each which are covalently linked through a single disulfide bond.

Abatacept is produced as an extracellular protein in large-scale cell culture using a Chinese hamster ovary (CHO) cell line. The manufacturing process is initiated with the thawing of a working cell bank (WCB) vial. The culture is propagated in a series of baffled shake flasks, cell bag bioreactors and seed bioreactors. The final stage inoculum culture is transferred to the production bioreactor. The production bioreactor is harvested based on a target sialic acid (SA) to abatacept protein molar ratio (MR) and cell culture duration. The cell culture harvest is clarified using primary recovery harvest steps followed by sterilizing grade filtration. The cell-free harvest material is adjusted to achieve a specified pH, and Triton X-100 is added for viral inactivation in preparation for downstream processing.

Figure 1B:
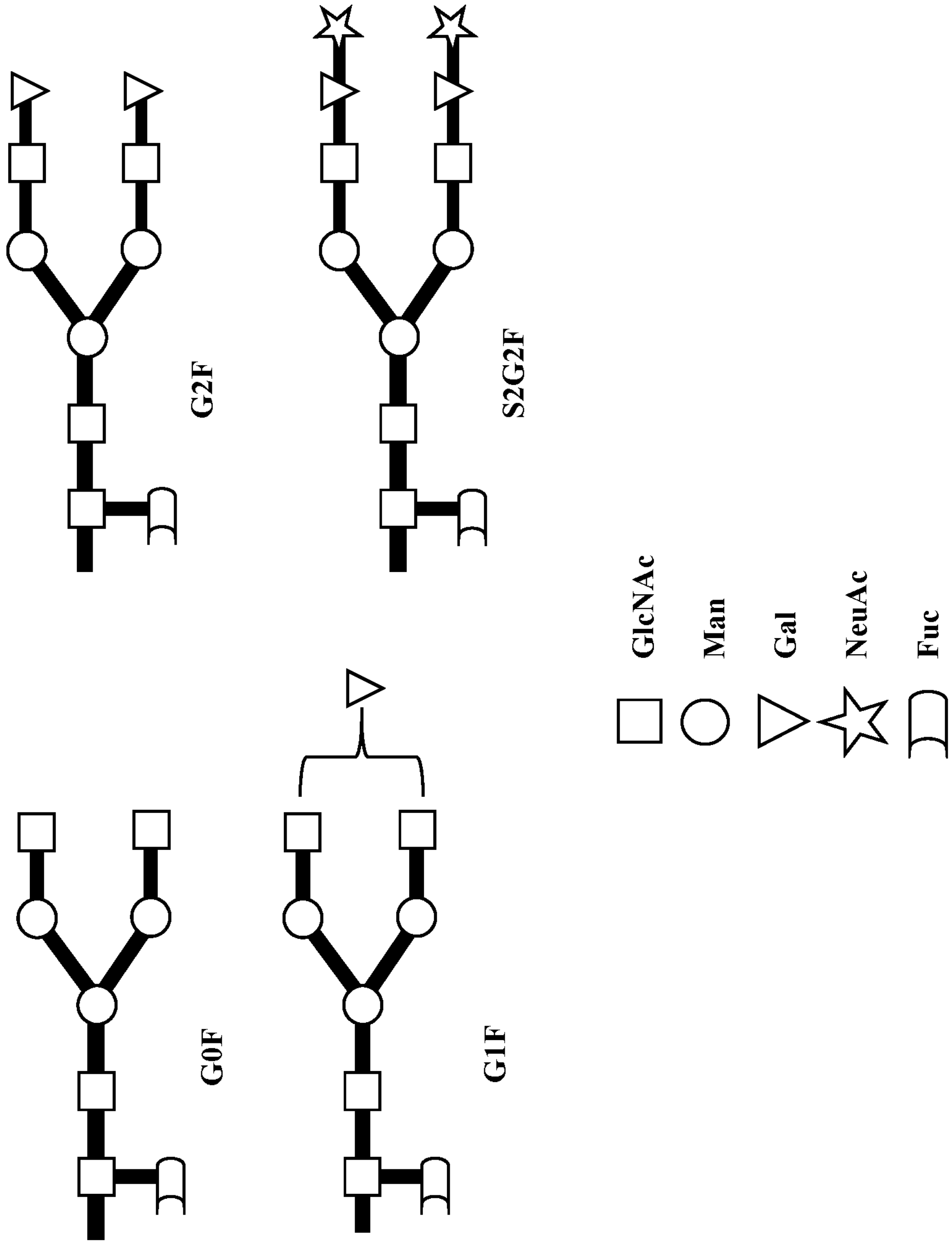
FIGS. 1B and 1C show exemplary structures of G0F (mannose-3-N-acetylglucosamine-4-fucose), G1F (mannose-3-N-acetylglucosamine-4-galactose-1-fucose), G2F (mannose-3-N-acetylglucosamine-4-galactose-2-fucose), S1G1F (mono-sialylated mannose-3-N-acetylglucosamine-4-galactose-1-fucose), S1G2F (mono-sialylated mannose-3-N-acetylglucosamine-4-galactose-2-fucose), S1G3F (monosialylated mannose-3-N-acetylglucosamine-4-galactose-3-fucose), and S2G2F (di-sialylated mannose-3-N-acetylglucosamine-4-galactose-2-fucose).
Figure 1C:
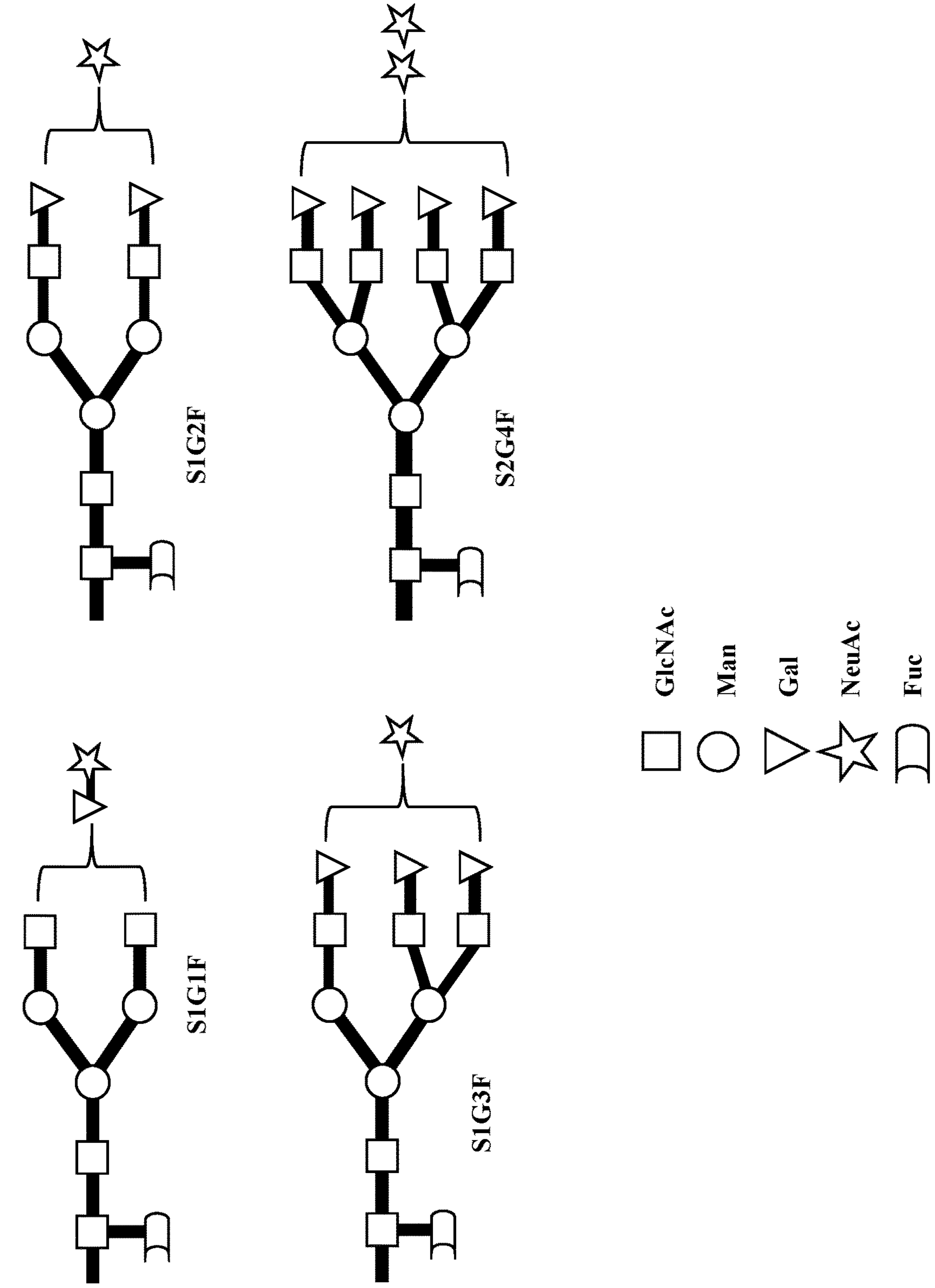
Figure 2A:
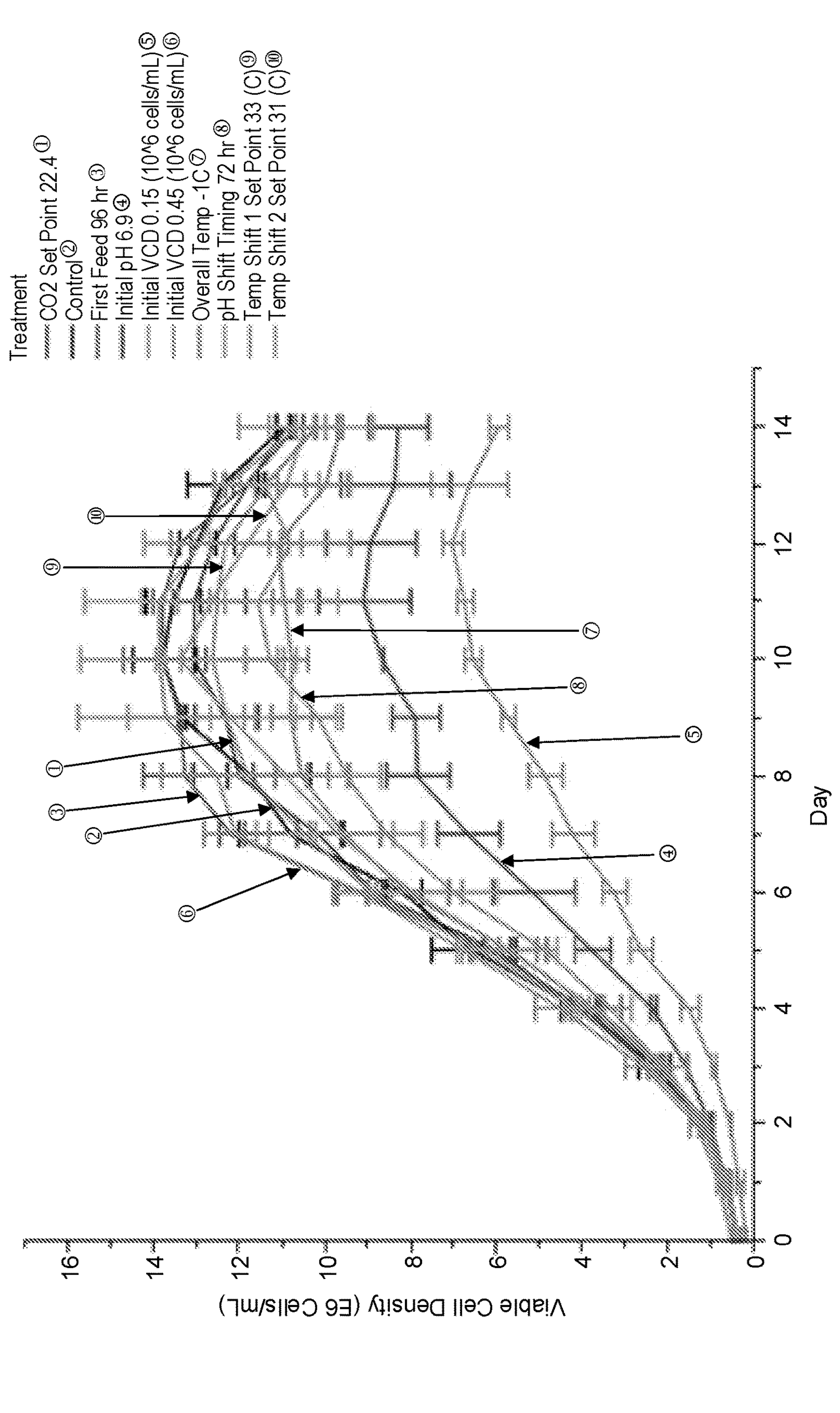
FIG. 2A shows a diagram of mean viable cell density (VCD) profiles after treatment with various conditions in a 5-L bioreactor. Tested conditions include: $CO_2$ set point of 22.4%, first feed after 96 hours, an initial pH of 6.9, an initial viable cell density of $0.15\times10^6$ cells/mL, an initial viable cell density of $0.45\times10^6$ cells/mL, an overall temperature shift of −1° C. (three temperature set points of 36° C., 33° C., and 31° C.), a pH shift timing point of 72 hours, a temperature shift at the second set point (37° C., 33° C., and 32° C.), and a temperature shift at the third set point (37° C., 34° C., and 31° C.).
Figure 3:
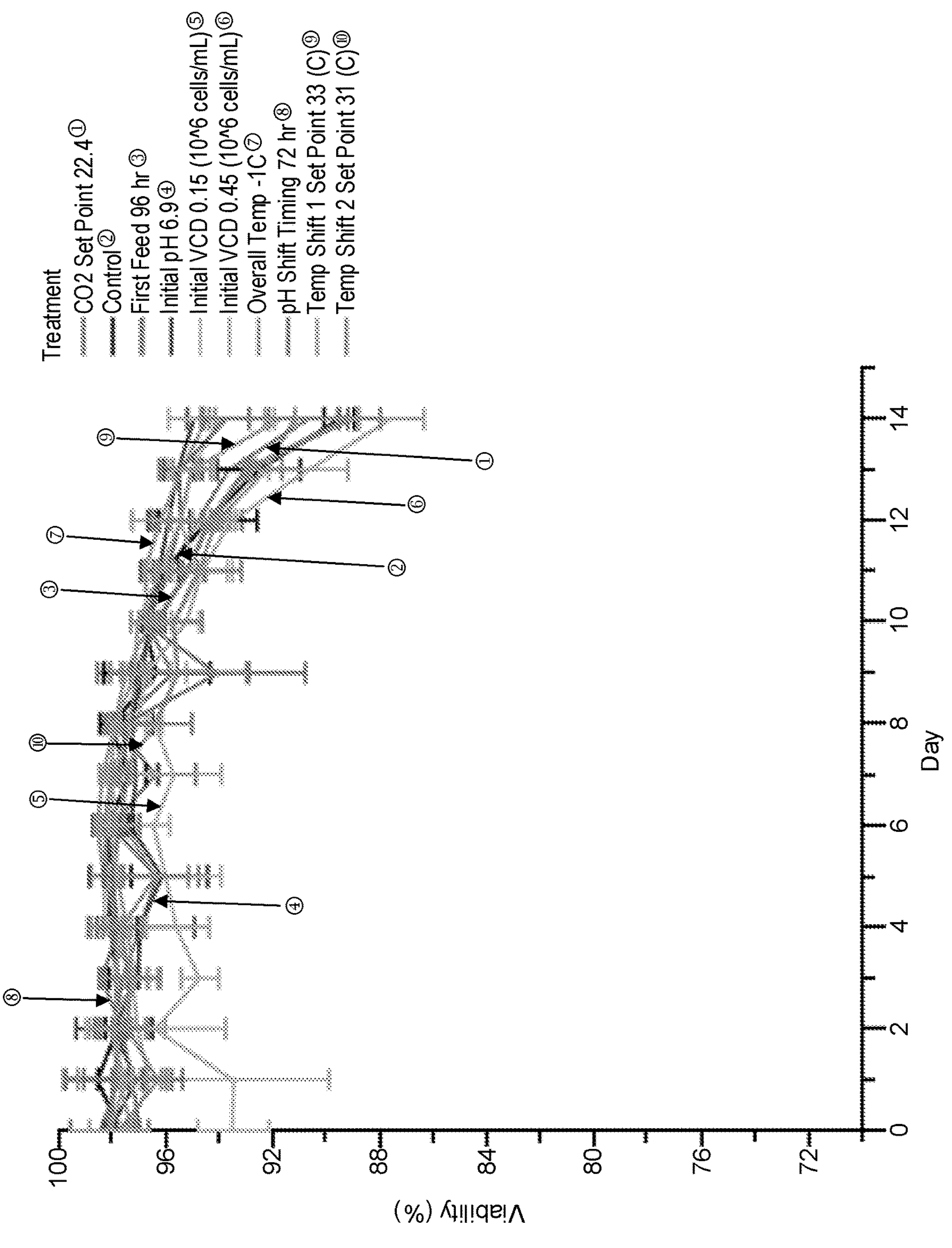
FIG. 3 shows the mean production bioreactor viability profiles for each treatment group. Tested conditions include: $CO_2$ set point of 22.4%, first feed after 96 hours, an initial pH of 6.9, an initial viable cell density of $0.15\times10^6$ cells/mL, an initial viable cell density of $0.45\times10^6$ cells/mL, an overall temperature shift of −1° C., a pH shift timing point of 72 hours, a temperature shift at the second set point (37° C., 33° C., and 32° C.), and a temperature shift at the third set point (37° C., 34° C., and 31° C.).
Figure 8B:
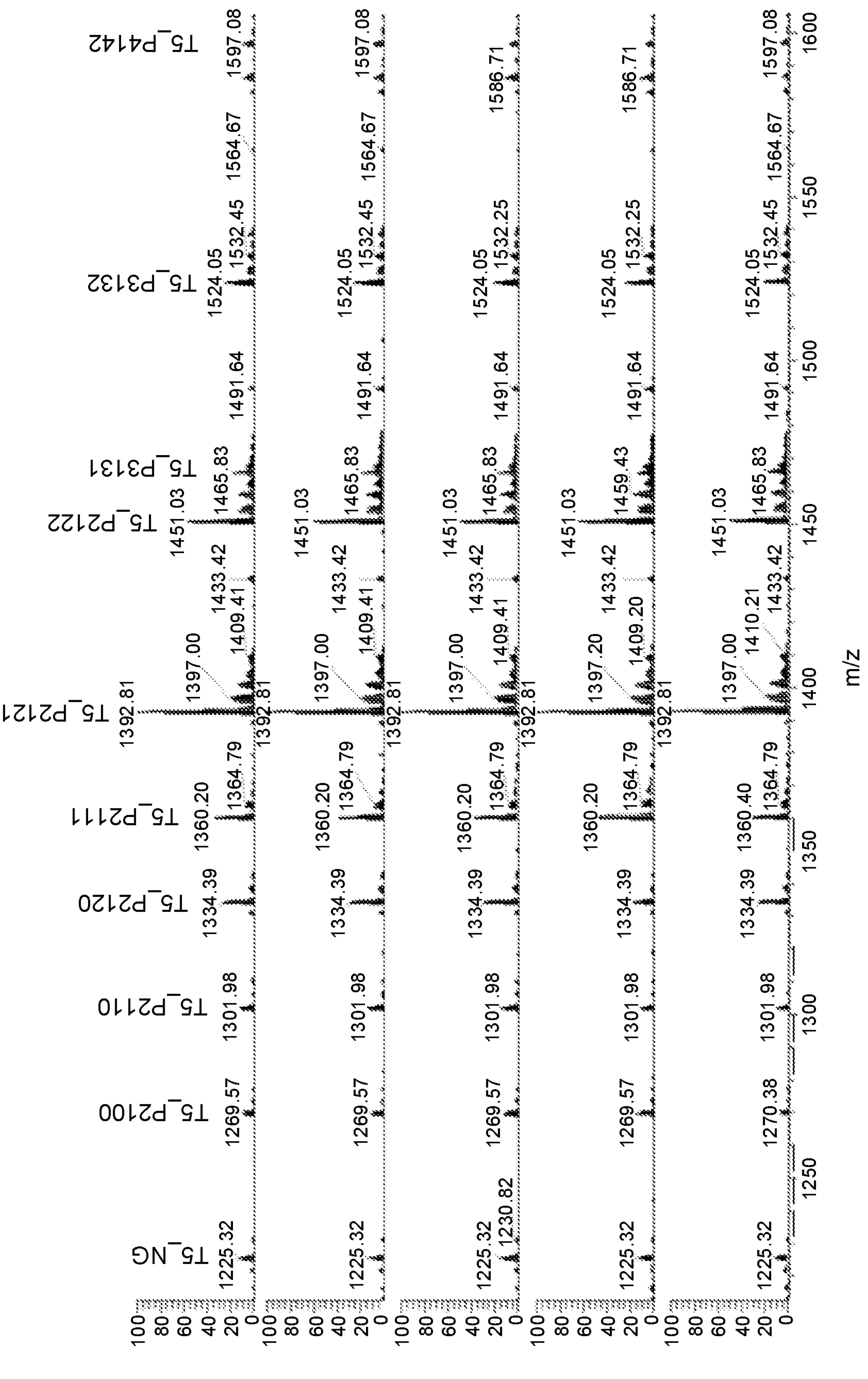
FIG. 8B shows representative mass spectrometry analysis identifying the peak representing these glycoforms. The alternate process means a control process that does not imply any of the presently disclosed conditions.
Figure 9B:
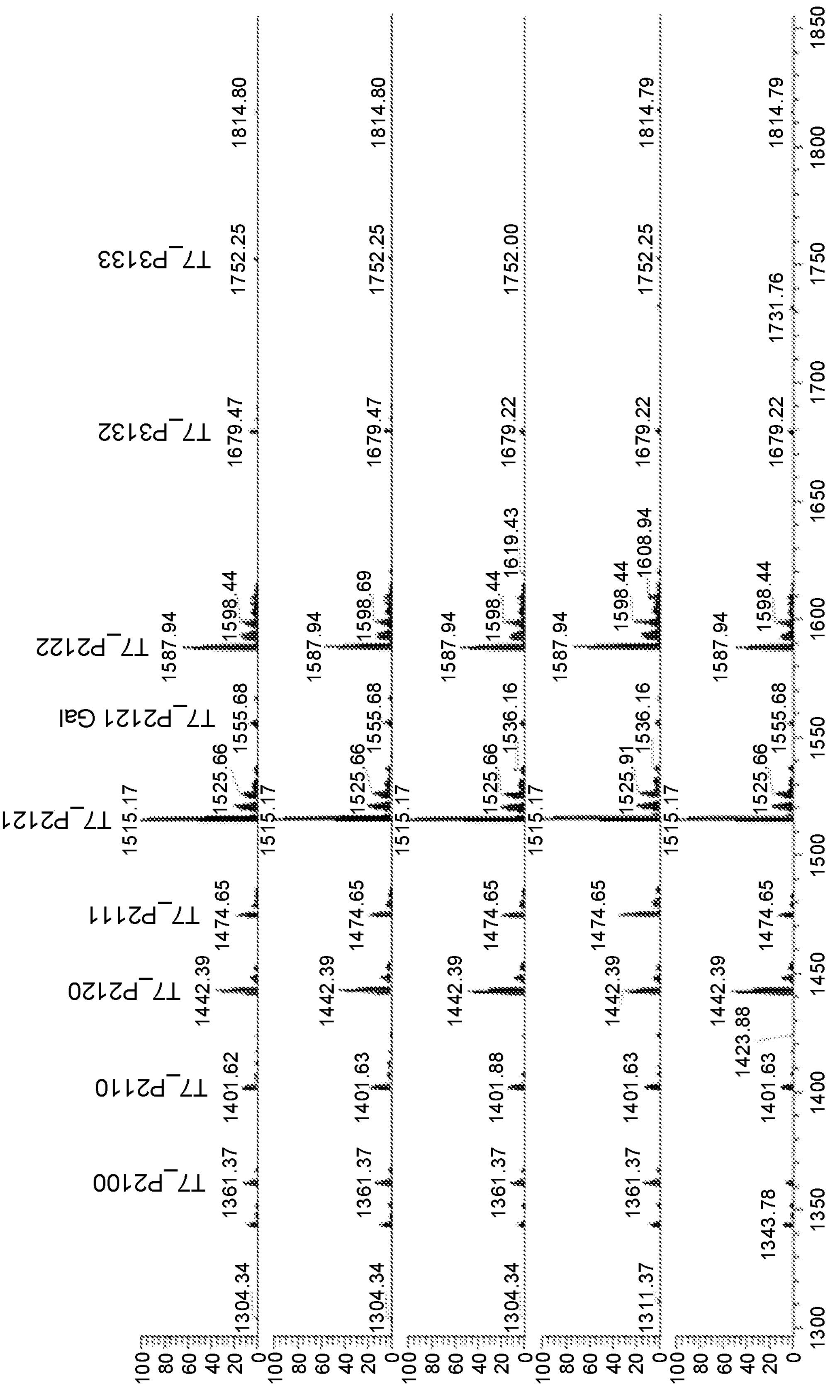
FIG. 9B shows representative mass spectrometry analysis identifying the peak representing these glycoforms

FIGS. 1A, 1B, and 1C show a variety of glycans that could potentially be present at positions T5, T7, and T14. FIG. 1D shows the specific locations of the N-linked glycosylation sites (T5, T7, and T14) in the primary amino acid sequence of Abatacept (also found in SEQ ID NO: 5). FIG. 2A shows the mean viable cell density (VCD) profiles for each treatment group, and a summary of this bioreactor cell growth data by treatment group can be seen in FIG. 2B. The low initial pH (6.9) and low initial VCD treatment groups trended at the bottom of the pack throughout the run, reaching the two lowest peak VCD values between days 11 and 12. The early pH shift condition grew similarly to the other conditions through day 3, but gradually diverged from the control group after the pH shift on day 3 and reached a lower peak VCD. The low overall temperature group showed slower growth than the control treatment from day 6 onward. The effects of this growth can be seen in the flatter shape of the curve and the relatively low peak VCD. The high initial VCD treatment group and the late first feed treatment group trended at the top of the pack from day 3 onward. Inoculum that was scaled up and passaged through two stages of 5-L seed bioreactors (N−2 and N−1) prior to the production bioreactor. The production bioreactor stage was then run for 14-17 days post inoculation. Table 1 presents the operational parameters of the center point 5-L production bioreactors used in this study. The cell viability profiles can be seen in FIG. 3 with respect to each of the tested conditions. An initial cell density of $0.45\times10^6$ cell/mL shows the greatest viability loss at day 14, down to about 86% cell viability, suggesting that the cell density reached levels too high to sustain higher levels of cell viability.

5-L Bioreactor Glycan Profile Analysis

Sialic acid content was analyzed via mass spectrometry. The mean values of the day 14 pre-harvest NANA, NANA, and N-link values, along with the p-values of a Dunnett's test comparing the result from each treatment group to the control are shown in FIG. 4A. The Domain IV+V is defined as the sum of the N-link Domain IV and Domain V values. A treatment with a p-value of ≤0.05 was considered to be significantly different from the control. The day 14 NANA, NANA, Domain I, Domain II, and Domain III values do not show a significant difference from the control values. Most of the Domain IV+V values do not show a significant difference relative to the control value. However, the low overall temperature and low temp shift 1 treatment groups yielded significantly lower levels of Domain IV+V relative to the control. The DS release specification for Domain IV+V is ≤16%, therefore this reduction poses no risk to product quality. The mean Day 14 titer and the mean specific productivity (Qp) values can be seen in FIG. 4B, along with the p-values from control Dunnett's tests comparing the treatment groups to the control. A p-value of ≤0.05 was considered a significant difference. The low initial pH, low initial VCD, and low overall temperature were shown to have significantly lower day 14 titer relative to the control. The low initial pH and early pH shift timing conditions were found to have significantly higher specific productivity than the control.

TABLE 1

5-L Production Bioreactor Center Point Operating Parameters

| Parameter | Set Point | Range |
|---|---|---|
| Generation number at transfer, from WCB thaw | N/A[a] | 25-55 |
| Medium hold time at ambient (h) | ≤48 | N/A |
| Medium hold time (pre-Inoc) at 37° C. (h) | ≤24 | N/A |
| Inoculation Viable Cell Density ($10^6$ cells/mL) | 0.3 | 0.15-0.45 |
| Initial Temperature (° C.) | 36 | 35-37 |
| Initial pH | 7.0 | 6.9-7.1 |

TABLE 1-continued

| 5-L Production Bioreactor Center Point Operating Parameters | | |
|---|---|---|
| Parameter | Set Point | Range |
| Initial Working Volume (L) | 2.5 | 2.4-2.6 |
| pH Shift Set Point | 6.9 | 6.8-7.0 |
| Timing of pH Shift (hours) | 96 | 72-120 |
| First Temperature Shift Set Point (° C.) | 33 | 32-34 |
| Timing of First Temperature Shift (hours) | 144 | 120-168 |
| Second Temperature Shift Set Point (° C.) | 31 | 30-32 |
| Timing of Second Temperature Shift Set Point (hours) | 240 | 228-252 |
| CO2 Saturation Target for Days 6-8 (% sat) | 16.8 | 11.2-22.4 |
| Base for pH and $CO_2$ Saturation Control | 1M $Na_2CO_3$ | N/A |
| Agitation (rpm) | 240 | N/A |
| Bottom Air Flow (mL/min) | 30 | N/A |
| Top Air Flow (mL/min) | 40 | N/A |
| Dissolved Oxygen (%) | 40 | 20-80 |
| Timing of First Feed Addition (hours) | 76 | 72-96 |
| Feeding Strategy | Fixed daily feed of 4.5% of post-inoculation volume at 72-96 hours and every 24 ± 4 hours thereafter until harvest | N/A |
| Glucose Addition | Bolus addition if [glucose] <2.0 g/L targeting 5 g/L final concentration using 200 g/L stock | N/A |

The study was performed in a one-factor-at-α-time (OFAT) method according to Table 2 below, with each condition changing a single parameter relative to the center point controls. The glycosylation data results can be seen in FIGS. 4A-4H. Each set point was adjusted as follows:

TABLE 2

| Experimental Design | | | |
|---|---|---|---|
| Treatment Group | Number of Replicates | Cell Culture Parameter | Set Point |
| Control | 2 | N/A | N/A |
| High $pCO_2$ | 2 | CO2 Saturation Target for Days 6-8 (%) | 22.4% |
| Late First Feed | 2 | Timing of First Feed Addition (hours) | 96 hours |
| Low Initial pH | 2 | Initial pH | 6.90 |
| Low Initial VCD | | Inoculation Viable Cell Density ($10^6$ cells/mL) | 0.15 |
| High Initial VCD | 2 | Inoculation Viable Cell Density ($10^6$ cells/mL) | 0.45 |
| Low Overall Temperature | 2 | Initial Temperature (° C.) | 36 |
| | | First Temp Shift Set Point (° C.) | 33 |
| | | Second Temp Shift Set Point (° C.) | 31 |
| Early pH Shift Timing | 2 | Timing of pH Shift (hours) | 72 |
| Low Temperature Shift 1 | 2 | First Temp Shift Set Point (° C.) | 33 |
| Low Temperature Shift 2 | 2 | Second Temp Shift Set Point (° C.) | 31 |

Experimental Results

Extended characterization of the N-glycosylation on the abatacept molecule was performed after harvest from the bioreactor. Bioreactor samples were purified using a preparative protein A Waters HPLC system. Purified samples were then concentrated using 10 kD cutoff centrifugal filter units (Millipore) to a final concentration of >4.0 g/L. The resulting abatacept protein was reduced, alkylated, and digested by trypsin, followed by GluC. The trypsin-GluC digests were separated by reversed phase chromatography and detected by mass spectrometry. The percentage of each glycoform was calculated from the peak area under extracted ion chromatogram of that glycopeptide divided by the summed peak areas from all glycopeptides of interest. Glycans are released and labeled using a fluorescent labelling kit, followed by analysis of samples on Ultra Performance Liquid Chromatography system with fluorescence detection (UPLC-FLR). Glycans G0F, G2F, S1G2F, S2G2F S1G3F and S2G4F were analyzed via mass spectrometry. The results of the analysis of these six glycans can be seen in FIGS. 4C-4H. FIG. 4C presents the average liquid chromatography-mass spectrometry (LC-MS) results for G0F glycoforms, reported in relative abundance at the T5 and T7 N-glycosylation sites on the abatacept molecule. FIG. 4D presents the average liquid chromatography-mass spectrometry (LC-MS) results for G2F glycoforms, reported in relative abundance at the T5 and T7 N-glycosylation sites on the abatacept molecule. FIG. 4E presents the average liquid chromatography-mass spectrometry (LC-MS) results for S1G2F glycoforms, reported in relative abundance at the T5 and T7 N-glycosylation sites on the abatacept molecule. FIG. 4F presents the average liquid chromatography-mass spectrometry (LC-MS) results for S2G2F glycoforms, reported in relative abundance at the T5 and T7 N-glycosylation sites on the abatacept molecule. FIG. 4G presents the average liquid chromatography-mass spectrometry (LC-MS) results for S1G3F glycoforms, reported in relative abundance at the T5 and T7 N-glycosylation sites on the abatacept molecule. FIG. 4H shows presents the average LC-MS results for S2G4F glycoforms, reported in relative abundance at the T5 N-glycosylation site on the abatacept molecule.

Example 2

Impact of Cell Age on the Pre-Harvest N-Glycoform Distribution of CTLA4-Ig Process Production Bioreactor Step In order to understand the effect of generation number of inoculum on process and quality attributes in abatacept manufacturing process at the lowered temperature set points, the edge of failure for the total number of generation of cells to inoculate bioreactors was investigated. All conditions were studied in duplicate in 5-L bioreactors. Cell vials were thawed, passaged, expanded, and finally banked at passages of 5, 10, 15, and 21. Prior to initiating this bioreactor study, the cell bank vials were thawed and expanded for six passages up to the 3-L stage. Each 3-L flask was used to inoculate a single n−2 seed bioreactor, which was then rolled into an n−1 seed bioreactor. Each n−1 seed bioreactor was used to inoculate two 5-L production bioreactors.

Cell culture performance was monitored daily including VCD, viability, pH, DO, nutrient and metabolite levels. Titer and Sialic Acid content were measured daily on days 10-16 and analyzed. High molecular weight species (HMW), residual DNA, host cell protein (HCP) and N-link glycosylation were measured on day 16 (FIG. 5). Glycoform distribution was measured by LC/MC on day 16 (FIG. 5).

Example 3

Production Bioreactor Temperature Range

In order to evaluate the allowable temperature ranges in the production bioreactor step, the effects of bioreactor inoculation viable cell density (VCD), pH shift set point, PCO2 shift set point, first temperature set point, second temperature set point and third temperature set porting on process performance and process quality were analyzed. The process parameters and characterization ranges are shown in FIG. 6A. The production bioreactor characterization was performed using 5-L Sartorius and Finesse vessels and controllers. The operating conditions for the production bioreactor step followed Table X, with the exception of the six experimental ranges shown in FIG. 6A. The set points or midpoints for the evaluated process parameters were varied among 22 treatments including 2 control as shown in Table Y. Replicates were run for the control, centerpoint conditions only.

TABLE X

5-L Production Bioreactor Center Point Operating Parameters

| Parameter | Set Point | Range |
|---|---|---|
| Inoculation Viable Cell Density ($10^6$ cells/mL) | 0.3 | 0.15-0.45 |
| Initial Temperature (° C.) | 36 | 35-37 |
| Initial pH | 7.0 | 6.9-7.1 |
| Initial Working Volume (L) | 2.5 | 2.4-2.6 |
| pH Shift Set Point | 6.9 | 6.8-7.0 |
| Timing of pH Shift (hours) | 96 | 72-100 |
| First Temperature Shift Set Point (° C.) | 33 | 32-34 |
| Timing of Temperature Shift Set Point (hours) | 144 | 120-168 |
| Second Temperature Shift Set Point (° C.) | 31 | 30-32 |
| Timing of Second Temperature Shift Set Point (hours) | 240 | 228-252 |

TABLE Y

Production Bioreactor Conditions by Vessel ID

| Bioreactor ID | Inoculation VCD (×$10^6$ cells/mL) | pH Shift Set Point | $pCO_2$ Shift Set Point | First Temp Set Point (° C.) | Second Temp Set Point (° C.) | Third Temp Set Point (° C.) |
|---|---|---|---|---|---|---|
| 180608-01 | 0.2 | 6.8 | 11.2 | 35 | 32 | 30 |
| 180608-02 | 0.5 | 7.1 | 22.4 | 37 | 32 | 31 |
| 180609-03 | 0.5 | 7.1 | 11.2 | 37 | 34 | 32 |
| 180608-04 | 0.2 | 7.1 | 22.4 | 35 | 32 | 30 |
| 180608-05 | 0.2 | 6.9 | 11.2 | 35 | 34 | 32 |
| 180608-11 | 0.2 | 6.8 | 22.4 | 36 | 32 | 32 |
| 180609-12 | 0.5 | 6.8 | 22.4 | 37 | 34 | 32 |
| 180608-14 | 0.2 | 7.1 | 16.8 | 36 | 33 | 31 |
| 180608-15 | 0.2 | 6.8 | 11.2 | 36 | 34 | 30 |
| 180608-16 | 0.2 | 7 | 11.2 | 37 | 32 | 31 |
| 180608-21 | 0.2 | 6.8 | 22.4 | 37 | 33 | 32 |
| 180608-22 | 0.2 | 7.1 | 22.4 | 37 | 34 | 30 |
| 180608-24 | 0.3 | 6.9 | 16.8 | 36 | 33 | 31 |
| 180608-31 | 0.5 | 6.9 | 22.4 | 35 | 32 | 32 |
| 180608-32 | 0.5 | 6.8 | 11.2 | 37 | 32 | 30 |
| 180608-33 | 0.3 | 6.9 | 22.4 | 37 | 32 | 30 |
| 180608-34 | 0.3 | 7.1 | 22.4 | 35 | 34 | 31 |
| 180608-36 | 0.3 | 6.9 | 16.8 | 36 | 33 | 31 |
| 180609-404 | 0.4 | 7.1 | 11.2 | 36 | 32 | 32 |
| 180608-405 | 0.5 | 6.9 | 22.4 | 35 | 32 | 32 |
| 180608-406 | 0.5 | 7.1 | 11.2 | 35 | 33 | 30 |
| 180609-407 | 0.5 | 6.8 | 11.2 | 35 | 34 | 31 |
| 180609-408 | 0.5 | 7 | 16.8 | 36 | 33 | 31 |

A summary of significant main effects of the process parameters is shown in FIG. 7. Interactions and quadratic effects of process parameters were found to be statistically significant for process performance and product quality. All quadratic effects included in the study design impacted either process attributes or quality attributes. The following parameter interactions were determined to have an impact on either process or quality attributes: Inoculation VCD x First Temperature Set Point, Inoculation VCD x Third Temperature Set Point, Inoculation VCD x Second Temperature Set Point, Second Temperature Set Point×$pCO_2$ Set Point, Second Temperature Set Point×pH Shift Set Point, and Third Temperature Shift Set Point×pH Shift Set Point.

Example 4

Commercial Scale Culturing of Suspension Mammalian Cells Expressing CTLA4-Ig:

This Example describes the production of CTLA4-Ig molecules. The methods described in this Example can be adapted and extended for the production of other proteins, including but not limited to, secreted proteins such as cytokines and other hormones, secreted proteins that are members of the Ig superfamily or comprise a portion of an Ig superfamily protein, and generally any protein expressed in CHO cells.

The culture flasks (for example, shake flasks and Erlenmeyer flasks), roller bottles, and cell bags were used for the inoculum expansion steps of the CTLA4-Ig culturing process to serially propagate cells from a frozen vial to provide a sufficient number of viable cells to inoculate a 25,000-L bioreactor.

Commercial Scale Production of CTLA4-Ig: The production phase of this disclosure occurring in a 25,000-L production bioreactor produces both high quantity and high quality CTLA4-Ig protein, which involves culture runs having a two-step temperature shift. The bioreactor is supplemented with a feed medium approximately 76 hours after induction, and this feed is provided daily to the production reactor. The 25,000 L culture is incubated in CD-CHO medium at 36° C. until approximately 144 hours after induction, and then is subjected to a temperature shift (T-shift) from 36° C. to 33° C. after about 144 hours (the end of logarithmic growth phase). The 33° C. temperature is maintained from about 144 hours to about 240 hours. The 25,000 L culture is then is subjected to a second and final temperature shift (T-shift) from 33° C. to 31° C. after about 240 hours from induction, and is maintained from about the 240-hour point to harvest.

Samples were taken on a daily basis from the production bioreactor for analysis. For example, a sample used for cell counting was stained with trypan blue (Sigma, St. Louis, Mo.). Cell count and cell viability determination was performed using a hemocytometer to count viable stained cells under the microscope. For analysis of metabolites, an additional sample aliquot was centrifuged for 20 minutes at 2000 rpm (4° C.) to pellet the cells. The supernatant was analyzed for protein titer, sialic acid, glucose, lactate, glutamine, glutamate, pH, $pO_2$, $pCO_2$, ammonia, and LDH, using techniques and protocols conventionally practiced in the art.

Example 5

Glycosylation Analysis of CTLA4-Ig Produced in 25,000 L Bioreactor

Imaged Capillary Isoelectric Focusing (iCIEF) was performed to analyze the glycan content. This method is used for the separation of proteins by their isoelectric point (pI). In this method, abatacept samples are prepared to a final concentration of ~1 mg/mL with water, methyl cellulose, ampholytes, and pI markers, and then injected by an autosampler into an imaged capillary isoelectric focusing system (iCIEF). Electrophoresis separates the samples through a pH gradient within a fluorocarbon (FC) coated capillary based on charge variance of the isoforms. After high voltage focusing, sample migration is captured by a whole column CCD camera and quantitative analysis of the peaks is performed using the associated software. Results are reported as a percentage of the total glycoforms present in the sample, and can be seen in FIGS. 8A-8B and 9A-9B.

Glycosylation Domain Analysis of CTLA4-Ig Produced in 25,000 L Bioreactor

Figure 10A:
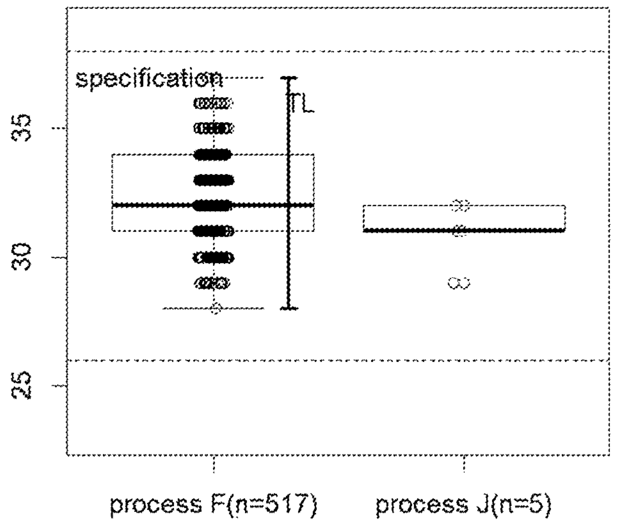
FIGS. 10A-10F show statistical comparisons of various sialylated N-linked glycans compared between the processes used in the present disclosure (J), and an alternate process (F). Glycan analysis includes Domain I (FIG. 10A), Domain II (FIG. 10B), Domain III (FIG. 10C), Domain IV+V (FIG. 10D), NANA (FIG. 10E), and NANA (FIG. 10F).
Figure 10B:
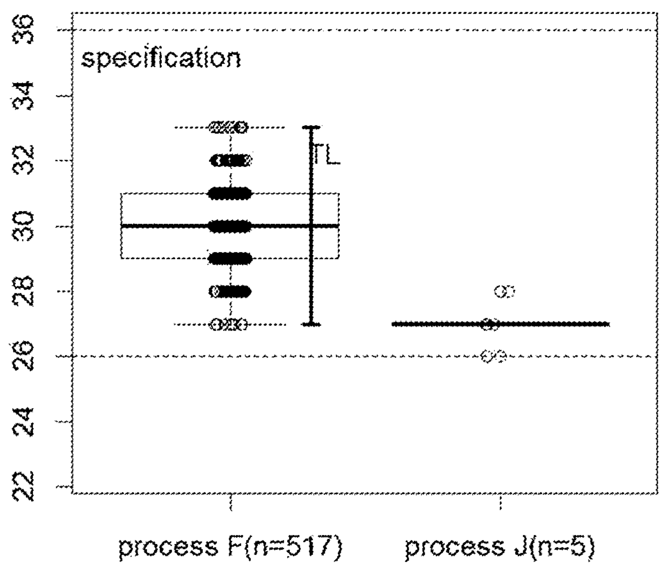
Figure 10C:
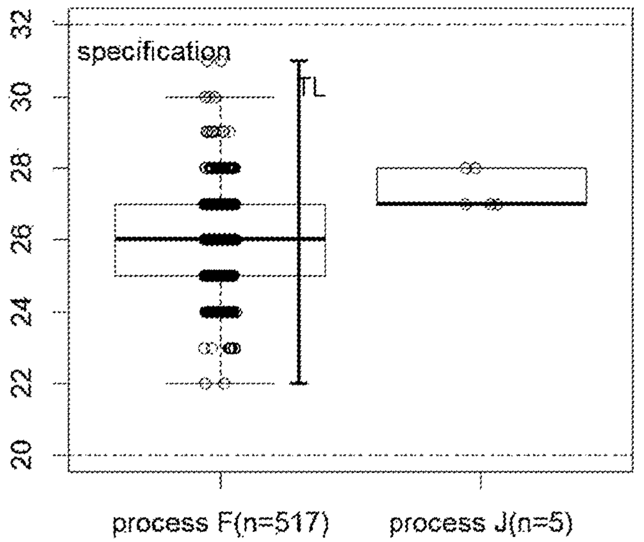
Figure 10D:
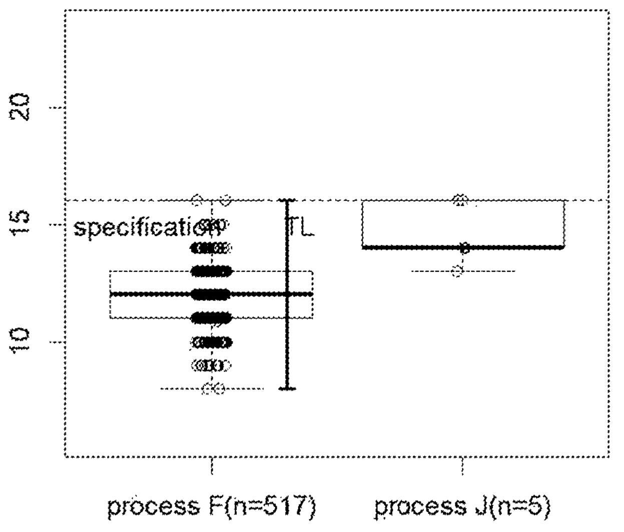
Figure 10E:
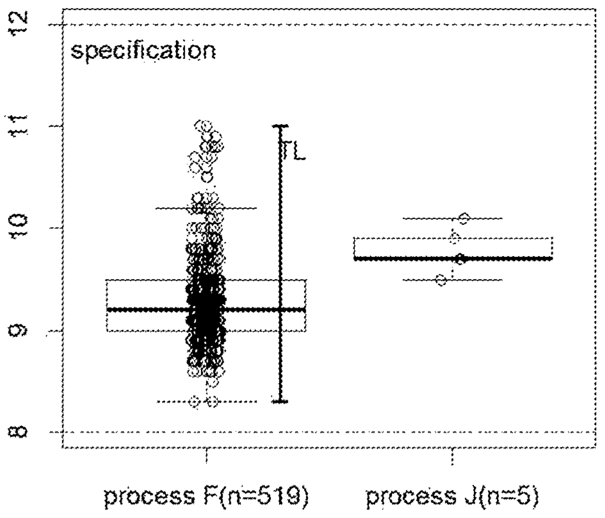
Figure 10F:
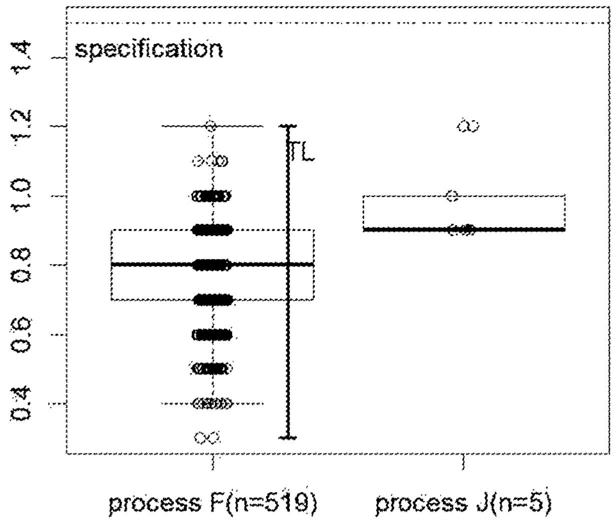

The N-linked oligosaccharides profile (glycosylation pattern) of abatacept is determined. The oligosaccharides on abatacept are liberated by enzymatic hydrolysis with PNGase F. The free oligosaccharides are profiled by high performance anion exchange chromatography (HPAEC) using electrochemical detection. Oligosaccharide profiles of drug substance are evaluated against concurrently run samples of reference material. Results are reported as either as an absolute percent area of selected domains or a percent deviation of selected domains from the same domains in the reference standards. Domains I, II, III, and VI+V results can be seen in FIGS. 10A-10D. The results of the sialic acid analysis (NANA and NANA can be seen in FIGS. 10E and 10F.

Example 6

In Vivo Efficacy of Abatacept

A clinical study was conducted to compare the pharmacokinetics of abatacept prepared by the reference process (e.g., Process F, which is described in PCT/US2006/049074) and the process described herein (e.g., Process J). The clinical study was an open-label, randomized, parallel-group, single-dose study conducted to compare the pharmacokinetics (PK) of abatacept manufactured by the process described herein relative to the reference process following a single dose (750 mg administered as a 30-minute IV infusion) in healthy participants.

Results of the clinical PK study demonstrated the need for control of the N-glycan composition of abatacept. N-glycan composition was determined by HILIC N-Linked Glycan profiling method. This method was designed to quantitate the summation of major biantennary glycoforms on the CTLA4 region, which impacted PK.

The clinical studies demonstrated that CTLA4 G2F, S1G2F, and S2G2F glycoforms are the most influential to the overall control strategy and PK, therefore two-side limits were proposed for these glycans (Table 3). CTLA4 G2F is a critical quality attribute for abatacept due to strong correlation to PK clearance. S1G2F had a minimal impact on PK and a 2-sided limit was applied for manufacturing consistency. A 2-sided limit was applied to S2G2F, due to its strong correlation to G2F in both the manufacturing process and clearance. One-sided limits were proposed for G0F, G1F, and S1G1F as they had negligible impact on overall clearance. Additional justifications are provided in Table 3. The proposed limits for all glycans in Table 3 ensured control of glycans within accepted PK parameters. Failure of one attribute triggered rejection of the batch to maintain consistency with clinical and manufacturing experience.

TABLE 3

| Glycan | Optimal Range | Justification |
|---|---|---|
| G0F | ≤6.5% | Revised limit is based on clinical and manufacturing experience from Process F and J, including additional Process J manufacturing experience. |
| G1F | ≤7.0% | Revised limit is based on clinical and manufacturing experience from Process F and J, including additional Process J manufacturing experience. |
| G2F | 1.5%-23% | G2F is a fast-clearing glycan and has correlation to PK outcome. Revised limit is based on clinical and manufacturing experience from Process F and J, including additional Process J manufacturing experience. |
| S1G1F | ≤12.5% | Revised limit is based on clinical and manufacturing experience from Process F and J, including additional Process J manufacturing experience. |
| S1G2F | 32.0%-49.0% | S1G2F is slow clearing and does not correlate with PK outcome. Revised limit is based on clinical and manufacturing experience from Process F and J, including additional Process J manufacturing experience. |
| S2G2F | 14.0%-48.5% | S2G2F is slow-clearing glycan and has correlation to PK outcome. Revised limit is based on clinical and manufacturing experience from Process F and J, including additional Process J manufacturing experience. |

What is claimed is:

1. A method of controlling cell growth rate, cell viability, viable cell density and/or titer of cells for producing abatacept comprising culturing the cells in a bioreactor under suitable conditions, wherein the suitable conditions comprise;

(i) a protein induction phase under an initial temperature set point of 36° C.; and (ii) culturing the cell in a second temperature set point of 33° C. and a final temperature set point of 31° C.;

and the suitable conditions further comprise a) a pH shift at 96 hours±20%;

b) an initial pH set point of 7.0 and a second pH set point of 6.9, or an initial pH set point of pH 6.9;

c) an initial viable cell density (VCD) set point of $0.30\times10^6$ cells/mL;

d) an initial $CO_2$ set point between 15% and 25%;

e) a first feed time at 76 hours±20%; or f) any combination thereof;

wherein the suitable conditions improve the abatacept yield compared to a method without the suitable conditions.

2. The method of claim 1, wherein the suitable conditions comprise:

a) an initial temperature set point of 36° C., a second temperature set point of 33° C., and a third temperature set point of 31° C.;

b) an initial pH set point of 7.0 and a second pH set point of 6.9;

c) an initial VCD set point of $0.30\times10^6$ cells/mL; and, d) an initial $CO_2$ set point between 15% and 25%.

3. The method of claim 1, wherein (i) the final temperature set point occurs at 228 hours to 252 hours, (ii) wherein the second temperature set point occurs at 120 hours to 168 hours, or (iii) both (i) and (ii).

4. The method of claim 1, wherein the suitable conditions improve the abatacept yield by at least 150% as compared to a method without the suitable conditions.

5. The method of claim 1, wherein the method:

(i) reduces cell growth rate, (ii) controls a cell viability, (iii) controls a titer, (iv) controls a glycosylation profile of abatacept, or (v) any combination of (i)-(iv).

6. The method of claim 5, wherein:

(i) the cell growth exhibits a mean 0-5 day doubling time of from 30.0 hours±20% to 40.0 hours±20%;

(ii) the cell viability exhibits:

(a) a mean peak VCD of from $10.0\times10^6$ cells/mL±20% to $15.0\times10^6$ cells/mL±20%; or, (b) a mean 0-14 day integral of viable cell density (IVCD) of from $0.05\times10^9$ cells/mL±20% to $0.11\times10^9$ cells/mL±20%;

(iii) the titer exhibits:

(a) a mean day 14 titer of 1.50 g/L±20% to 3.5 g/L±20%; or (b) a mean specific productivity of from 20.0 pg/cell-day±20% to 40.0 pg/cell-day±20%;

(iv) the glycosylation profile comprises one or more N-linked glycan; or, (v) any combination of (i)-(iv).

7. The method of claim 6, wherein the N-linked glycans comprise: G0F, G1F, G2F, S1G1F, S1G2F, and/or S2G2F.

8. The method of claim 7, further comprising measuring the glycosylation profile after day 14.

9. The method of claim 7, wherein:

(i) GOF comprises a relative abundance of less than or equal to 7.0%, or of 6.5%;

(ii) GIF comprises a relative abundance of less than or equal to 7.5%, or of 7%;

(iii) G2F comprises a relative abundance of less than or equal to 25%, or of 1.5% to 23%;

(iv) S1G1F comprises a relative abundance of less than or equal to 13.5%, or of 12.5%;

(v) S1G2F comprises a relative abundance of more than or equal to 33%, or of 32% to 49%;

(vi) 2G2F comprises a relative abundance of more than or equal to 12%, or of 14% to 48.5%; or, (vii) any combination of (i)-(vi).

10. The method of claim 7, wherein:

(i) G2F comprises a relative abundance of 1.5% to 23%, S1G2F comprises a relative abundance of 32% to 49%, and/or S2G2F comprises a relative abundance of 14% to 48.5%;

(ii) G2F comprises a relative abundance of less than or equal to 25%, S1G2F comprises a relative abundance of more than or equal to 33%, and/or S2G2F comprises a relative abundance of more than or equal to 12%;

(iii) GOF comprises a relative abundance of less than or equal to 6.5%, GIF comprises a relative abundance of less than or equal to 7%, G2F comprises a relative abundance of 1.5% to 23%, S1G1F comprises a relative abundance of less than or equal to 12.5%, S1G2F comprises a relative abundance of 32% to 49%, and/or S2G2F comprises a relative abundance of 14% to 48.5%; or (iv) GOF comprises a relative abundance of less than or equal to 7.0%, G1F comprises a relative abundance of less than or equal to 7.5%, G2F comprises a relative abundance of less than or equal to 25%, SIG1F comprises a relative abundance of less than or equal to 13.5%, S1G2F comprises a relative abundance of more than or equal to 33%, and/or S2G2F comprises a relative abundance of more than or equal to 12%.

11. The method of claim 1, wherein the process further comprises modifying an upstream bioreactor parameter, wherein the upstream reactor parameter comprises (i) a feed time, (ii) an initial pH, (iii) a pH shift, (iv) a $CO_2$ concentration, (v) an initial cell density, or (vi) any combination thereof.

* * * * *